`US005879909A`

United States Patent [19]
Perl

[11] Patent Number: 5,879,909
[45] Date of Patent: Mar. 9, 1999

[54] HUMAN TRANSALDOLASE: AN AUTOANTIGEN WITH A FUNCTION IN METABOLISM

[75] Inventor: Andras Perl, Jamesville, N.Y.

[73] Assignee: The Research Foundation of State University of New York, Albany, N.Y.

[21] Appl. No.: 57,762

[22] Filed: Apr. 9, 1998

Related U.S. Application Data

[62] Division of Ser. No. 326,119, Oct. 19, 1994.

[51] Int. Cl.$^6$ .............................. C12P 21/06; C07H 21/04
[52] U.S. Cl. ...................... 435/69.1; 435/325; 536/23.1; 536/24.1; 530/350
[58] Field of Search ................................. 536/23.1, 24.1; 435/325, 69.1; 530/350

[56] References Cited

PUBLICATIONS

Perl, A. et al., "Human Endogenous Retroviral Elements and Autoimmunity: Data and Concepts" (1993) *Trends. Microbiol.* 1:153–156.

Perl, A. et al., "Detection and Cloning of New HTLV–Related Endogenous Sequences in Man" (1989) *Nucl. Acids Res.* 17:6841–6854.

Banki, K. et al., "Cloning and Expression of the Human Gene for Transaldolase" (1994) *J. Biol. Chem.* 269:2847–2851.

Banki, K. et al., "Human T–Cell Lymphotropic Virus (HTLV)–Related Endogenous Sequence, HRES–1, Encodes a 28–kDa Protein: A Possible Autoantigen for HTLV–1 Gag–Reactive Autoantibodies" (1992) *Proc. Natl. Acad. Sci. USA*, 89:1939–1943.

Banki et al., "Effect of p40$^{tax}$ trans–Activator of Human T–Cell Lymphotropic Virus Type I on Expression of Autoantigens" (1994) *AIDS Res. Human Retrovir.* 10:303–308.

Schaaf, I. et al., "Molecular Analysis of the Structural Gene for Yeast Transaldolase" (1990) *Eur. J. Biochem.* 188:597–603.

Seiki, M. et al., "Human Adult T–Cell Leukemia Virus: Complete Nucleotide Sequence of the Provirus Genome Integrated in Leukemia Cell DNA" (1983) *Proc. Natl. Acad. Sci. USA* 80:3618–3622.

Koprowski, H. et al., "Multiple Sclerosis and Human T–Cell Lymphotropic Retroviruses" (1985) *Nature* 328:154–160.

Ohta, M. et al. "Sera From Patients With Multiple Sclerosis React with Human T–Cell Lymphotropic Virus–1 GAG Proteins but Not ENV Proteins—Western Blotting Analysis" (1986) *J. Immunol.* 137:3440–3443.

Ranki, A. et al., "Interpretation of Antibodies Reacting Solely with Human Retroviral Core Proteins" (1988) *N. Engl. J. Med.* 318:448–449.

McCarron, R. M. et al., "Alterations in T–Cell Antigen Specificity and Class II Restriction During the Course of Chronic Relapsing Experimental Allergic Encephalomyellitis" (1990) *J. Neuroimmunol.* 39:73–79.

Witham, R. H. et al., "Location of a New Encephalitogenic Epitope (Residues 43 to 64) in Proteolipid Protein that Induces Relapsing Experimental Autoimmune Encephalomyelitis in PL/J and (SJL x PL)F$_1$ Mice" (1991) *J. Immunol.* 147:3803–3808.

Post, G.R. et al., "Regulation of Carbachol– and Histamine–Induced Inositol Phospholipid Hydrolysis in a Human Oligodendroglioma" (1992) *GLIA* 5:122–130.

Massa, P.T. et al., "Cell Type–Specific Regulation of Major Histocompatability Complex (MHC) Class I Gene Expression in Astrocytes, Oligodendrocytes, and Neurons" (1993) *GLIA* 8:201–207.

Kaufman, D.L., et al., "Glutamate Decarboxylases and Autoimmunity in Insulin–Dependent Diabetes" (1993) *Trends Pharm. Sci.* 14:107–109.

Yura, T. et al., (1992) *Nucleic Acid Res.* 20:3305–3308.

*Primary Examiner*—Lila Feisee
*Assistant Examiner*—Minh-Tam Davis
*Attorney, Agent, or Firm*—Morrison & Foerster LLP

[57] ABSTRACT

Transaldolase is an enzyme which acts as an autoantigen in immune-related neurodegenerative diseases, particularly multiple sclerosis. Human transaldolase, the DNA coding therefore, peptides derived therefrom, and DNA control elements associated therewith and anti-transaldolase antibodies are disclosed. These compositions are useful in methods such as immunoassays for detecting subjects making anti-transaldolase antibodies and diagnosing the neurodegenerative disease.

14 Claims, 22 Drawing Sheets

```
                                                          ↓exon 1
    GAATTCCGCGGCCCGTCCCGTCGCCGCCGCCCGCCCGCAGACCCCTCGGTCTCTGCTATGT
  → ‾‾‾‾‾‾‾‾‾‾----+---------+---------+---------+---------+---------+   60
  1 ----+---------+---------+---------+---------+---------+
                                                                  M  S  -

CGAGCTCACCCGTGAAGCGTCAGAGGATGGAGTCCGCGCTGGACCAGCTCAAGCAGTTCA
 61 ----+---------+---------+---------+---------+---------+  120
     S  S  P  V  K  R  Q  R  M  E  S  A  L  D  Q  L  K  Q  F  T  -
                                    ↓exon 2

CCACCGTGGTGGCCGACACGGGCGACTTCCACGCCATCGACGAGTACAAGCCCCAGGATG
121 ----+---------+---------+---------+---------+---------+  180
     T  V  V  A  D  T  G  D  F  H  A  I  D  E  Y  K  P  Q  D  A  -

CTACCACCAACCCGTCCCTGATCCTGGCCGCAGCACAGATGCCCGCTTACCAGGAGCTGG
181 ----+---------+---------+---------+---------+---------+  240
     T  T  N  P  S  L  I  L  A  A  A  Q  M  P  A  Y  Q  E  L  V  -
                                           ↓exon 3

TGGAGGAGGCGATTGCCTATGGCCGAAGCTGGGGTCACAAGAGGACCAGATTAAAA
241 ----+---------+---------+---------+---------+---------+  300
     E  E  A  I  A  Y  G  R  K  L  G  G  S  Q  E  D  Q  I  K  N  -

ATGCTATTGATAAACTTTTTGTGTTGTTTGGAGCAGAAATACTAAAGAAGATTCCGGGCC
301 ----+---------+---------+---------+---------+---------+  360
     A  I  D  K  L  F  V  L  F  G  A  E  I  L  K  K  I  P  G  R  -

FIG. 2A
```

```
            ↓exon 4
      GAGTATCCACAGAAGTAGACGCAAGGCTCTCCTTTGATAAAGATGCCATGGTGGCCAGAG
361   ------+---------+---------+---------+---------+---------+  420
       V  S  T  E  V  D  A  R  L  S  F  D  K  D  A  M  V  A  R  A CCAGGCGGCTCATCGAGCTCTACAAGGAAGCTGGGATCAGCAAGGACCGAATTCTTATAA
421   ------+---------+---------+---------+---------+---------+  480
       R  R  L  I  E  L  Y  K  E  A  G  I  S  K  D  R  I  L  I  K AGCTGTCATCAACCTGGGGAAGGAATTCAGGCTGGAAAGGAGCTCGAGGAGCAGCACGGCA
481   ------+---------+---------+---------+---------+---------+  540
       L  S  S  T  W  E  G  I  Q  A  G  K  E  L  E  E  Q  H  G  I TCCACTGCAACATGACGTTACTCTTCTCCTTCGCCCAGGCTGTGGCCTGTGCCGAGGCGG
541   ------+---------+---------+---------+---------+---------+  600
       H  C  N  M  T  L  L  F  S  F  A  Q  A  V  A  C  A  E  A  G GTGTGACCCTCATCTCCCCATTTGTGGGGCGCATCCTTGATTGGCATGTGGCAAACACCG
601   ------+---------+---------+---------+---------+---------+  660
       V  T  L  I  S  P  F  V  G  R  I  L  D  W  H  V  A  N  T  D ACAAGAAATCCTATGAGCCCCTGGAAGACCTGGGGTAAAGAGTGTCACTAAAATCTACAACT
661   ------+---------+---------+---------+---------+---------+  722
       K  K  S  Y  E  P  L  D  E  P  G  K  S  V  T  K  I  Y  N  Y ACTACAAGAAGTTTAGCTACAAAACCATTGTCATGGGCGCCCTCCTTCCGCAACACGGGCG
723   ------+---------+---------+---------+---------+---------+  782
       Y  K  K  F  S  Y  K  T  I  V  M  G  A  S  F  R  N  T  G  E
```

FIG. 2B

```
     AGATCAAAGCACTGGCCGGCTGTGACTTCCTCACCATCTCACCCAAGCTCCTGGGAGAGC
783  ------------------------------------------------------------  842
       I  K  A  L  A  G  C  D  F  L  T  I  S  P  K  L  L  G  E  L

TGCTGCAGGACAACGCCAAGCTGGTGCCTGTGCTCTCAGCCAAGGCGGCCCAAGCCAGTG
843  ------------------------------------------------------------  902
       L  Q  D  N  A  K  L  V  P  V  L  S  A  K  A  A  Q  A  S  D
                                                                    ↓exon 5
     ACCTGGAAAAAATCCACCTGGATGAGAAGTCTTTCCGTTGGTTGCACAACGAGGACCAGA
903  ------------------------------------------------------------  962
       L  E  K  I  H  L  D  E  K  S  F  R  W  L  H  N  E  D  Q  M TGGCTGTGGAGAAGCTCTCTGACGGGATCCGCAAGTTTGCCGCTGATGCAGTGAAGCTGG
963  ------------------------------------------------------------  1022
       A  V  E  K  L  S  D  G  I  R  K  F  A  A  D  A  V  K  L  E AGCGGGATGCTGACAGAACGAATGTTCAATGCAGAGAATGGAAAGTAGCGCATCCCCTGAGG
1023 ------------------------------------------------------------  1082
       R  M  L  T  E  R  M  F  N  A  E  N  G  K  *

CTGGACTCCAGATCTGCACCGCCAGCTGGGATCTGACTGCACGTGGCTTCTGATGA
1083 ------------------------------------------------------------  1142

ATCTTGCGTTTTTACAAATTGGAGCAGGGACACAGATCATAGATTTCTGATTTTATGTAAA
1143 ------------------------------------------------------------  1202

ATTTTGCCTAATACATTAAAGCAGTCACTTTTCCTGTGCTGTTTCAAAAAAAAAAAAAAAA
1203 ------------------------------------------------------------  1262

AAAAAAAAAAAAAAAAAAAAAAAAAAAAAAAAAAAAAAAAAAAAAAAAAAAAAAAAAAAA
1263 ------------------------------------------------------------  1322

AAGGAATTC
1323 ---------  1331
```

FIG. 2C

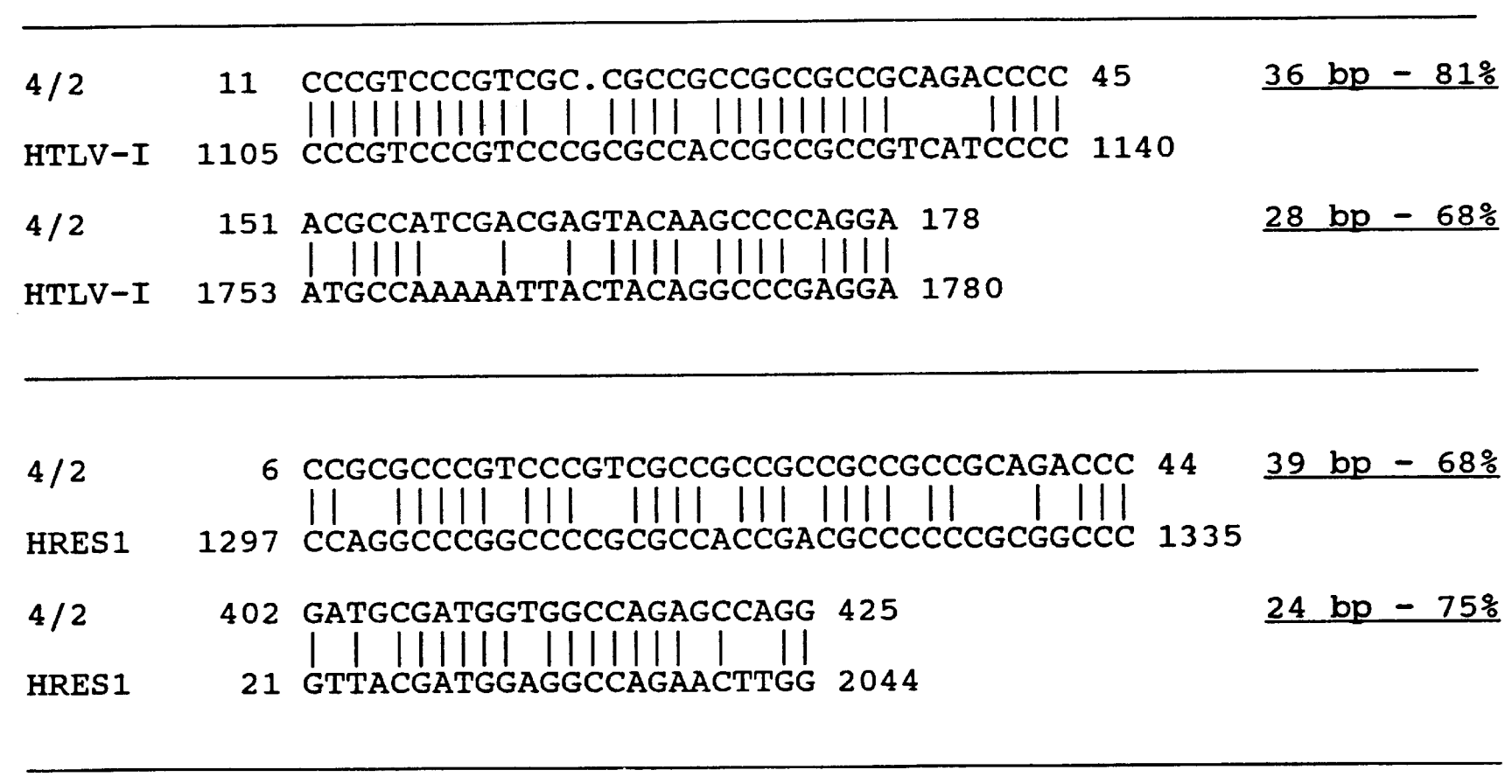

```
4/2        11  CCGTCCCGTCGC.CGCCGCGCCGCAGACCCC   45          36 bp - 81%
                |||||||||||| ||||||||||||||||||
HTLV-I   1105  CCCGTCCC

```
              Calkin
TAL-H    1  MSSSPVKRQRM.ESALDQLKQFTT..VVADTGDFHAIDEYKPQDATTNPSL   48
            ||.:.|.:::.|:::|||...|.||||.|||||||.||||||||||||
TAL-Y    1  MSEPAQKQKVANNSLEQLKASGTVVADTGDFGSIAKFQPDSTTNPSL    50

TAL-H   49  ILAAAQMPAYQELVEEAIAYGRKLGGSQEDQIKNAIDKLFVLFGAEILKK    98
            |||||.|.|||.|.::.|..|:.|..:.|.|:|||||||||.||||.||
TAL-Y   51  ILAAAKQPTYAKLIDVAVEYGKKHGKTTEEQVENAVDRLLVEFGKEILKI   100

TAL-H   99  IPGRVSTEVDARLSFDKDAMVARARRLIELYKEAGISKDRILIKLSSTWE   148
            :|||||||||||||||:|::.:.|:||||||||||||.|||||||.|||
TAL-Y  101  VPGRVSTEVDARLSFDTQATIEKARHIIKLFEQEGVSKERVLIKIASTWE   150

TAL-H  149  GIQAGKELEEQHGIHCNMTLLFSFAQAVACAEAGVTLISPFVGRILDWHV   198
            |||||||||||||||||||||||||||||||||||||||||||||||||
TAL-Y  151  GIQAAKELEEKDGIHCNLTLLFSFVQAVACAEAQVTLISPFVGRILDWYK   200
                                                  cAMP-P/
TAL-H  199  ANTDKKSYEPLDEPGVKSVTKIYNYKKFSYKTIVMGASFRNTGEIKALAG   249
            ..|:..:..|:|.||.|:.:||||:|||||||||||:|.:..|.||||
TAL-Y  201  SSTGKDYKGEADPG VISVKKMYNYKKYGYKTIVMGASFRSTDEIKNLAG   250

TAL-H  249  CDFLTISPKLLGELLQDNAKLVPVLSAKAAQASDLEKIHL..DEKSFRWL   297
            .:||||||.|||.|.||.|.||||.||||||||.|||||...||:|||.
TAL-Y  251  VDYLTISPALLDKLMNSTEPFPRVLDPVSAKKEAGDKISYISDESKFRFD   300

TAL-H  297  HNEDQMAVEKLSDGIRKFAADAVKLERMLTERMFNAENGK    336
            .|||.||.|||:|||||||||.|||||||.|::||:..:.
TAL-Y  301  LNEDAMATEKLSEGIRKFSADIVTLFDLIEKKVTA.....   335

FIG. 5
```

```
HTLV-I gagp19    45 QLKKFLKIALET 56                                                                                    42%
TAL-H            17 QLKQFTTVVADT 28

HTLV-I gag p24  230 ......QANNPQQQGLRREYQQLWLAAFAALPGSAKDPSWASILQGLEEPY 274
                          :   ||| ||  ::            |||||  ::
TAL-H            30 DFHAIDEYKPQDATTNPS...LILAA.AQMPA.........YQELVEEA 65

275 HAFVERLNIALDNGLPEGTPK......DPILRSLAYSNANKECQKLL... 315
                     : :   :   ::       :       | ::: :   |||||||||
                 66 IAYGRKLGGSQEDQIKNAIDKLFVLFGAEILKKIP.GRVSTEVDARLSFD 114

316 .QARGHTNSPLGDMLRACQTWTPKDKTKVL 344       22%  (40%)
                     ::                        : :
                115 KDAMVARARRLIELYKEAG..ISKDRI... 139

TAL-H            12 ESALDQLKQFTTVVADTGDFHAIDEYKPQDATTNPSLILAAAQMPAYQELV 62
                        :|| ||| ||||  ||||||||||||||||
HIV p17         106 EEQNKSKKKAQQAAADTGHSNQVSQNYPIVQNIQGQMVHQAISPRTLNAWV 156   18%

HTLV-I g24      299 LRSLAYSNANKECQKLLQARGHTNSPLGDMLRACQTWTPKDKTKVL 344       24%
                     |:||       ||| : | |    |||   :|  | ::||
TAL-H           243 IKALAGCDFLTISPKLLGELLQDNAKLVPVLSAKAQASDLEKIHL 288
```

FIG. 13

```
HTLV-I gagp19   45  QLKKFLKIALET 56                                                                    42%
                        ||||:|:
TAL-H           17  QLKQFTTVVADT 28

HTLV-I gag p24 230  .....QANNPQQQGLRREYQQLQLWLAAFAAALPGSAKDPSWASILQGLEEPY 274
                                        :   :    ::|   :|
TAL-H           30  DFHAIDEYKPQDATTNPS...LILAA.AQMPA............YQELVEEA 65

276  HAFVERLNIALDNGLPEGTPK......DPILRSLAYSNANKECQKLL... 316
                         :  :  ::      :       ::| :    :
                66  IAYGRKLGGSQEDQIKNAIDKLFVLFGAEILKKIP.GRVSTEVDARLSFD 114

317  .QARGHTNSPLGDMLRACQTWTPKDKTKVL 344         22% (40%)
                        :  :                  :
               115  KDAMVARARRLIELYKEAG..ISKDRI... 139

FLAV  1483  YTPWAILPSVVGFWITLQYTKRGGVLWDTPSPKEYKRGDTTTGVYRIMTRGLLGSYQAGA 1543   30%
                |      |                       |       ||  |     |  |
TAL-H    3  SSPVKRQRMESALDQLKQFTTVVADTGDFHAIDEYKPQDATTNPSLILAAAQMPAYQELV 62

HIV p17 97  TKEALDKIEEEQNKSKKAQQAAADTGHSNQVSQNYPIVQNIQGQMVHQAISPRTLNAWV 156   18%
```

FIG. 14A

```
TAL-H     90 LFGAEILKKIPGRVSTEVDARLSFDKDAMVAR-ARRLIELYKEAGISKDRILIKLSSTWE----GIQAG
DENGUE   765 LYLGVVVQADMGCVINWKGKELKCGSGIFVTNEVHTWTEQYKFQADSPKRVATAIAGAWENGVCGIRST

QAGKELEEQHGIHCNMTLLFSFAQAVACAEAGVTLISPFVGRILDWHVANTDKKSYEPWKTWVKSVTKIY 220
 RSTTRMENLLWKQIANELNYILWENDIKLTVVVGDITGVLEQGKRTLTPQPMELKY-SWKTWGLAKIVTA 899   18%

TAL-H  164 CNMTLLFSFAQAVACAEAGVTLISPFVGRILDWHVANTDKKSYEPLDEPGVKSVTKIY  220
HOCV  1280 CVPTLLMVFTMWADILTLILILPTYELTKLYYLKEVKIGAERGWLWKTN.YKRVNDIY 1336   18%

HTLV-I g24   299 LRSLAYSNANKECQKLLQARGHTNSPLGDMLRACQTWTPKDKTKVL  344   24%
TAL-H        243 IKALAGCDFLTISPKLLGELLQDNAKLVPVLSAKAAQASDLEKIHL  288
Polio CP2B  1052 IIELTGMVTSTITEKLLKNLIKIVSSLVIITRNYDDTTTVLATLAL 1097   29%

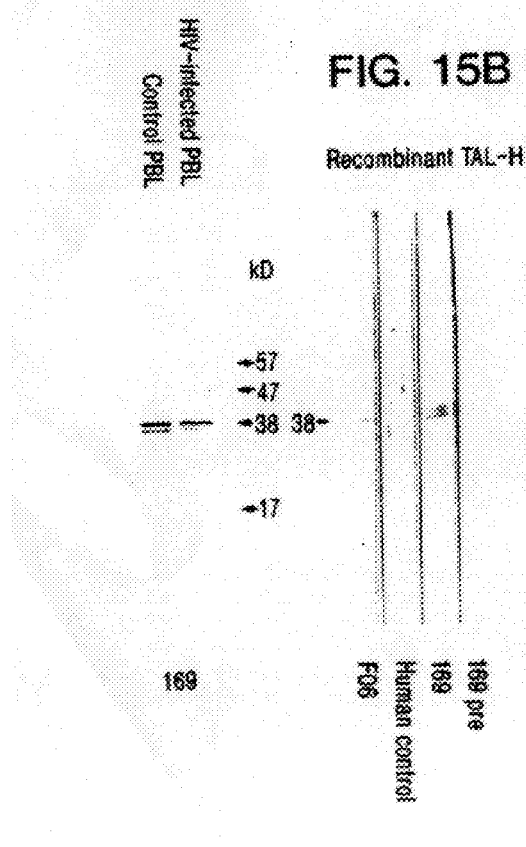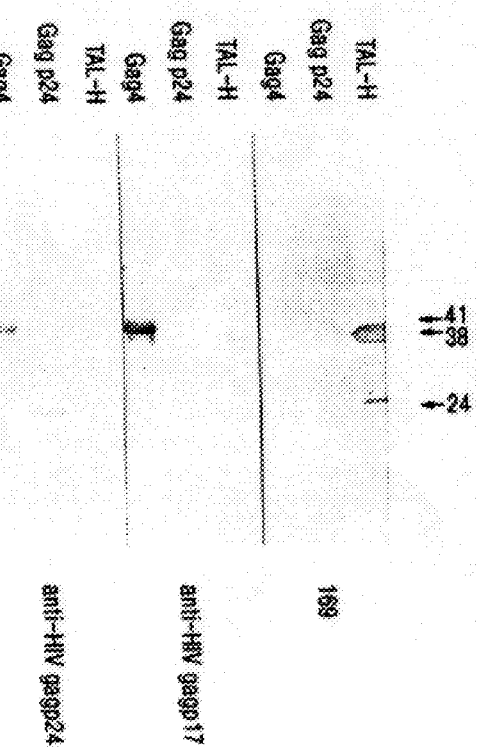

TAL-H Promoter

```
  1  TCGACTCCCT GTGATTTCAT CCCTACGGAC CAGTCAGCAC TTCTGACTCA
 51  CTCACTGGCC CCCTACCCAC CAAATTATTC TTAAATACTG GGATCCCCGA
101  GTTTTGGGGA GACTGATTTG AGGAATAAAA CTCTGGTCTC CCGAACAATC
151  GGCTCTGTGT GAATAATGCT TTCTTCTATT GCAATTCCCC TGTCTTGACA
201  ATAGACTCTG TCCCCGGCAG CTGGCAAGGC GAACCCATGG GGCCGGTTAC
251  AGTGTCTGCC AACCGGCCAA AAGGCCGACA CAGAGACATT GTACAGCAAT
301  ATACACGGGA GTAGGGACAT GTAGAGCGAG GTACAGGAGA CCGGGCTCGT
351  GCAGAGCACA GCTCTGAGGT GGTGACACCC GCAGGGTCCC CCGCCGCTCC
401  CTCCCCATGC TTCCTGCAGC GGCCCCGAC  CCCAGTCCTG GCCCCACCAT
451  GGATCCTGCA TCGCCGGGTT CGGCCTGGGG GTTCAGCCCC GCAGAGTCGG
501  CTCCCGGGCC AGGTCCATCT CCTCCAGCCT CCCGGTCGGT CCGCGGGGCA
551  GGAAGAAGCG AGCCCAGCCG CCCCGTGTCG TGCAGGTGTT TTCCCGGGCC
601  GTCGCGGCGG CTGCCTGAGG ACCTGGGGAG ACCCAGCCTG TAGGATCCGC
651  AGCTGCGGTG CGCGGCCGGC AGTGGCGCTC GGGCTTCGTC CCCGGGGGCG
701  GGGCTTCGTC CAAGGCGCGC AGGGACCAGC GGGCCTCGCC CTCCCGCGCC
751  GCTTTCCGAT TGGCAGCCGC CTGCACTGCA GGCATTGTGG GCCGTCCGCG
801  ACGCCCGTCC CGTCGCCGCC GCCGCCGCCG CAGACCCCTC GGTCTTGCTA
851  TGTCGA
```

FIG. 18

TARE-6

```
   1  ACGCCATCGA CGAGTACAAG CCCCAGGATG CTACCACCAA CCCGTCCCTG
  51  ATCCTGGCCG CAGCACAGAT GCCCGCTTAC CAGGAGCTGG TGGAGGAGGC
                                 SD
 101  GATTGCCTAT GGCCGGAAGC TGGGCGGgtg agtgcctgga ctcgggaggg
 151  tccagctagg cctcgtgct agtctagttg gccttgcttc cctccctaac
 201  tgaattttag gttctcaaac accatgaact caagggggga aaaaacccct
 251  atcttttttgc ctatttttgt ttattgaagt gtaatctgca tgaagtaacc
 301  tgcacctgtg gtaaatgagc agttcagaga gttttgccaa tgtgtgtacc
 351  ctgtaaatac cacccccagtc aagatgcaga gcacttgcag accccacag
                 TARE-2/SD
 401  gcccctcctc ccctcctgta gtcagtctcc ccagctctgg taacacttac
                                              TARE-3/SD
 451  cttctggctg tcattttatt ttttactttt cagacggagt ctcgctgtgt
 501  cacccaggct ggagtatagt ggagcaatct tggctcacta caacttccgc
 551  ctccctggtg caagcaattc tcctgcctca gcttcccaat tagctgggct
 601  tacaggtgtg tgccaccact cctggctgca ttttgtattt tttttttttg
                              TARE-4/SD
 651  agacagagtt tgcttttgtt gtccaggctg gatggcactg gcacaatctc
 701  ggctcaccgc aacctctgcc tccagattc aagcgattct cctgcctcag
                                    TARE-5/SD
 751  cctccctagt gactgggact acaggcaccc gccaccatgc ccagctaatt
                                                      pol
 801  tttaatattt ttagtggaga cggggtttca ctgtgttagc caggatggtc
      III B
 851  ttgatctcct gacctcatga tccgcccacc tcggcctccc aaagtgctgg
                   polIII A
 901  gattacaggc gtgagccacc gcacctggcg aacctcagaa gcttctaacc
                                            SA
 951  tgcttttttc cctttgaatt tcagGTCACA AGAGGACCAG ATTAAAAATG
1001  CTATTGATAA ACTTTTTGTG TTGTTTGGAG CAGAAATACT AAAGAAGATT
1051  CCGGGCCGAG TATCCACAGA AGTAGACGCA AGG
```

FIG. 19

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
    (A) LENGTH: 1332 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 57..1064

(xi) SEQUENCE DESCRIPTION: SEQ ID NO:1:

```
GAATTCCGCG  CCCGTCCGT  CGCCGCCGCC  GCCGCCGCAG  ACCCCTCGGT  CTTGCT                          56

ATG  TCG  AGC  TCA  CCC  GTG  AAG  CGT  CAG  AGG  ATG  GAG  TCC  GCG  CTG  GAC            104
Met  Ser  Ser  Ser  Pro  Val  Lys  Arg  Gln  Arg  Met  Glu  Ser  Ala  Leu  Asp
 1              5                        10                       15

CAG  CTC  AAG  CAG  TTC  ACC  ACC  GTG  GTG  GCC  GAC  ACG  GGC  GAC  TTC  CAC            152
Gln  Leu  Lys  Gln  Phe  Thr  Thr  Val  Val  Ala  Asp  Thr  Gly  Asp  Phe  His
          20                       25                       30

GCC  ATC  GAC  GAG  TAC  AAG  CCC  CAG  GAT  GCT  ACC  ACC  AAC  CCG  TCC  CTG            200
Ala  Ile  Asp  Glu  Tyr  Lys  Pro  Gln  Asp  Ala  Thr  Thr  Asn  Pro  Ser  Leu
               35                       40                       45

ATC  CTG  GCC  GCA  GCA  CAG  ATG  CCC  GCT  TAC  CAG  GAG  CTG  GTG  GAG  GAG            248
Ile  Leu  Ala  Ala  Ala  Gln  Met  Pro  Ala  Tyr  Gln  Glu  Leu  Val  Glu  Glu
     50                       55                       60

GCG  ATT  GCC  TAT  GGC  CGG  AAG  CTG  GGC  GGG  TCA  CAA  GAG  GAC  CAG  ATT            296
Ala  Ile  Ala  Tyr  Gly  Arg  Lys  Leu  Gly  Gly  Ser  Gln  Glu  Asp  Gln  Ile
 65                       70                       75                       80

AAA  AAT  GCT  ATT  GAT  AAA  CTT  TTT  GTG  TTG  TTT  GGA  GCA  GAA  ATA  CTA            344
Lys  Asn  Ala  Ile  Asp  Lys  Leu  Phe  Val  Leu  Phe  Gly  Ala  Glu  Ile  Leu
                    85                       90                       95

AAG  AAG  ATT  CCG  GGC  CGA  GTA  TCC  ACA  GAA  GTA  GAC  GCA  AGG  CTC  TCC            392
Lys  Lys  Ile  Pro  Gly  Arg  Val  Ser  Thr  Glu  Val  Asp  Ala  Arg  Leu  Ser
               100                      105                      110

TTT  GAT  AAA  GAT  GCG  ATG  GTG  GCC  AGA  GCC  AGG  CGG  CTC  ATC  GAG  CTC            440
Phe  Asp  Lys  Asp  Ala  Met  Val  Ala  Arg  Ala  Arg  Arg  Leu  Ile  Glu  Leu
          115                      120                      125

TAC  AAG  GAA  GCT  GGG  ATC  AGC  AAG  GAC  CGA  ATT  CTT  ATA  AAG  CTG  TCA            488
Tyr  Lys  Glu  Ala  Gly  Ile  Ser  Lys  Asp  Arg  Ile  Leu  Ile  Lys  Leu  Ser
     130                      135                      140

TCA  ACC  TGG  GAA  GGA  ATT  CAG  GCT  GGA  AAG  GAG  CTC  GAG  GAG  CAG  CAC            536
Ser  Thr  Trp  Glu  Gly  Ile  Gln  Ala  Gly  Lys  Glu  Leu  Glu  Glu  Gln  His
145                      150                      155                      160

GGC  ATC  CAC  TGC  AAC  ATG  ACG  TTA  CTC  TTC  TCC  TTC  GCC  CAG  GCT  GTG            584
Gly  Ile  His  Cys  Asn  Met  Thr  Leu  Leu  Phe  Ser  Phe  Ala  Gln  Ala  Val
                    165                      170                      175

GCC  TGT  GCC  GAG  GCG  GGT  GTG  ACC  CTC  ATC  TCC  CCA  TTT  GTT  GGG  CGC            632
Ala  Cys  Ala  Glu  Ala  Gly  Val  Thr  Leu  Ile  Ser  Pro  Phe  Val  Gly  Arg
               180                      185                      190

ATC  CTT  GAT  TGG  CAT  GTG  GCA  AAC  ACC  GAC  AAG  AAA  TCC  TAT  GAG  CCC            680
Ile  Leu  Asp  Trp  His  Val  Ala  Asn  Thr  Asp  Lys  Lys  Ser  Tyr  Glu  Pro
          195                      200                      205

CTG  GAA  GAC  CCT  GGG  GTA  AAG  AGT  GTC  ACT  AAA  ATC  TAC  AAC  TAC  TAC            728
Leu  Glu  Asp  Pro  Gly  Val  Lys  Ser  Val  Thr  Lys  Ile  Tyr  Asn  Tyr  Tyr
     210                      215                      220
```

| | | | | | | | | | | | | | | | | |
|---|---|---|---|---|---|---|---|---|---|---|---|---|---|---|---|---|
| AAG | AAG | TTT | AGC | TAC | AAA | ACC | ATT | GTC | ATG | GGC | GCC | TCC | TTC | CGC | AAC | 776 |
| Lys | Lys | Phe | Ser | Tyr | Lys | Thr | Ile | Val | Met | Gly | Ala | Ser | Phe | Arg | Asn | |
| 225 | | | | 230 | | | | | 235 | | | | | | 240 | |
| ACG | GGC | GAG | ATC | AAA | GCA | CTG | GCC | GGC | TGT | GAC | TTC | CTC | ACC | ATC | TCA | 824 |
| Thr | Gly | Glu | Ile | Lys | Ala | Leu | Ala | Gly | Cys | Asp | Phe | Leu | Thr | Ile | Ser | |
| | | | | 245 | | | | | 250 | | | | | 255 | | |
| CCC | AAG | CTC | CTG | GGA | GAG | CTG | CTG | CAG | GAC | AAC | GCC | AAG | CTG | GTG | CCT | 872 |
| Pro | Lys | Leu | Leu | Gly | Glu | Leu | Leu | Gln | Asp | Asn | Ala | Lys | Leu | Val | Pro | |
| | | | 260 | | | | | 265 | | | | 270 | | | | |
| GTG | CTC | TCA | GCC | AAG | GCG | GCC | CAA | GCC | AGT | GAC | CTG | GAA | AAA | ATC | CAC | 920 |
| Val | Leu | Ser | Ala | Lys | Ala | Ala | Gln | Ala | Ser | Asp | Leu | Glu | Lys | Ile | His | |
| | | 275 | | | | | 280 | | | | | 285 | | | | |
| CTG | GAT | GAG | AAG | TCT | TTC | CGT | TGG | TTG | CAC | AAC | GAG | GAC | CAG | ATG | GCT | 968 |
| Leu | Asp | Glu | Lys | Ser | Phe | Arg | Trp | Leu | His | Asn | Glu | Asp | Gln | Met | Ala | |
| | 290 | | | | | 295 | | | | | 300 | | | | | |
| GTG | GAG | AAG | CTC | TCT | GAC | GGG | ATC | CGC | AAG | TTT | GCC | GCT | GAT | GCA | GTG | 1016 |
| Val | Glu | Lys | Leu | Ser | Asp | Gly | Ile | Arg | Lys | Phe | Ala | Ala | Asp | Ala | Val | |
| 305 | | | | | 310 | | | | | 315 | | | | | 320 | |
| AAG | CTG | GAG | CGG | ATG | CTG | ACA | GAA | CGA | ATG | TTC | AAT | GCA | GAG | AAT | GGA | 1064 |
| Lys | Leu | Glu | Arg | Met | Leu | Thr | Glu | Arg | Met | Phe | Asn | Ala | Glu | Asn | Gly | |
| | | | | 325 | | | | 330 | | | | | | 335 | | |

AAG TAGCGCATCC CTGAGGCTGG ACTCCAGATC TGCACCGCCG GCCAGCTGGG    1117
Lys

ATCTGACTGC ACGTGGCTTC TGATGAATCT TGCGTTTTTT ACAAATTGGA GCAGGGACAG    1177

ATCATAGATT TCTGATTTTA TGTAAAATTT TGCCTAATAC ATTAAAGCAG TCACTTTTCC    1237

TGTGCTGTTT CAAAAAAAAA AAAAAAAAAA AAAAAAAAAA AAAAAAAAAA AAAAAAAAAA    1297

AAAAAAAAAA AAAAAAAAAA AAAAAAAGG AATTC    1332

(2) INFORMATION FOR SEQ ID NO:2:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Ser | Ser | Ser | Pro | Val | Lys | Arg | Gln | Arg | Met | Glu | Ser | Ala | Leu | Asp |
| 1 | | | | 5 | | | | | 10 | | | | | 15 | |
| Gln | Leu | Lys | Gln | Phe | Thr | Thr | Val | Val | Ala | Asp | Thr | Gly | Asp | Phe | His |
| | | | 20 | | | | | 25 | | | | | 30 | | |
| Ala | Ile | Asp | Glu | Tyr | Lys | Pro | Gln | Asp | Ala | Thr | Thr | Asn | Pro | Ser | Leu |
| | | | 35 | | | | 40 | | | | | 45 | | | |
| Ile | Leu | Ala | Ala | Ala | Gln | Met | Pro | Ala | Tyr | Gln | Glu | Leu | Val | Glu | Glu |
| | 50 | | | | | 55 | | | | | 60 | | | | |
| Ala | Ile | Ala | Tyr | Gly | Arg | Lys | Leu | Gly | Gly | Ser | Gln | Glu | Asp | Gln | Ile |
| 65 | | | | | 70 | | | | | 75 | | | | | 80 |
| Lys | Asn | Ala | Ile | Asp | Lys | Leu | Phe | Val | Leu | Phe | Gly | Ala | Glu | Ile | Leu |
| | | | | 85 | | | | | 90 | | | | | 95 | |
| Lys | Lys | Ile | Pro | Gly | Arg | Val | Ser | Thr | Glu | Val | Asp | Ala | Arg | Leu | Ser |
| | | | 100 | | | | | 105 | | | | | 110 | | |
| Phe | Asp | Lys | Asp | Ala | Met | Val | Ala | Arg | Ala | Arg | Arg | Leu | Ile | Glu | Leu |
| | | 115 | | | | | 120 | | | | | 125 | | | |
| Tyr | Lys | Glu | Ala | Gly | Ile | Ser | Lys | Asp | Arg | Ile | Leu | Ile | Lys | Leu | Ser |
| | 130 | | | | | 135 | | | | | 140 | | | | |
| Ser | Thr | Trp | Glu | Gly | Ile | Gln | Ala | Gly | Lys | Glu | Leu | Glu | Glu | Gln | His |
| 145 | | | | | 150 | | | | | 155 | | | | | 160 |

| Gly | Ile | His | Cys | Asn | Met | Thr | Leu | Leu | Phe | Ser | Phe | Ala | Gln | Ala | Val |
|-----|-----|-----|-----|-----|-----|-----|-----|-----|-----|-----|-----|-----|-----|-----|-----|
|     |     |     |     | 165 |     |     |     | 170 |     |     |     |     |     | 175 |     |
| Ala | Cys | Ala | Glu | Ala | Gly | Val | Thr | Leu | Ile | Ser | Pro | Phe | Val | Gly | Arg |
|     |     |     | 180 |     |     |     |     | 185 |     |     |     |     | 190 |     |     |
| Ile | Leu | Asp | Trp | His | Val | Ala | Asn | Thr | Asp | Lys | Lys | Ser | Tyr | Glu | Pro |
|     |     | 195 |     |     |     |     | 200 |     |     |     |     | 205 |     |     |     |
| Leu | Glu | Asp | Pro | Gly | Val | Lys | Ser | Val | Thr | Lys | Ile | Tyr | Asn | Tyr | Tyr |
|     | 210 |     |     |     |     | 215 |     |     |     |     | 220 |     |     |     |     |
| Lys | Lys | Phe | Ser | Tyr | Lys | Thr | Ile | Val | Met | Gly | Ala | Ser | Phe | Arg | Asn |
| 225 |     |     |     |     | 230 |     |     |     |     | 235 |     |     |     |     | 240 |
| Thr | Gly | Glu | Ile | Lys | Ala | Leu | Ala | Gly | Cys | Asp | Phe | Leu | Thr | Ile | Ser |
|     |     |     |     | 245 |     |     |     |     | 250 |     |     |     |     | 255 |     |
| Pro | Lys | Leu | Leu | Gly | Glu | Leu | Leu | Gln | Asp | Asn | Ala | Lys | Leu | Val | Pro |
|     |     |     |     | 260 |     |     |     |     | 265 |     |     |     |     | 270 |     |
| Val | Leu | Ser | Ala | Lys | Ala | Ala | Gln | Ala | Ser | Asp | Leu | Glu | Lys | Ile | His |
|     |     | 275 |     |     |     |     |     | 280 |     |     |     |     | 285 |     |     |
| Leu | Asp | Glu | Lys | Ser | Phe | Arg | Trp | Leu | His | Asn | Glu | Asp | Gln | Met | Ala |
|     | 290 |     |     |     |     | 295 |     |     |     |     | 300 |     |     |     |     |
| Val | Glu | Lys | Leu | Ser | Asp | Gly | Ile | Arg | Lys | Phe | Ala | Ala | Asp | Ala | Val |
| 305 |     |     |     |     | 310 |     |     |     |     | 315 |     |     |     |     | 320 |
| Lys | Leu | Glu | Arg | Met | Leu | Thr | Glu | Arg | Met | Phe | Asn | Ala | Glu | Asn | Gly |
|     |     |     |     | 325 |     |     |     |     | 330 |     |     |     |     | 335 |     |

Lys ( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CCCGTCCCGT CCCGCGCCAC CGCCGCCGTC ATCCCC    36

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ATGCCAAAAA TTACTACAGG CCCGAGGA    28

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCAGGCCCGG CCCCGCGCCA CCGACGCCCC CCGCGGCCC    39

( 2 ) INFORMATION FOR SEQ ID NO:6:

( i ) SEQUENCE CHARACTERISTICS:
        ( A ) LENGTH: 24 base pairs ( B ) TYPE: nucleic acid
( C ) STRANDEDNESS: single
( D ) TOPOLOGY: linear ( x i ) SEQUENCE DESCRIPTION: SEQ ID NO:6:

GTTACGATGG AGGCCAGAAC TTGG 24

( 2 ) INFORMATION FOR SEQ ID NO:7:

( i ) SEQUENCE CHARACTERISTICS:
( A ) LENGTH: 335 amino acids
( B ) TYPE: amino acid
( C ) STRANDEDNESS: single
( D ) TOPOLOGY: linear ( x i ) SEQUENCE DESCRIPTION: SEQ ID NO:7:

| Met | Ser | Glu | Pro | Ala | Gln | Lys | Lys | Gln | Lys | Val | Ala | Asn | Asn | Ser | Leu |
|---|---|---|---|---|---|---|---|---|---|---|---|---|---|---|---|
| 1 | | | | 5 | | | | | 10 | | | | | 15 | |
| Glu | Gln | Leu | Lys | Ala | Ser | Gly | Thr | Val | Val | Val | Ala | Asp | Thr | Gly | Asp |
| | | | 20 | | | | 25 | | | | | 30 | | | |
| Phe | Gly | Ser | Ile | Ala | Lys | Phe | Gln | Pro | Gln | Asp | Ser | Thr | Thr | Asn | Pro |
| | | 35 | | | | 40 | | | | | 45 | | | | |
| Ser | Leu | Ile | Leu | Ala | Ala | Ala | Lys | Gln | Pro | Thr | Tyr | Ala | Lys | Leu | Ile |
| | 50 | | | | 55 | | | | | 60 | | | | | |
| Asp | Val | Ala | Val | Glu | Tyr | Gly | Lys | Lys | His | Gly | Lys | Thr | Thr | Glu | Glu |
| 65 | | | | | 70 | | | | | 75 | | | | | 80 |
| Gln | Val | Glu | Asn | Ala | Val | Asp | Arg | Leu | Leu | Val | Glu | Phe | Gly | Lys | Glu |
| | | | | 85 | | | | | 90 | | | | | 95 | |
| Ile | Leu | Lys | Ile | Val | Pro | Gly | Arg | Val | Ser | Thr | Glu | Val | Asp | Ala | Arg |
| | | | 100 | | | | | 105 | | | | | 110 | | |
| Leu | Ser | Phe | Asp | Thr | Gln | Ala | Thr | Ile | Glu | Lys | Ala | Arg | His | Ile | Ile |
| | | 115 | | | | | 120 | | | | | 125 | | | |
| Lys | Leu | Phe | Glu | Gln | Glu | Gly | Val | Ser | Lys | Glu | Arg | Val | Leu | Ile | Lys |
| | 130 | | | | | 135 | | | | | 140 | | | | |
| Ile | Ala | Ser | Thr | Trp | Glu | Gly | Ile | Gln | Ala | Ala | Lys | Glu | Leu | Glu | Glu |
| 145 | | | | | 150 | | | | | 155 | | | | | 160 |
| Lys | Asp | Gly | Ile | His | Cys | Asn | Leu | Thr | Leu | Leu | Phe | Ser | Phe | Val | Gln |
| | | | | 165 | | | | | 170 | | | | | 175 | |
| Ala | Val | Ala | Cys | Ala | Glu | Ala | Gln | Val | Thr | Leu | Ile | Ser | Pro | Phe | Val |
| | | | 180 | | | | | 185 | | | | | 190 | | |
| Gly | Arg | Ile | Leu | Asp | Trp | Tyr | Lys | Ser | Ser | Thr | Gly | Lys | Asp | Tyr | Lys |
| | | 195 | | | | | 200 | | | | | 205 | | | |
| Gly | Glu | Ala | Asp | Pro | Gly | Val | Ile | Ser | Val | Lys | Lys | Met | Tyr | Asn | Tyr |
| | 210 | | | | | 215 | | | | | 220 | | | | |
| Tyr | Lys | Lys | Tyr | Gly | Tyr | Lys | Thr | Ile | Val | Met | Gly | Ala | Ser | Phe | Arg |
| 225 | | | | | 230 | | | | | 235 | | | | | 240 |
| Ser | Thr | Asp | Glu | Ile | Lys | Asn | Leu | Ala | Gly | Val | Asp | Tyr | Leu | Thr | Ile |
| | | | | 245 | | | | | 250 | | | | | 255 | |
| Ser | Pro | Ala | Leu | Leu | Asp | Lys | Leu | Met | Asn | Ser | Thr | Glu | Pro | Phe | Pro |
| | | | 260 | | | | | 265 | | | | | 270 | | |
| Arg | Val | Leu | Asp | Pro | Val | Ser | Ala | Lys | Lys | Glu | Ala | Gly | Asp | Lys | Ile |
| | | 275 | | | | | 280 | | | | | 285 | | | |
| Ser | Tyr | Ile | Ser | Asp | Glu | Ser | Lys | Phe | Arg | Phe | Asp | Leu | Asn | Glu | Asp |
| | 290 | | | | | 295 | | | | | 300 | | | | |
| Ala | Met | Ala | Thr | Glu | Lys | Leu | Ser | Glu | Gly | Ile | Arg | Lys | Phe | Ser | Ala |
| 305 | | | | | 310 | | | | | 315 | | | | | 320 |

Asp Ile Val Thr Leu Phe Asp Leu Ile Glu Lys Lys Val Thr Ala
                    325                 330                 335

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:8:

Gln Leu Lys Lys Phe Leu Lys Ile Ala Leu Glu Thr
1               5                   10

(2) INFORMATION FOR SEQ ID NO:9:

(i) SEQUENCE CHARACTERISTICS:
        (A) LENGTH: 115 amino acids
        (B) TYPE: amino acid
        (C) STRANDEDNESS: single
        (D) TOPOLOGY: linear (xi) SEQUENCE DESCRIPTION: SEQ ID NO:9:

Gln Ala Asn Asn Pro Gln Gln Gln Gly Leu Arg Arg Glu Tyr Gln Gln
1               5                   10                  15

Leu Trp Leu Ala Ala Phe Ala Ala Leu Pro Gly Ser Ala Lys Asp Pro
                20                  25                  30

Ser Trp Ala Ser Ile Leu Gln Gly Leu Glu Glu Pro Tyr His Ala Phe
            35                  40                  45

Val Glu Arg Leu Asn Ile Ala Leu Asp Asn Gly Leu Pro Glu Gly Thr
        50                  55                  60

Pro Lys Asp Pro Ile Leu Arg Ser Leu Ala Tyr Ser Asn Ala Asn Lys
65                  70                  75                  80

Glu Cys Gln Lys Leu Leu Gln Ala Arg Gly His Thr Asn Ser Pro Leu
                85                  90                  95

Gly Asp Met Leu Arg Ala Cys Gln Thr Trp Thr Pro Lys Asp Lys Thr
                100                 105                 110

Lys Val Leu
        115

(2) INFORMATION FOR SEQ ID NO:10:

(i) SEQUENCE CHARACTERISTICS:
        (A) LENGTH: 51 amino acids
        (B) TYPE: amino acid
        (C) STRANDEDNESS: single
        (D) TOPOLOGY: linear (xi) SEQUENCE DESCRIPTION: SEQ ID NO:10:

Glu Glu Gln Asn Lys Ser Lys Lys Lys Ala Gln Gln Ala Ala Ala Asp
1               5                   10                  15

Thr Gly His Ser Asn Gln Val Ser Gln Asn Tyr Pro Ile Val Gln Asn
                20                  25                  30

Ile Gln Gly Gln Met Val His Gln Ala Ile Ser Pro Arg Thr Leu Asn
            35                  40                  45

Ala Trp Val
        50

(2) INFORMATION FOR SEQ ID NO:11:

(i) SEQUENCE CHARACTERISTICS:
        (A) LENGTH: 60 amino acids (B) TYPE: amino acid
(C) STRANDEDNESS: single
(D) TOPOLOGY: linear (xi) SEQUENCE DESCRIPTION: SEQ ID NO:11:

| Thr | Lys | Glu | Ala | Leu | Asp | Lys | Ile | Glu | Glu | Glu | Gln | Asn | Lys | Ser | Lys |
|---|---|---|---|---|---|---|---|---|---|---|---|---|---|---|---|
| 1 | | | | 5 | | | | | 10 | | | | | 15 | |
| Lys | Lys | Ala | Gln | Gln | Ala | Ala | Ala | Asp | Thr | Gly | His | Ser | Asn | Gln | Val |
| | | | 20 | | | | | 25 | | | | | 30 | | |
| Ser | Gln | Asn | Tyr | Pro | Ile | Val | Gln | Asn | Ile | Gln | Gly | Gln | Met | Val | His |
| | | 35 | | | | | 40 | | | | | 45 | | | |
| Gln | Ala | Ile | Ser | Pro | Arg | Thr | Leu | Asn | Ala | Trp | Val | | | | |
| | 50 | | | | | 55 | | | | | 60 | | | | |

(2) INFORMATION FOR SEQ ID NO:12:

(i) SEQUENCE CHARACTERISTICS:
(A) LENGTH: 60 amino acids
(B) TYPE: amino acid
(C) STRANDEDNESS: single
(D) TOPOLOGY: linear (xi) SEQUENCE DESCRIPTION: SEQ ID NO:12:

| Tyr | Thr | Pro | Trp | Ala | Ile | Leu | Pro | Ser | Val | Val | Gly | Phe | Trp | Ile | Thr |
|---|---|---|---|---|---|---|---|---|---|---|---|---|---|---|---|
| 1 | | | | 5 | | | | | 10 | | | | | 15 | |
| Leu | Gln | Tyr | Thr | Lys | Arg | Gly | Gly | Val | Leu | Trp | Asp | Thr | Pro | Ser | Pro |
| | | | 20 | | | | | 25 | | | | | 30 | | |
| Lys | Glu | Tyr | Lys | Arg | Gly | Asp | Thr | Thr | Gly | Val | Tyr | Arg | Ile | Met |
| | | | 35 | | | | | 40 | | | | | 45 | | |
| Thr | Arg | Gly | Leu | Leu | Gly | Ser | Tyr | Gln | Ala | Gly | Ala | | | | |
| | 50 | | | | | 55 | | | | | 60 | | | | |

(2) INFORMATION FOR SEQ ID NO:13:

(i) SEQUENCE CHARACTERISTICS:
(A) LENGTH: 138 amino acids
(B) TYPE: amino acid
(C) STRANDEDNESS: single
(D) TOPOLOGY: linear (xi) SEQUENCE DESCRIPTION: SEQ ID NO:13:

| Leu | Tyr | Leu | Gly | Val | Val | Val | Gln | Ala | Asp | Met | Gly | Cys | Val | Ile | Asn |
|---|---|---|---|---|---|---|---|---|---|---|---|---|---|---|---|
| 1 | | | | 5 | | | | | 10 | | | | | 15 | |
| Trp | Lys | Gly | Lys | Glu | Leu | Lys | Cys | Gly | Ser | Gly | Ile | Phe | Val | Thr | Asn |
| | | | 20 | | | | | 25 | | | | | 30 | | |
| Glu | Val | His | Thr | Trp | Thr | Glu | Gln | Tyr | Lys | Phe | Gln | Ala | Asp | Ser | Pro |
| | | | 35 | | | | | 40 | | | | | 45 | | |
| Lys | Arg | Val | Ala | Thr | Ala | Ile | Ala | Gly | Ala | Trp | Glu | Asn | Gly | Val | Cys |
| | | 50 | | | | | 55 | | | | | 60 | | | |
| Gly | Ile | Arg | Ser | Thr | Arg | Ser | Thr | Thr | Arg | Met | Glu | Asn | Leu | Leu | Trp |
| 65 | | | | | 70 | | | | | 75 | | | | | 80 |
| Lys | Gln | Ile | Ala | Asn | Glu | Leu | Asn | Tyr | Ile | Leu | Trp | Glu | Asn | Asp | Ile |
| | | | | 85 | | | | | 90 | | | | | 95 | |
| Lys | Leu | Thr | Val | Val | Val | Gly | Asp | Ile | Thr | Gly | Val | Leu | Glu | Gln | Gly |
| | | | 100 | | | | | 105 | | | | | 110 | | |
| Lys | Arg | Thr | Leu | Thr | Pro | Gln | Pro | Met | Glu | Leu | Lys | Tyr | Ser | Trp | Lys |
| | | | 115 | | | | | 120 | | | | | 125 | | |
| Thr | Trp | Gly | Leu | Ala | Lys | Ile | Val | Thr | Ala | | | | | | |
| | | 130 | | | | | 135 | | | | | | | | |

(2) INFORMATION FOR SEQ ID NO:14:

(i) SEQUENCE CHARACTERISTICS:
        (A) LENGTH: 57 amino acids
        (B) TYPE: amino acid
        (C) STRANDEDNESS: single
        (D) TOPOLOGY: linear (xi) SEQUENCE DESCRIPTION: SEQ ID NO:14:

```
Cys Val Pro Thr Leu Leu Met Val Phe Thr Met Trp Ala Asp Ile Leu
 1               5                  10                  15

Thr Leu Ile Leu Ile Leu Pro Thr Tyr Glu Leu Thr Lys Leu Tyr Tyr
            20                  25                  30

Leu Lys Glu Val Lys Ile Gly Ala Glu Arg Gly Trp Leu Trp Lys Thr
        35                  40                  45

Asn Tyr Lys Arg Val Asn Asp Ile Tyr
    50                  55
```

(2) INFORMATION FOR SEQ ID NO:15:

(i) SEQUENCE CHARACTERISTICS:
        (A) LENGTH: 46 amino acids
        (B) TYPE: amino acid
        (C) STRANDEDNESS: single
        (D) TOPOLOGY: linear (xi) SEQUENCE DESCRIPTION: SEQ ID NO:15:

```
Ile Ile Glu Leu Thr Gly Met Val Thr Ser Thr Ile Thr Glu Lys Leu
 1               5                  10                  15

Leu Lys Asn Leu Ile Lys Ile Val Ser Ser Leu Val Ile Ile Thr Arg
            20                  25                  30

Asn Tyr Asp Asp Thr Thr Thr Val Leu Ala Thr Leu Ala Leu
        35                  40                  45
```

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:16:

```
Gln Leu Lys Gln Phe Thr Thr Val Val Ala Asp Thr
 1               5                  10
```

(2) INFORMATION FOR SEQ ID NO:17:

(i) SEQUENCE CHARACTERISTICS:
        (A) LENGTH: 110 amino acids
        (B) TYPE: amino acid
        (C) STRANDEDNESS: single
        (D) TOPOLOGY: linear (xi) SEQUENCE DESCRIPTION: SEQ ID NO:17:

```
Asp Phe His Ala Ile Asp Glu Tyr Lys Pro Gln Asp Ala Thr Thr Asn
 1               5                  10                  15

Pro Ser Leu Ile Leu Ala Ala Ala Gln Met Pro Ala Tyr Gln Glu Leu
            20                  25                  30

Val Glu Glu Ala Ile Ala Tyr Gly Arg Lys Leu Gly Gly Ser Gln Glu
        35                  40                  45

Asp Gln Ile Lys Asn Ala Ile Asp Lys Leu Phe Val Leu Phe Gly Ala
        50                  55                  60
```

| | | | | | | | | | | | | | | | |
|---|---|---|---|---|---|---|---|---|---|---|---|---|---|---|---|
|Glu|Ile|Leu|Lys|Lys|Ile|Pro|Gly|Arg|Val|Ser|Thr|Glu|Val|Asp|Ala|
|65| | | | |70| | | |75| | | | | |80|
|Arg|Leu|Ser|Phe|Asp|Lys|Asp|Ala|Met|Val|Ala|Arg|Ala|Arg|Arg|Leu|
| | | | |85| | | |90| | | | |95| | |
|Ile|Glu|Leu|Tyr|Lys|Glu|Ala|Gly|Ile|Ser|Lys|Asp|Arg|Ile| | |
| | | |100| | | | |105| | | | |110| | |

( 2 ) INFORMATION FOR SEQ ID NO:18:

( i ) SEQUENCE CHARACTERISTICS:
        ( A ) LENGTH: 135 amino acids
        ( B ) TYPE: amino acid
        ( C ) STRANDEDNESS: single
        ( D ) TOPOLOGY: linear ( x i ) SEQUENCE DESCRIPTION: SEQ ID NO:18:

| | | | | | | | | | | | | | | | |
|---|---|---|---|---|---|---|---|---|---|---|---|---|---|---|---|
|Leu|Phe|Gly|Ala|Glu|Ile|Leu|Lys|Lys|Ile|Pro|Gly|Arg|Val|Ser|Thr|
|1| | | |5| | | | |10| | | | |15| |
|Glu|Val|Asp|Ala|Arg|Leu|Ser|Phe|Asp|Lys|Ala|Met|Val|Ala|Arg| |
| | | |20| | | | |25| | | |30| | | |
|Ala|Arg|Arg|Leu|Ile|Glu|Leu|Tyr|Lys|Glu|Ala|Gly|Ile|Ser|Lys|Asp|
| | |35| | | | |40| | | | |45| | | |
|Arg|Ile|Leu|Ile|Lys|Leu|Ser|Ser|Thr|Trp|Glu|Gly|Ile|Gln|Ala|Gly|
| |50| | | | |55| | | | |60| | | | |
|Gln|Ala|Gly|Lys|Glu|Leu|Glu|Glu|Gln|His|Gly|Ile|His|Cys|Asn|Met|
|65| | | | |70| | | |75| | | | | |80|
|Thr|Leu|Leu|Phe|Ser|Phe|Ala|Gln|Ala|Val|Ala|Cys|Ala|Glu|Ala|Gly|
| | | | |85| | | |90| | | | |95| | |
|Val|Thr|Leu|Ile|Ser|Pro|Phe|Val|Gly|Arg|Ile|Leu|Asp|Trp|His|Val|
| | | |100| | | | |105| | | | |110| | |
|Ala|Asn|Thr|Asp|Lys|Lys|Ser|Tyr|Glu|Pro|Leu|Glu|Asp|Pro|Gly|Val|
| | | |115| | | | |120| | | | |125| | |
|Lys|Ser|Val|Thr|Lys|Ile|Tyr| | | | | | | | | |
| | |130| | | | | | | | | | | | | |

( 2 ) INFORMATION FOR SEQ ID NO:19:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

| | | | | | | | | | | | | | | | |
|---|---|---|---|---|---|---|---|---|---|---|---|---|---|---|---|
|Ser|Ser|Pro|Val|Lys|Arg|Gln|Arg|Met|Glu|Ser|Ala|Leu|Asp|Gln|Leu|
|1| | | |5| | | | |10| | | | |15| |
|Lys|Gln|Phe|Thr|Thr|Val|Val|Ala|Asp|Thr|Gly|Asp|Phe|His|Ala|Ile|
| | | |20| | | | |25| | | | |30| | |
|Asp|Glu|Tyr|Lys|Pro|Gln|Asp|Ala|Thr|Thr|Asn|Pro|Ser|Leu|Ile|Leu|
| | |35| | | | |40| | | | |45| | | |
|Ala|Ala|Ala|Gln|Met|Pro|Ala|Tyr|Gln|Glu|Leu|Val| | | | |
| | |50| | | | |55| | | | |60| | | |

( 2 ) INFORMATION FOR SEQ ID NO:20:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

```
          Glu  Ser  Ala  Leu  Asp  Gln  Leu  Lys  Gln  Phe  Thr  Thr  Val  Val  Ala  Asp
          1              5                        10                       15

Thr  Gly  Asp  Phe  His  Ala  Ile  Asp  Glu  Tyr  Lys  Pro  Gln  Asp  Ala  Thr
                         20                       25                       30

Thr  Asn  Pro  Ser  Leu  Ile  Leu  Ala  Ala  Ala  Gln  Met  Pro  Ala  Tyr  Gln
                    35                       40                       45

Glu  Leu  Val
                    50
```

( 2 ) INFORMATION FOR SEQ ID NO:21:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

```
          Ile  Lys  Ala  Leu  Ala  Gly  Cys  Asp  Phe  Leu  Thr  Ile  Ser  Pro  Lys  Leu
          1              5                        10                       15

Leu  Gly  Glu  Leu  Leu  Gln  Asp  Asn  Ala  Lys  Leu  Val  Pro  Val  Leu  Ser
                         20                       25                       30

Ala  Lys  Ala  Ala  Gln  Ala  Ser  Asp  Leu  Glu  Lys  Ile  His  Leu
                    35                       40                       45
```

( 2 ) INFORMATION FOR SEQ ID NO:22:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( x i ) SEQUENCE DESCRIPTION: SEQ ID NO:22:

```
          Cys  Asn  Met  Thr  Leu  Leu  Phe  Ser  Phe  Ala  Gln  Ala  Val  Ala  Cys  Ala
          1              5                        10                       15

Glu  Ala  Gly  Val  Thr  Leu  Ile  Ser  Pro  Phe  Val  Gly  Arg  Ile  Leu  Asp
                         20                       25                       30

Trp  His  Val  Ala  Asn  Thr  Asp  Lys  Lys  Ser  Tyr  Glu  Pro  Leu  Glu  Asp
                    35                       40                       45

Pro  Gly  Val  Lys  Ser  Val  Thr  Lys  Ile  Tyr
                    50                       55
```

( 2 ) INFORMATION FOR SEQ ID NO:23:

( i ) SEQUENCE CHARACTERISTICS:
        ( A ) LENGTH: 856 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
TCGACTCCCT  GTGATTTCAT  CCCTACGGAC  CAGTCAGCAC  TTCTGACTCA  CTCACTGGCC      60
CCCTACCCAC  CAAATTATTC  TTAAATACTG  GGATCCCCGA  GTTTTGGGGA  GACTGATTTG     120
AGGAATAAAA  CTCTGGTCTC  CCGAACAATC  GGCTCTGTGT  GAATAATGCT  TTCTTCTATT     180
GCAATTCCCC  TGTCTTGACA  ATAGACTCTG  TCCCCGGCAG  CTGGCAAGGC  GAACCCATGG     240
GGCCGGTTAC  AGTGTCTGCC  AACCGGCAA   AAGGCCGACA  CAGAGACATT  GTACAGCAAT     300
ATACACGGGA  GTAGGGACAT  GTAGAGCGAG  GTACAGGAGA  CCGGGCTCGT  GCAGAGCACA     360
GCTCTGAGGT  GGTGACACCC  GCAGGGTCCC  CCGCCGCTCC  CTCCCCATGC  TTCCTGCAGC     420
```

```
GGCCCCCGAC  CCCAGTCCTG  GCCCCACCAT  GGATCCTGCA  TCGCCGGGTT  CGGCCTGGGG      480

GTTCAGCCCC  GCAGAGTCGG  CTCCCGGGCC  AGGTCCATCT  CCTCCAGCCT  CCCGGTCGGT      540

CCGCGGGGCA  GGAAGAAGCG  AGCCCAGCCG  CCCCGTGTCG  TGCAGGTGTT  TTCCCGGGCC      600

GTCGCGGCGG  CTGCCTGAGG  ACCTGGGGAG  ACCCAGCCTG  TAGGATCCGC  AGCTGCGGTG      660

CGCGGCCGGC  AGTGGCGCTC  GGGCTTCGTC  CCCGGGGGCG  GGGCTTCGTC  CAAGGCGCGC      720

AGGGACCAGC  GGGCCTCGCC  CTCCCGCGCC  GCTTTCCGAT  TGGCAGCCGC  CTGCACTGCA      780

GGCATTGTGG  GCCGTCCGCG  ACGCCCGTCC  CGTCGCCGCC  GCCGCCGCCG  CAGACCCCTC      840

GGTCTTGCTA  TGTCGA                                                          856
```

( 2 ) INFORMATION FOR SEQ ID NO:24:

( i ) SEQUENCE CHARACTERISTICS:
        ( A ) LENGTH: 1083 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
ACGCCATCGA  CGAGTACAAG  CCCCAGGATG  CTACCACCAA  CCCGTCCCTG  ATCCTGGCCG       60

CAGCACAGAT  GCCCGCTTAC  CAGGAGCTGG  TGGAGGAGGC  GATTGCCTAT  GGCCGGAAGC      120

TGGGCGGGTG  AGTGCCTGGA  CTCGGGAGGG  TCCAGCTAGG  CCCTCGTGCT  AGTCTAGTTG      180

GCCTTGCTTC  CCTCCCTAAC  TGAATTTTAG  GTTCTCAAAC  ACCATGAACT  CAAGGGGGA       240

AAAAAACCCT  ATCTTTTTGC  CTATTTTTGT  TTATTGAAGT  GTAATCTGCA  TGAAGTAACC      300

TGCACCTGTG  GTAAATGAGC  AGTTCAGAGA  GTTTGCCAA   TGTGTGTACC  CTGTAAATAC      360

CACCCCAGTC  AAGATGCAGA  GCACTTGCAG  ACCCCACAG   GCCCCTCCTC  CCCTCCTGTA      420

GTCAGTCTCC  CCAGCTCTGG  TAACACTTAC  CTTCTGGCTG  TCATTTATT   TTTTACTTTT      480

CAGACGGAGT  CTCGCTGTGT  CACCCAGGCT  GGAGTATAGT  GGAGCAATCT  TGGCTCACTA      540

CAACTTCCGC  CTCCCTGGTG  CAAGCAATTC  TCCTGCCTCA  GCTTCCAAT   TAGCTGGGCT      600

TACAGGTGTG  TGCCACCACT  CCTGGCTGCA  TTTTGTATTT  TTTTTTTTG   AGACAGAGTT      660

TGCTTTTGTT  GTCCAGGCTG  GATGGCACTG  GCACAATCTC  GGCTCACCGC  AACCTCTGCC      720

TCCCAGATTC  AAGCGATTCT  CCTGCCTCAG  CCTCCCTAGT  GACTGGGACT  ACAGGCACCC      780

GCCACCATGC  CCAGCTAATT  TTTAATATTT  TTAGTGGAGA  CGGGGTTTCA  CTGTGTTAGC      840

CAGGATGGTC  TTGATCTCCT  GACCTCATGA  TCCGCCCACC  TCGGCCTCCC  AAAGTGCTGG      900

GATTACAGGC  GTGAGCCACC  GCACCTGGCG  AACCTCAGAA  GCTTCTAACC  TGCTTTTTC       960

CCTTTGAATT  TCAGGTCACA  AGAGGACCAG  ATTAAAAATG  CTATTGATAA  ACTTTTTGTG     1020

TTGTTTGGAG  CAGAAATACT  AAAGAAGATT  CCGGGCCGAG  TATCCACAGA  AGTAGACGCA     1080

AGG                                                                       1083
```

HUMAN TRANSALDOLASE: AN AUTOANTIGEN WITH A FUNCTION IN METABOLISM

CROSS-REFERENCE TO RELATED APPLICATIONS

This application is a divisional of U.S. patent application Ser. No. 08/326,119, filed 19 Oct. 1994.

BACKGROUND OF THE INVENTION

Field of the Invention

The invention in the fields of medicine, molecular biology and immunology relates to human transaldolase, DNA coding therefore, and the discovery that the protein is a human autoantigen in immune-mediated demyelinating diseases such as multiple sclerosis. Therefore this invention is directed to compositions and methods useful for detecting and measuring such antibodies or the transaldolase protein or peptide antigens. The methods and composition are useful in the diagnosis of multiple sclerosis and other human immune-related neurodegenerative diseases.

Abbreviations Used
- APC: antigen-presenting cells
- HTLV-1: human T lymphotropic virus-I
- PBL: peripheral blood lymphocyte
- PBMC: peripheral blood mononuclear cells
- PPP: pentose phosphate pathway
- RTE: retrotransposable element
- TAL: transaldolase enzyme
- TAL-H: human transaldolase gene or protein
- TAL-Y: yeast transaldolase gene or protein
- TARE: transaldolase retrotransposable element

Description of the Background Art

Retrotransposable Elements

The present inventor's laboratory has been studying retrotransposable elements (RTE) and endogenous retroviral sequences for several years. RTEs are highly repetitive sequences making up as much as 10% of the eukaryotic genome (Temin, H. M. (1985) *Mol. Biol. Evol.* 2:455–468). These elements multiply through RNA intermediates by reverse transcription from RNA to DNA. The normal human genome contains a complex variety of RTEs. The viral superfamily of RTEs comprises a number of different endogenous retroviral sequences which are related to known animal or human retroviruses. While some endogenous retroviral sequences are represented in a single copy per haploid genome, others are highly repetitive and occur at a frequency of up to 1000 copies per haploid genome similar to the larger family of nonviral RTEs (Perl, A. et al. (1993) *Trends. Microbiol.* 1:153–156).

Two members of the nonviral superfamily, the short interspersed elements (90–400 bp in size) and the long interspersed elements (up to 7000 bp in size) are present in the genome in copy numbers in excess of 100,000 (Weiner, A. M. et al., (1986) *Ann. Rev. Biochem.* 55:631–61). Retrotransposition of these highly repetitive elements is considered a major factor in the shaping and reorganization of the genome (Temin, supra). The present study was initiated to identify potentially novel transcriptionally active RTEs. The data document cloning and sequencing of a so far uncharacterized highly repetitive RTE based on a limited sequence homology to the human T-cell leukemia virus (Seiki, M. et al. (1983) *Proc. Natl. Acad. Sci. USA* 80:3618–3622) and a related endogenous retroviral sequence, HRES-1 (Perl, A. et al. (1989) *Nucleic Acids Res.* 17:6841–6854). This novel RTE constitutes an integral part of the coding sequence of the human gene for transaldolase, the subject matter of the present invention, and is termed "transaldolase-associated repetitive element" (TARE).

Human Transaldolase Gene and Protein

The transaldolase enzyme (TAL), which catalyzes the transfer of a C3 fragment corresponding to dihydroxyacetone in the pentose phosphate pathway (PPP) is a pivotal enzyme in this pathway. TAL was originally described in yeast (Horecker, B. L. et al. (1953) *J. Am. Chem. Soc.* 75:2021–2022). The PPP provides D-ribose-5-phosphate for the synthesis of nucleic acids and NADPH as a reducing agent (Mayes, P. A. (1993), In: *Harper's Biochemistry*, Murray, R. K. et al. (eds), pp. 201–211, Appleton-Lange, Norwalk, Conn.). The transaldolase structural gene was recently cloned from yeast (TAL-Y; Schaaf, I. et al., (1990) *Eur. J. Biochem.* 188:597–603).

The PPP that shows maximal activity at birth and early stages of embryogenesis, coinciding with development of the nervous system at a period of active growth and myelination (Baquer, N. Z. et al., 1975, In: *Normal and Pathological Development of Energy Metabolism.* F. A. Hommes et al., eds, Academic Press, London, pp 109–132). Another fundamental function of the PPP is to maintain glutathione at a reduced state and, consequently, to protect sulfhydryl groups and cellular integrity. Thus, cellular integrity is protected from damage caused by reactive oxygen intermediates by reduced glutathione (GSH), which is solely dependent on NADPH produced uniquely by the PPP (FIG. 17). Until the discoveries which constitute the present invention, human transaldolase had never been cloned or isolated. As discovered by the present inventor, and disclosed herein, this enzyme bears a distinctive relationship with multiple sclerosis and other immune-related neurodegenerative diseases.

Multiple Sclerosis and Other Immune-Related Neurodegenerative Diseases

Although the etiology of multiple sclerosis (MS) is unknown, there is compelling evidence that its pathogenesis is mediated through the immune system. Molecular mimicry involving cross-reactivity between self-antigens and viral proteins, has been implicated in the initiation of autoimmunity in general and MS in particular. Myelin sheaths of nerves are formed by oligodendrocytes in the CNS. MS lesions are characterized by a progressive loss of oligodendrocytes and demyelination in the white matter of the central nervous system (Martin, R. et al., 1992, *Ann. Rev. Immunol.* 10:153). In the acute stage of disease, lesions contain macrophages, T cells, and immunoglobulin deposits suggesting that the demyelination process is mediated by the immune system. The inflammatory picture of early lesions followed by a progressive gliosis suggested that the pathological process may be initiated by infectious agents and then self-perpetuated by a cross-reactive autoimmune process (Fujinami, R. S. et al., 1985, *Science* 230:1043; Shaw, S. Y. et al., 1986, *FEBS Lett.* 207:266; Query, C. C. et al., 1987, *Cell* 51:211; Antel, J. P. et al., 1991, *Mayo Clin. Proc.* 66:752; Perl, A. et al., 1993, *Trends Microbiol.* 1:153; Murphy, P. M., 1993, *Cell* 72:823).

While a number of myelin-derived structural proteins have been shown to elicit MS-like disease in animal models, the antigen(s) driving this self-destructive process, which could account for pathogenesis of the human disease, has not been identified despite years of research. Studies on relapsing EAE have shown that different encephalitogenic molecules, or epitopes within them, are selected, suggesting that relapse episodes are induced by different neuroantigens (McCarron, R. M. et al., 1990, *J. Neuroimmunol.* 29:73; Whitharn, R. H. et al., 1991, *J. Immunol.* 147:3803).

Nevertheless, oxygen radicals (see FIG. 17) have been suggested to play a key role in the demyelination process. Intralesional cytotoxic T cells produce tumor necrosis factor (TNF) β which, in turn, induces apoptosis, an oxidative stress-mediated programmed cell death, of oligodendrocytes (Selmaj, K. et al., 1991, *J. Immunol.* 147:1522). Macrophages and astrocytes produce nitric oxide, which can also destroy oligodendrocytes via formation of reactive oxygen intermediates (Merrill, J. E. et al., 1993, *J. Immunol.* 151:2132)).

Involvement of the T cell receptor (TCR) in the pathogenesis of MS was suggested by over-representation of a polymorphic HindIII site in the TCR J chain locus (Seboun, E. et al., 1989, *Cell* 57:1095–1100) and skewing of TCR I-chain polymorphisms in MS patients (Oksenberg, J. R. et al., 1989, *Proc. Natl. Acad. Sci. USA* 86:988–992). Moreover, a skewed TCR VI usage in identical twins with MS points to the importance of exogenous factors in shaping both the TCR repertoire and the disease process (Utz, U. et al., 1993, *Nature* 364:243–247). Among Caucasians where MS is most prevalent, specific MHC class II alleles are associated with an increased risk of MS (Hauser, S. L. et al., 1989, *Neurology* 39:275–277; Olerup, O. et al., 1990, *Tissue Antigens* 38:1–15). These findings are consistent with the notion that certain MHC structures are better able than others to present MS antigen(s) to helper T cells and so induce disease.

To develop specific immunotherapeutic approaches to MS, investigators have characterized the TCR Vα/β and Vγ/δ repertoire in acute MS lesions, among T cells in the peripheral blood and CSF, and in T cell lines specific for the myelin basic protein (MBP) antigen (Martin et al., supra). While these authors pointed to the absence of significant overlap in TCR usage by MBP-specific T cells from peripheral blood of MS patients, other studies showed a preferential usage of TCR VJ5.2 and VJ6.1 by MBP-reactive peripheral T cells (Kotzin, B. L. et al., 1991, *Proc. Natl. Acad. Sci. USA* 88:9161–9165) and relative overexpression of TCR VJ5.2 and VJ6 in MS plaques (Oksenberg, J. R. et al., 1993, *Nature* 362:68–70), suggesting a pathogenic role for these T cells in a subset of patients. "Vaccination" of MS patients with TCR VJ peptides elicited cell- and antibody-mediated immunity in 7/11 and 2/11 patients, respectively, with no significant clinical improvement, however. Nevertheless, this study at least demonstrated the safety and immunological specificity of the TCR vaccination approach (Bourdette, D. N. et al., 1994, *J. Immunol.* 152:2510–2519; Chou, Y. K. et al., *J. Immunol.* 152:2520–2529). Animal studies indicated that different encephalitogenic molecules or epitopes within them are selected, which is compatible with the heterogeneity of the immune response in MS. Thus, in an animal model of MS, initiation and relapse may therefore be induced by different neuroantigens (McCarron), R. M. et al., *J. Neuroimmunol.* 29:73–79; Whitham, R. H. et al., 1991, *J. Immunol* 147:3803–3808).

Despite the foregoing, it appears that the ultimate human MS autoantigen has not yet been found. Once this antigen (or antigens) which drives the autoimmune and subsequent inflammatory response in human MS is identified, rationally based design of therapeutic autoantigen-mimicking or tolerogenic peptides can begin. The present invention is directed in part to solving this problem.

SUMMARY OF THE INVENTION

The present inventor has discovered human transaldolase-coding DNA and expressed the protein, produced antibodies against it, and found a connection between immunoreactivity against human transaldolase and multiple sclerosis. Furthermore, he has identified homologies between the protein and proteins of several human retroviruses may be an pathogenetic factor MS and other immune-related neurodegenerative disease. On this basis, he has conceived of compositions and methods for detecting the presence of anti-TAL-H antibodies and for diagnosing MS.

The present invention is thus directed to a human transaldolase (TAL-H) protein molecule, or a fragment or functional derivative thereof, substantially free of other proteins with which it is natively associated. TAL-H preferably has the amino acid sequence SEQ ID NO:2.

Also provided are peptide fragments of TAL-H having the amino acid sequence of residues 1–139 of SEQ ID NO:2 or residues 150–337 of SEQ ID NO:2.

In another embodiment are provided peptide fragments selected from the group consisting of SEQ ID NO:16, SEQ ID NO:17, SEQ ID NO:18, SEQ ID NO:19, SEQ ID NO:20, SEQ ID NO:21 AND SEQ ID NO:22, which peptides bear homology to retroviral amino acid sequences, in particular HTLV-I and HIV.

In one embodiment, a protein or peptide according to this invention is one characterized in that it is immunoreactive with an anti-TAL-H antibody or an anti-TAL-H T lymphocyte.

The present invention is further directed to an isolated, preferably a recombinant, DNA molecule encoding a TAL-H protein as above, or encoding a peptide thereof. Also included is an allelic variant of the DNA molecule. The DNA molecule is preferably a cDNA molecule. A preferred DNA molecule has the nucleotide sequence SEQ ID NO:1 or a portion of this sequence sufficient to encode a peptide which is a functional derivative of TAL-H.

Also provided is a recombinant DNA molecule encoding any of the above TAL-H peptides or derivatives.

The DNA molecule may be an expression vehicle, preferably a plasmid.

In another embodiment, the invention is directed to a prokaryotic host cell transformed with the above DNA molecule, or a eukaryotic host cell transfected with the DNA molecule.

The present invention is also directed to a recombinant DNA molecule which is a promoter or enhancer sequence for the DNA encoding TAL-H. This sequence may be a promoter, preferably SEQ ID NO:23, or a retrotransposable element, preferably SEQ ID NO:24 containing regulatory sequences. These sequences, or fragments thereof, may be used as expression control elements in recombinant constructs or as probes.

Also provided herein is a process for preparing a TAL-H protein or functional derivative, the process comprising:

(a) culturing a host, preferably a prokaryote, capable of expressing the protein under culturing conditions;

(b) expressing the protein; and (c) recovering the protein from the culture.

Another embodiment is directed to an antibody specific for TAL-H; such an antibody may be an intact molecule or an antigen binding fragment, a mAb, a chimeric antibody or a single chain antibody.

The invention also includes a method for detecting in a biological fluid or cell the presence of, or measuring the quantity of, a human transaldolase protein or peptide, comprising: (a) contacting the biological fluid or cell with an antibody as above; and (b) detecting the binding of the antibody to the biological fluid or cell, or measuring the quantity of antibody bound, thereby determining the presence or measuring the quantity of TAL-H.

In another embodiment, the invention provides a method for identifying, in a chemical or biological preparation, a composition, preferably an antibody, capable of binding to GAL-H or a flnctional derivative, which method comprises:

(a) attaching the transaldolase protein or derivative, or a ligand-binding portion thereof, to a solid support;

(b) contacting the chemical or biological preparation with the solid support allowing the composition to bind, and washing away any unbound material; and (c) detecting the presence of the composition bound to the solid support.

Also included is a method for isolating from a complex mixture a composition, preferably an antibody, capable of binding to TAL-H protein or derivative, comprising:

(a) attaching the TAL-H protein or functional derivative, or a ligand-binding portion thereof, to a solid support;

(b) contacting the complex mixture with the solid support allowing the composition to bind, and washing away any unbound material; and (c) eluting the bound composition, thereby isolating the composition.

The present invention is directed to a method for diagnosing the presence of a disease associated with transaldolase-specific autoimmunity, preferably a neurodegenerative disease such as multiple sclerosis, or a state of transaldolase-specific immune reactivity in a subject, comprising testing a body fluid of the subject for the presence of an antibody or a T lymphocyte which is immunologically reactive with TAL-H. The test method for an antibody is preferably an enzyme immunoassay with the TAL-H protein or derivative as antigen. The T cell testing method is preferably a lymphocyte proliferation assay.

The invention also provides a method for diagnosing the presence or development of a disease associated with transaldolase-specific autoimmunity in a subject, preferably a neurodegenerative disease or MS, comprising testing a tissue sample from the subject for the presence of tissue-bound antibody which is immunologically reactive with TAL-H or a derivative.

Also included is a method for monitoring the therapy of an immune-mediated neurodegenerative disease associated with transaldolase-specific autoimmunity in a subject, which method comprises testing a biological fluid obtained from the subject for the presence of antibodies or T lymphocytes which are immunologically reactive with the human transaldolase protein or derivative of the invention, wherein a decrease in the level of the antibodies is indicative of successful therapy.

The invention provides a method for blocking the inhibition of transaldolase enzymatic activity by anti-transaldolase antibodies comprising providing to the antibodies (in vitro or in vivo) an amount of transaldolase protein or functional derivative effective to block the inhibition. This amount can readily be ascertained by one skilled in the art without undue experimentation.

Another embodiment is a kit for detecting the presence of anti-TAL-H antibodies in a biological fluid, the kit being compartmentalized to receive in close confinement therein one or more containers, the kit comprising (a) an antigen comprising TAL-H or an immunoreactive derivative thereof; and (b) a detectably labeled binding partner for an anti-TAL-H antibody.

In the kit, the antigen is preferably immobilized on a solid support. The detectable label in the kit may be a radioisotope, an enzyme, a chromophores and a fluorophore. The anti-TAL-H antibody may be detectably labeled, or preferably, a binding partner such as an anti-immunoglobulin antibody is detectably labeled.

BRIEF DESCRIPTION OF THE DRAWINGS

FIGS. 2A, 2B and 2C show the DNA sequence of a 1332-bp full-length cDNA clone 4/2-4/1 (SEQ ID NO:1). EcoRI restriction sites are underlined. The translated 337 residue amino acid sequence of a 1011-nucleotide-long open reading frame is indicated (SEQ ID NO:2. Polyadenylation site is indicated with a double underline. Exon start sites are marked based on comparative analysis with corresponding genomic clones. Upstream from the first methionine codon, the cDNA contains an uninterrupted open reading frame starting at position three (frame c) as indicated by an arrow (®), allowing expression of a 157 amino acid long protein from the 5' 4/2 474-bp EcoRI fragment (FIG. 6).

FIG. 3 shows nucleotide sequence homologies between the 4/2 repetitive section, 5' 474-bp EcoRI fragment, of cDNA 4/2-4/1 and HTLV-I and HRES-1, respectively, using the BESTFIT program. HTLV-I nt 1105–1140 is SEQ ID NO:3. HTLV-I nt 1753–1780 is SEQ ID NO:4. HRES-I nt 1297–1335 is SEQ ID NO:5. HRES-I nt 21–44 is SEQ ID NO:6.

FIG. 5 shows sequence homologies between the translated amino acid sequence of cDNA 4/2-4/1 (TAL-H) (SEQ ID NO:2) and the yeast transaldolase protein (TAL-Y) (SEQ ID NO:7). Potential phosphorylation sites are indicated in TAL-H. Calmodulin-dependent protein kinase (Calkin) and cAMP-dependent protein kinase (cAMP-P) sites are underlined with solid lines. Casein kinase II recognition motifs are double underlined. Serine and threonine residues in potential protein kinase C phosphorylation sites are marked with asterisks.

FIG. 7A: left panel shows SDS-PAGE of yeast transaldolase; right panel shows specific binding of Ab 170 to the 38-kDa yeast transaldolase protein on Western blot. FIG. 7B shows immunoreactivity with Ab 170 of control (total cell and cytoplasm), transaldolase-depleted (fraction 1), and transaldolase-enriched protein fractions (fractions 2 and 3) purified from human peripheral blood lymphocytes. 41 g of protein was loaded in each lane.

FIG. 9, Panel B, is a schematic diagram of cDNA clone 4/2-4/1 used to produce recombinant TAL-H polypeptides. A 474 bp 5' EcoRI fragment was used to express an N-terminal TAL-H polypeptide in pEV-vrf2 vector. Full length TAL-H protein was expressed from a 1033 bp BglII fragment as a fusion protein with GST in the pGEX-2T vector, purified by binding of GST to glutathione agarose beads, and a functional TAL-H was cleaved from GST with thrombin. A 5' BglII site had been introduced into the 1033 bp fragment by PCR-mediated mutagenesis.

FIG. 10A shows expression of a 66 kDa fusion protein containing the 38 kDa TAL-H protein fused to the 28 kDa GST protein in the pGEX-2T/TAL-H/Sense construct. FIG. 10B shows SDS-PAGE analysis of products during successive steps of purification. Lane GST/TAL-H: 66 kDa fusion protein affinity-purified by binding to glutathione-coated agarose beads. Lane GST/TAL-H: fusion protein cleaved with thrombin. Lane TAL-H: TAL-H protein was separated from the agarose bead-bound GST by centrifugation.

FIG. 13 shows amino acid sequence homologies detected with the GAP program of the UWGCG Software between TAL-H and gag/core proteins of HTLV-I (SEQ ID NO:8, SEQ ID NO:9, and HIV-1 (SEQ ID NO:10). Percent homologies and position of identical residues are shown for each sequence alignment (|). Percentage (in parenthesis) and position of functionally similar amino acids between TAL-H and HTLV-I gag p24 are also indicated (:).

FIGS. 14A and 14B show amino acid sequence homologies between TAL-H and gag/core proteins of HTLV-I (SEQ ID NO:8 and 9 (and a fragment of SEQ ID NO:9), HIV-1 SEQ ID NO:11, kunjin flavivirus (FLAV) SEQ ID NO:12), dengue virus (DENGUE) (SEQ ID NO:13), hog cholera virus (HOCV) (SEQ ID NO:14), and poliovirus core protein P2B (SEQ ID NO:15) (obtained using the GAP program of the UWGCG Software) Percent homologies and position of identical residues are shown for each sequence alignment (½). Percentage (in parenthesis) and position of functionally similar amino acids between TAL-H and HTLV-I gag p24 are also indicated (:).

FIGS. 15A, 15B and 15C shows immunological cross-reactivity between recombinant TAL-H and HIV-1 gag p17 proteins by Western blot analysis. Protein lysates from $2 \times 10^5$ control and HIV-1-infected PBL per lane. FIG. 15A: 38 kDa full-length affinity-purified recombinant TAL-H protein (500 ng per lane, FIG. 15B), and HIV-1 Gag4, HIV-1 gagp24, and TAL-H (500 ng of the indicated protein per lane, FIG. 15C) were separated by SDS-PAGE, transferred to nitrocellulose, and incubated with antibodies as earlier described. Immunoreactivities of TAL-H Ab 169, preimmune Ab 169, and HIV-1 gag p17- and gag p24-specific antibodies were assessed at a 1:1000 dilution, while human control serum and F06 serum from an HIV-1-infected donor were added at a 1:100 dilution.

FIG. 18 shows the nucleotide sequence (SEQ ID NO:23) of the transaldolase promoter, which is an 855 bp (TaqI fragment) 5' flanking sequence of TAL-H DNA (SEQ ID NO:1). A transcription start site, corresponding to position +1 in the TAL-H transcript of SEQ ID NO:1 (see FIGS. 2A, 2B and 2C), is double underlined. A putative Sp1 site (regulatory region) is underlined. Sixteen additional potential transcription factor binding sites are also present in this sequence. The first methionine codon of TAL-H cDNA is shown here in boldface. TaqI sites at both ends of the fragment, used for insertion into pBLCAT3 (Luckow, B. et al., *Nucl. Acids Res.* 15:5490 (1987) and pCAT-Enhancer (from Promega) vectors, are shown in italic.

FIG. 19 presents the nucleotide sequence (SEQ ID NO:24) of TARE 6, a retrotransposable element which is part of the TAL-H gene. Open reading frames corresponding to exon 2 (positions 1–27) and exon 3 (positions 975–1093) of TAL-H are capitalized. Splice donor (SD) and acceptor (SA) sites are double-underlined. The $Alu_{Sc}$-like dimer (positions 929 to 641) are underlined. Typical RNA polymerase II split promoter sites A and B are indicated.

DESCRIPTION OF THE PREFERRED EMBODIMENTS

Figure 17:
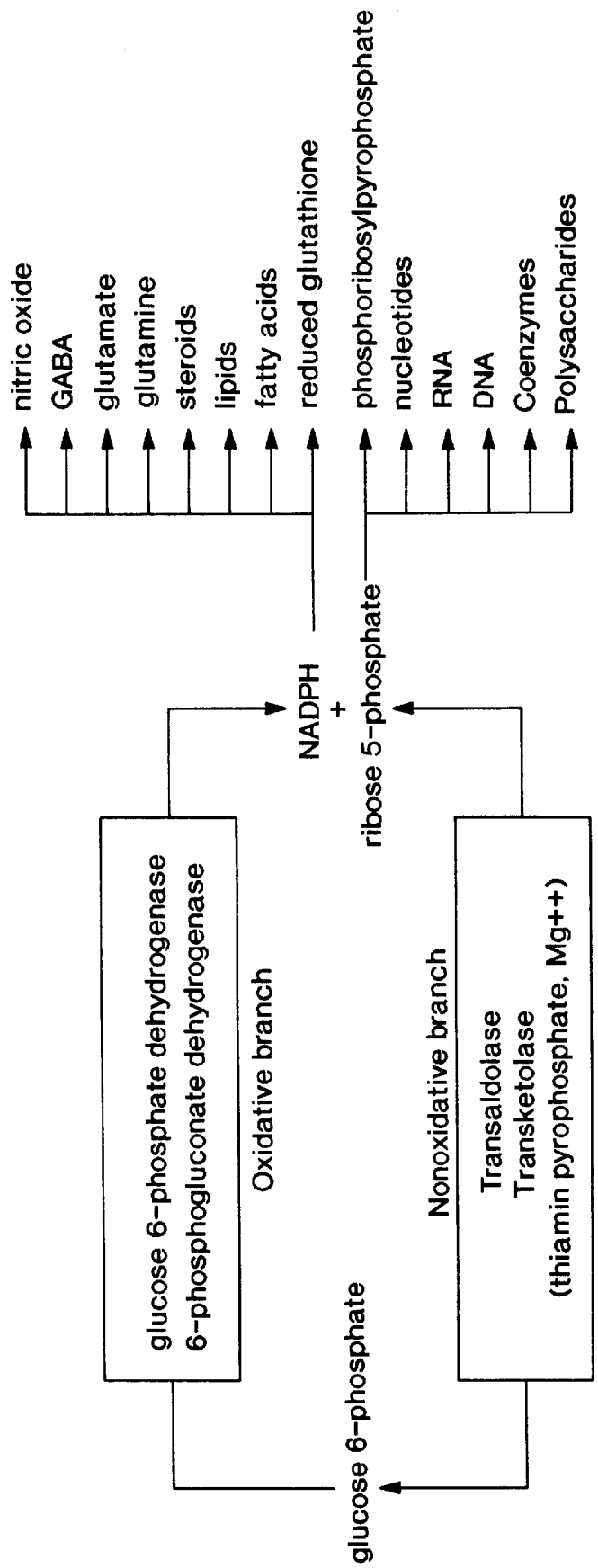
FIG. 17 presents a schematic diagram summarizing the importance of the pentose phosphate pathway (PPP) and transaldolase (TAL) in metabolic and biosynthetic processes. The arrowheads indicate that the oxidative branch is irreversible while the nonoxidative branch is fully reversible.

The present inventor, seeking to identify clinically relevant transcriptionally active RTEs encoding autoantigens, cloned and sequenced a yet uncharacterized highly repetitive RTE based on a limited sequence homology to the human T-cell leukemia virus (Seiki, M. et al. (1983) *Proc. Natl. Acad. Sci. USA* 80: 3618–3622) and a related endogenous retroviral sequence designated "HRES-1" (Perl, A. et al. (1989) *Nucl. Acids Res.* 17:6841–6854). This novel RTE (termed transaldolase-associated repetitive element or "TARE") was discovered to constitute an integral part of the coding sequence of the human gene for the enzyme transaldolase (TAL-H), which is a rate-limiting enzyme of the pentose phosphate pathway (PPP) (See FIG. 17). The nucleotide sequence of TARE 6, which includes a transcriptional enhancer, and the sequence of the TAL-H promoter were also obtained and are disclosed herein.

The present has further discovered that transaldolase is specifically expressed in oligodendrocytes in the brain, cells which produce myelin in the central nervous system (CNS) and which have primary involvement in the pathogenesis of demyelinating diseases, including MS. Further, a subset of patients with MS was found to have antibodies to transaldolase in blood and cerebrospinal fluid. It is disclosed herein that recombinant TAL-H induced proliferation and aggregate formation by peripheral blood lymphocytes from MS patients. The autoantigenic epitopes are contained in a retrotransposon-encoded region of the TAL-H gene (Banki, K. et al., 1994, *J. Biol. Chem.* 269:2847, which reference includes the disclosure of part of the present application) showing amino acid sequence homologies with viral core proteins. Patients with HTLV-I-associated T cell leukemia (ATL) and with HIV infection were therefore tested and found to have antibodies which cross-react with TAL-H. These discoveries suggest that autoimmunity directed to the TAL-H protein plays an important role in the selective destruction of oligodendrocytes in MS and in the pathogenesis of other immune-related neurodegenerative disorders such as those associate with retroviral infection. Anti-TAL-H antibodies in such patients were found to inhibit the enzymatic activity of TAL-H, indicating an additional mechanism by which such autoimmune reactivity could contribute to the diseases. This further suggested to the inventor approaches to treating such diseases, involving blocking antibody action or replacing the TAL-H enzyme by gene therapy.

In the following description, reference will be made to various methodologies known to those of skill in the art of immunology, cell biology, and molecular biology. Publications and other materials setting forth such known methodologies to which reference is made are incorporated herein by reference in their entireties as though set forth in full.

TRANSALDOLASE PROTEINS, PEPTIDES AND DNA

The TAL-H protein and peptides of the present invention are those peptides which are characterized in that they (1) have the amino acid sequence shown in FIGS. 2A, 2B and 2C (SEQ ID NO:2) or a fragment thereof, (2) bind to an anti-TAL-H antibody (either a patient's autoantibody, a polyclonal antiserum produced in an animal or a monoclonal antibody (mAb). The protein or peptide may also be characterized by its ability to bind to and trigger a biological reaction in a T lymphocyte, such as a T lymphocyte from an MS patient, or a T cell line or T cell clone derived from TAL-H-reactive T lymphocytes. One preferred peptide is the N-terminal peptide comprising amino acids 1–157.

Figure 1:
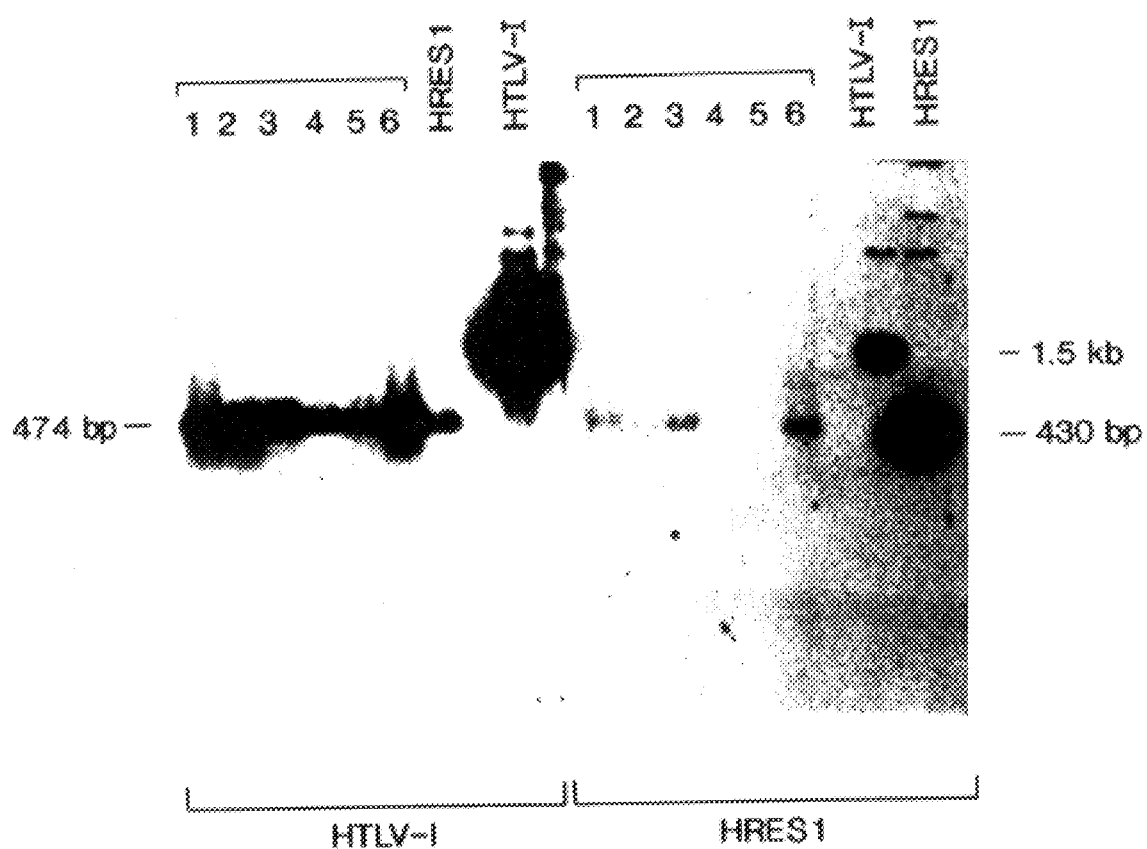
FIG. 1 shows hybridization of 1.5 kb HTLV-I gag-specific pMAI and 430 bp HRES-1 probes to cDNA clones 1–6 isolated from a S gt10 cDNA library of HL60 cells. cDNA clones were digested with EcoRI and run in a 1% agarose gel along with 430 bp HRES-1 and 1.5 HTLV-I gag-containing positive control fragments. Content of each well is indicated on top, while origin of hybridization probes is indicated on bottom of Southern blots. Hybridization (6×SSC, 0.5% SDS, 600° C.) and washing (2×SSC, 0.1% SDS, 55° C.) was done under low stringency conditions.

A preferred TAL-H polypeptide is the full-length protein (SEQ ID NO:2) encoded by cDNA clone 4/2-4/1 (SEQ ID NO:1) which sequence is depicted in FIG. 1. Another preferred peptide is an N-terminal peptide consisting of amino acid residues 1–139 of SEQ ID NO:2. This peptide is encoded by the 5' 474 bp EcoRI fragment (clone 4/2) of SEQ ID NO:1. Yet another peptide of the present invention is a C-terminal peptide consisting of amino acid residues 150–337 of SEQ ID NO:2. This peptide is encoded by the 3' 827 bp EcoRI fragment (clone 4/1) of SEQ ID NO:1.

As described in more detail in the Examples, below (and FIGS. 12 and 13), the amino acid sequence homologies between TAL-H and gag/core proteins of HTLV-I (Seiki et al., supra), HIV-1 (Ratner, L. et al., 1987, *AIDS Res. Hum. Retrovirus.* 3:57–69), kunjin flavivirus (FLAV) (Speight, G. et al., 1988, *J. Gen. Virol.* 69:23–34), dengue virus (DENGUE) (Osatomi, K. et al., 1990, *Virology* 176:643–647), hog cholera virus (HOCV) (Meyers, G. et al., 1989, *Virology* 171:555–567), and poliovirus core protein P2B (Hughes, P. J. et al., 1986, *J. Gen. Virol.* 67:2093–2102), serve as one basis for selection of TAL-H peptide for use in accordance with the present invention. These preferred TAL-H sequences are targets for immune responses (antibody and/or T cell-mediated) which cross-react with epitopes of these viruses. Therefore, antibody and T cell reactivity in autoimmune diseases such as MS as well as virus-induced or virus-associated neurodegenerative diseases such as those caused by HTLV-1 and HIV-1, will be specific for these epitopes of TAL-H. These are shown in Table I, below.

A TAL-H peptide of the present invention may comprise one or more T cell epitopes. A T cell epitope is a portion of the protein which is presented by Class II MHC glycoproteins to T cell receptors. Epitope-specific T cells are either activated by such an epitope in the appropriate context, or may be rendered nonresponsive in an antigen-specific manner by a modified form of this T cell epitope. Thus, among the "functional derivatives" of the TAL-H protein described herein are included those which render specific T cells unresponsive.

TABLE I

| TAL-H PEPTIDE[1] | SEQUENCE | CROSS-REACTIVE VIRAL ANTIGEN |
|---|---|---|
| 17–28 | QLKQFTTVVADT (SEQ ID NO:16) | HTLV-I gagp19 |
| 30–139 | DFHAIDEYKP QDATTNPSLI LAAAQMPAYQ ELVEEAIAYG RKLGGSQEDQ IKNAIDKLFV LFGAEILKKI PGRVSTEVDA RLSFDKDAMV ARARRLIELY KEAGISKDRI (SEQ ID NO:17) | HTLV-I gag p24 |
| 90–220 | LFGAEILKKI PGRVSTEVDA RLSFDKDAMV ARARRLIELY KEAGISKDRI LIKLSSTWEG IQAGQAGKEL EEQHGIHCNM TLLFSFAQAV ACAEAGVTLI SPFVGRILDW HVANTDKKSY EPLEDPGVKS VTKIY (SEQ ID NO:18) | Dengue |
| 3–62 | SSPVKRQRME SALDQLKQFT TVVAD$\mu$gDFH AIDEYKPQDA TTNPSLILAA HIV MPAYQELV (SEQ ID NO:19) | p17/Flavivirus |
| 12–62 | ESALDQLKQF TTVVAD$\mu$gDF HAIDEYKPQD ATTNPSLILA AAQMPAYQEL V (SEQ ID NO:20) | HIV p17 |
| 243–288 | IKALAGCDFL TISPKLLGEL LQDNAKLVPV LSAKAAQASD LEKIHL (SEQ ID NO:21) | HTLVI g24/ Polio CP2B |
| 164–220 | CNMTLLFSFA QAVACAEAGV TLISPFVGRI LDWHVANTDK KSYEPLEDPG VKSVTKIY (SEQ ID NO:22) | Hog Cholera virus |

[1]Numbers refer to amino acid residues of TAL-H protein, SEQ ID NO:1 (see also FIGS. 2A, 2B and 2C)

TAL-H protein, or a peptide fragment thereof, may be expressed using conventional recombinant DNA methods, as described in the Examples below, or synthesized as peptides using chemical methods well-known in the art. Thus, a partial of full length DNA sequence encoding TAL-H may be expressed as a fusion protein in a bacterial system, wherein the unwanted part of the fusion protein is ultimately cleaved and separated from the TAL-H protein or peptide. Such methods are described in detail in a number of references which are hereby incorporated by reference in their entirety: Sambrook, J. et al., *Molecular Cloning: A Laboratory Manual*, 2nd Edition, Cold Spring Harbor Press, Cold Spring Harbor, N.Y., 1989; Ausubel, F. M. et al. *Current Protocols in Molecular Biology*, Vol. 2, Wiley-Interscience, New York, 1987; Albers, B. et al., *Molecular Biology of the Cell*, 2nd Ed., Garland Publishing, Inc., New York, N.Y. (1989); Lewin, B. M., *Genes IV*, Oxford University Press, Oxford, (1990); Watson, J. D., et al., *Molecular Biology of the Gene*, Volumes I and II, Benjamin/Cummings Publishing Co., Inc., Menlo Park, Calif. (1987); and Watson, J. D. et al., *Recombinant DNA*, Second Edition, Scientific American Books, New York, 1992.

A DNA sequence encoding TAL-H or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, ligation with appropriate ligases, or the synthesis of fragments by the polymerase chain reaction (PCR). Techniques for such manipulations are disclosed by the above references and are well-known in the art.

Intact native proteins are made in bacteria by providing a strong, regulated promoter and an efficient ribosome binding site. Levels of expression may vary from less than 1% to more than 30% of total cell protein. A "promoter region" or "control region" contains a promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like. If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a TAL-H coding sequence) are said to be operably linked if the nature of the linkage between the two DNA sequences does not (1) result in the introduction of a frame-shift mutation, (2) interfere with the ability of the promoter region sequence to direct the transcription of the TAL-H gene, or (3) interfere with the ability of the TAL-H gene to be transcribed under control of the promoter. A promoter region is operably linked to a DNA sequence if the promoter is capable of effecting transcription of that DNA sequence. Thus, to express the TAL-H protein, transcriptional and translational signals recognized by an appropriate host are necessary.

Prokaryotic hosts and DNA constructs useful in expressing the TAL-H gene are described in the examples below. A preferred prokaryotic promoter is selected from the following group: promoters capable of recognizing the T4 (Malik, S., et al., *J. Biol. Chem.* 263:1174–1181 (1984); Rosenberg, A. H., et al., *Gene* 59:191–200 (1987); Shinedling, S., et al., *J. Molec. Biol.* 195:471–480 (1987); Hu, M., et al., *Gene* 42:21–30 (1986)), T3, Sp6, and T7 (Chamberlin, M., et al., *Nature* 228:227–231 (1970); Bailey, J. N., et al., *Proc. Natl. Acad. Sci. USA* 80:2814–2818 (1983); Davanloo, P., et al., *Proc. Natl. Acad. Sci. USA* 81:2035–2039 (1984)) polymerases; the $P_R$ and $P_L$ promoters of bacteriophage S (*The Bacteriophage Lambda*, Hershey, A. D., ed., Cold Spring Harbor Press, Cold Spring Harbor, N.Y. (1973); *Lambda II*, Hendrix, R. W., ed., Cold Spring Harbor Press, Cold Spring Harbor, N.Y. (1980)); the trp, recA, heat shock, and lacZ promoters of *E. coli*; the I-amylase (Ulmanen, I., et al., *J. Bacteriol.* 162:176–182 (1985)) and the [-28-specific promoters of *B. subtilis* (Gilman, M. Z., et al., *Gene* 32:11–20 (1984)); the promoters of the bacteriophages of Bacillus (Gryczan, T. J., in: *The Molecular Biology of the Bacilli*, Academic Press, Inc., NY (1982)); Streptomyces promoters (Ward, J. M., et al., *Mol. Gen. Genet.* 203:468–478 (1986)); the int promoter of bacteriophage lambda; the bla promoter of the β-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277–282 (1987)); Cenatiempo, Y. (*Biochimie* 68:505–516 (1986)); Watson, J. D., et al., 1987 m supra; and Gottesman, S. (*Ann. Rev. Genet.* 18:415–442 (1984)). In addition, the TAL-H gene can be transfected into a eukaryotic cell and overexpressed in such a cell to yield useable protein. This is exemplified in the Examples, below. In such a case, a preferred promoter is a eukaryotic promoter or a viral promoter. Preferred eukaryotic promoters include the promoter of the mouse metallothionein I gene (Hamer, D., et al., *J. Mol Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal4 gene promoter (Johnston, S. A., et al., *Proc. Natl. Acad. Sci. USA* 79:6971–6975 (1982); Silver, P. A., et al., *Proc. Natl. Acad. Sci. USA* 81:5951–5955 (1984)).

The present invention also provides DNA molecules which are regulatory elements of the TAL-H gene. Specifically included is the TAL-H promoter, shown in FIG. 18 (SEQ ID NO:23). This promoter is active in driving transcription of TAL-H DNA and is further inducible with insulin, as described in the Examples for a reporter system. Another preferred regulatory DNA sequence is TARE 6 (SEQ ID NO:24) shown in FIG. 19. This element also has transcription stimulatory activity, in particular in concert with the above promoter (see Examples). The promoter and TARE-6 DNA molecules are useful a regulatory sequences in expression vehicles and may be inserted into such constructs using methods well-known in the art (Sambrook et al., supra). Furthermore these sequences or fragments thereof are useful as probes in nucleic acid detection assays to detect polymorphisms, variations in regulatory elements, other related retrotransposable elements and genes which include TARE 6. The TAL-H gene and other genes which include TARE 6 or homologous sequences may have developed by insertion of TARE. The probes of the present invention are therefore useful to identify such genes. An example of such a gene is HSAG-1, which includes an element capable of eliciting a leukemia-associated human cell surface antigen (Stanner, C. P. et al., *Cell* 27:211–221 (1981); Chamberlain, J. W. et al., *Nucl. Acid Res.* 14:3409–3424 (1986); Price, G. B. et al., *Immunol. Lett.* 9:9–14 (1985)). Such probes can be used for the diagnosis of diseases associated with abnormalities in quantity or expression of TARE 6-related elements.

Nucleic acid detection assays can be predicated on any characteristic of the nucleic acid molecule, such as its size, sequence, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents well-known in the art. Kourilsky et al. (U.S. Pat. No. 4,581,333) describe enzyme labels. Radioisotopic labels are disclosed in U.S. Pat. No. 4,358,535 and U.S. Pat. No. 4,446,237. Fluorescent labels (Albarella et al., EP 144914), chemical labels (U.S. Pat. No. 4,582,789; U.S. Pat. No. 4,563,417), modified bases (Miyoshi et al., EP 119448), etc., have also been used in an to improve efficiency of detection. The target nucleic acid molecule may be detected directly or following amplification by a method such as polymerase chain reaction. The nucleotide sequence of the probe of the present invention is selected such that it is capable of hybridizing with the target nucleic acid molecule. In another embodiment, the probe sequence has a nucleotide sequence which is substantially identical to the target DNA or RNA. In this second embodiment, the target molecule is detected indirectly through the detection of a molecule, in the sample, having a complementary sequence.

Based on homology of TAL-H with TAL-Y, indicating structurally or functionally important regions of the enzyme, a peptide having about 11–15 amino acids and sharing high sequence homology with TAL-Y (up to 100%) is within the scope of the present invention. Such peptides can readily be identified by inspection of the two sequences (see, for example, FIG. 5).

These proteins and peptides are recognized by the immune system (either by T cells or antigen-presenting cells) and are capable of inducing the proliferative response of a subject's T lymphocytes to an MS autoantigen, particularly, TAL-H. More preferably, for therapeutic uses, the proteins or peptides are those which inhibit the stimulation of patient T lymphocytes with the autoantigen and thereby protect a subject from an immune-related neurodegenerative disease, such as MS. A peptide including a T cell epitope of the invention, which is administered to a subject in a therapeutic regimen, is capable of modifying the response of the individual to the TAL-H autoantigen leading to inhibition of the autoimmune response.

Identification of modified or substituted peptides ("functional derivatives," as described below) which are useful in the diagnostic and therapeutic methods of the present invention can be easily accomplished by testing their ability to inhibit proliferative responses in vitro of patient T cells, or TAL-H-specific T cell lines or clones, or inhibit binding of TAL-H to antibodies. Inununodominant epitopes in TAL-H which are targeted by antibodies and T cells in MS patients are identified by use of truncated and/or mutagenized recombinant proteins and a series of peptides that "walk" the TAL-H protein in ten amino acid steps. These peptide epitopes are tested for their "antigenicity" in eliciting T cell proliferation or in binding to antibodies. Epitope specificity and affinity of TAL-H autoantibodies against such epitopes (or the full length protein is assessed in the appropriate body fluid.

According to the present invention, peptides are provided which can compete efficiently with full-length TAL-H or the N-terminal 139 amino acid fragment of TAL-H for recognition by T lymphocytes which are associated with MS or another inmmune-related disease which involves TAL-H reactivity. Other preferred peptides were listed in Table I, above. A most preferred peptide is one which includes the lysine residue at position 142 (Lys-142) of TAL-H, which corresponds to Lys-144 of the yeast enzyme. In another embodiment, the peptides compete with TAL-H for recognition by a TAL-H-specific T cell line or clone. Modification of residues critical for T cell activation will yield a T cell antagonist peptide that can specifically inhibit the proliferative response to native TAL-H.

By the term "TAL-H-specific T cell" is intended any T lymphocyte, T lymphocyte line or clone, which is immunoreactive with TAL-H or a fragment thereof. Immunoreactivity with TAL-H is intended to include binding of TAL-H or a peptide fragment thereof or the stimulation of the cells' biologic activity including protein synthesis, DNA synthesis, blastogenesis, cell proliferation, aggregation or cytotoxicity. Such T lymphocytes are particularly associated with MS or other neurodegenerative diseases characterized by the presence of TAL-H reactivity, such as amyotrophic lateral sclerosis (ALS) or Guillain-Barre syndrome (GBS). Production of TAL-H specific T cell lines and clones is described below.

The present invention is intended to include not only full length TAL-H but peptide fragments thereof and functional derivatives of the protein and peptides which maintain, and preferably improve, their functional characteristics in vitro or in vivo (see below), including their pharmaceutical characteristics. Preferably a functional derivative is one which retains immune reactivity with anti-TAL-H antibodies, T lymphocytes or both. Functional derivatives include a TAL-H peptide having one or more amino acid substitutions. Such substitutions may render the peptide incapable of stimulating TAL-H-specific T cells but capable of inactivating or tolerizing such T cells, as is known in the art.

Truncated recombinant proteins are useful to evaluate clustering of immunodominant epitopes within larger fragments of TAL-H. Studies by the present inventor using Western blot analysis showed that sera from MS patients reacted not only with the fill length TAL-H protein but also with the 22 kDa N-terminal peptide. This study revealed a complete correlation of immunoreactivities to the protein and peptide among patients and controls, indicating that B cell epitopes are present in the N-terminal fragment of TAL-H. To test for antigenic epitopes in the C-terminal region of TAL-H, a 828 bp 3' EcoRi fragment of TAL-H cDNA clone 4/2-4/1 (between nucleotides 802 and 1332) is cloned in pGEX-2T in frame downstream of the thrombin cleavage site and a 44 kDa fusion-protein (28 kDa GST+16 kDa C-terminal TAL-H) is expressed and the TAL-H peptide purified (see Examples). Conformational epitopes are tested in EIA. Further truncated C terminal peptides are made and tested similarly.

Amino acid substitutions in a recombinant TAL-H peptide will is accomplished by site-directed mutagenesis via PCR. A novel method, utilizing of a single mutagenic oligonucleotide, in addition to the two outer amplification primers, in a single amplification/mutagenesis reaction is now available (Michael, S. F., 1994, *Biotechniques* 16:410–411). Briefly, a mutagenic oligonucleotide with a greater thermal stability (higher $T_m$) than the outer primers functions most efficiently in this protocol. The mutagenic oligonucleotide is be phosphorylated with T4 polynucleotide kinase and added directly to the PCR reaction. PCR amplification is carried out as described herein with an annealing temperature adjusted to the GC content/melting temperature of the primers. If necessary, denaturing reagents are used for template of high GC content.

Once the most antigenic peptide(s) for MS patient antibodies are identified by immunoassay, their role as conformational B cell epitopes are tested by site-directed mutagenesis. Creation of single amino acid substitutions in TAL-H allows testing of the role of each amino acid in the formation of three-dimensional epitopes.

Recognition of native and mutagenized TAL-H polypeptides by antibodies is be performed by EIA as described below.

It is known that substitution of a single amino acid may significantly alter T-cell immunogenicity of a peptide. Moreover, a single amino acid substitution can also transform an antigenic peptide into a TCR antagonist peptide (Franco, A. et al., 1994, *Eur. J. Immunol.* 24:940–946). Since T cells recognize peptide fragments bound to MHC proteins, immunodominant T cell epitopes in TAL-H are also evaluated using synthetic peptides (see below). To define the role of specific amino acids in formation of B-cell versus T-cell epitopes, effect of mutagenized recombinant TAL-H are tested in antibody binding and T cell proliferation assays described herein.

Unlike B cells which recognize three-dimensional epitopes often comprised of discontiguous amino acids, T cells bind to linear epitopes. TAL-H contains 337 amino acid residues. A panel of 34 synthetic peptides (thirty-three 20 amino acid long and one 16 amino acid long), overlapping by 10 amino acids, may be used to map antigenic epitopes driving TAL-H-specific immune responses in MS. Overlapping synthetic peptides have been successfully used to analyze T cells responses to myelin antigens, including MBP and PLP.

In addition to the studies described in the Examples using Western blot analysis, MS patient sera are tested in EIA with full length recombinant TAL-H to detect recognition of conformational epitopes that may have escaped detection by Western blot. Recognition of individual TAL-H epitopes are revealed with a panel of overlapping synthetic TAL-H peptides as antigens. Human MBP can serve as a reference antigen. A known anti-TAL-H polyclonal antibody or a mAb serves as a positive. Immunodominant peptides identified in this way are further analyzed using corresponding site-directed mutations and deletions in the TAL-H protein as described above.

The above peptides in combination with the antibodies and immunoassays described below will permit rapid and repeated evaluation of disease-associated changes in the titer and epitope specificity of anti-TAL-H antibodies in serum and CSF. These compositions and methods are also useful to monitor changes occurring during the course of therapy.

The term “functional derivative” as used herein also means a “chemical derivative” of the peptide of the invention, which retains at least a portion of the function of the peptide which permits its utility in accordance with the present invention, that is, binding to anti-TAL-H antibody, induction of anti-TAL-H antibody, and binding to and reaction with T lymphocytes specific for TAL-H.

A “chemical derivative” of the peptide of the present invention contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Lysinyl and amino terminal residues are reacted with succinic or other carboxylic acid anhydrides. Derivatization with these agents has the effect of reversing the charge of the lysinyl residues. Other suitable reagents for derivatizing I-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups (aspartyl or glutamyl) are selectively modified by reaction with carbodiimides (R'-N-C-N-R') such as 1-cyclohexyl-3-(2-morpholinyl-(4- ethyl) carbodiimide or 1-ethyl-3(4-azonia 4,4-dimethylpentyl) carbodiimide. Aspartyl and glutamyl residues can be converted to asparaginyl and glutaminyl residues by reaction with ammonium ions.

The specific modification of tyrosyl residues can be by introducing spectral labels by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, such as by the chloramine T method.

Derivatization with bifunctional agents is useful for crosslinking the protein or peptide molecule, such as to a water-insoluble support matrix or surface. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and 4,330,440 are employed for protein immobilization.

Glutaminyl and asparaginyl residues may be deamidated to the corresponding glutamyl and aspartyl residues. Alternatively, these residues are deamidated under mildly acidic conditions.

Other modifications include hydroxylation of proline and lysine, phosphorylation of hydroxyl groups of seryl or threonyl residues, methylation of the I-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Also included in the scope of the invention are salts of the peptides of the invention. As used herein, the term "salts" refers to both salts of carboxyl groups and to acid addition salts of amino groups of the protein or peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids such as, for example, acetic acid or oxalic acid.

It is also understood that enzymatic degradation of the proteins or peptides of the present invention in vivo may cause the peptides to be relatively short-lived. One method of preventing such degradation would be by making synthetic peptides containing a D-amino acid.

Another modification involves extending the peptide by moieties intended to affect solubility, e.g., by the addition of a hydrophilic residue, such as serine, or a charged residue, such as glutamic acid. Furthermore, the peptide could be extended for the purpose of stabilization and preservation of a desired conformation, such as by adding cysteine residues for the formation of disulfide bridges.

Another reason to modify the peptides would be to permit their detection after administration. This can be done by radioiodination (e.g., at the tyrosine residue) with a radioactive iodine isotope, directly, or by first adding one or more tyrosines before radioiodination.

One requirement for a protein or peptide to serve as an inhibitor of T lymphocyte activation or function in accordance with the present invention is that it be a ligand for the T cell receptor (TCR) and/or an MHC molecule. Recognition of this peptide is preferably such that the peptide is bound by a TAL-H-specific T cell with sufficient affinity to compete successfully for binding with a native or other stimulatory TAL-H protein or peptide. Alternatively, the peptide should bind with sufficient affinity to an anti-TAL-H antibody to inhibit the antibody from binding to a cells or tissues or from inhibiting TAL-H enzymatic activity.

Antibodies Specific for Transaldolase

The antibodies of the present invention are reactive with an epitope of TAL-H. The term "antibody" is meant to include polyclonal antibodies, monoclonal antibodies (mAbs), and chimeric antibodies (see below). Preferred antibodies are mAbs, which may be of any immunoglobulin class including IgG, IgM, IgE, IgA, and any subclass or isotype thereof. Preferred antibodies for therapeutic use include antibodies of the IgG2a or IgG2b isotype (Rashid et al., 1992, *J. Immunol.* 148: 1382–1388).

The term "antibody" is also meant to include both intact molecules as well as fragments thereof which bind the antigen, such as, for example, $F(ab')_2$, Fab', Fab and Fv. These fragments lack the Fc fragment of an intact antibody molecule, clear more rapidly from the circulation, and may have less non-specific tissue binding than an intact antibody (Wahl et al., 1983, *J. Nucl. Med.* 24:316–325), properties which may be desirable for particular therapeutic or diagnostic utilities. It will be appreciated that these antigen-binding or epitope-binding fragments of the antibodies useful in the present invention may be used for the detection and quantitation of TAL-H protein or peptides as disclosed herein for intact antibody molecules. Such fragments are typically produced by proteolytic cleavage, using enzymes such as papain (to produce Fab fragments) or pepsin (to produce $F(ab')_2$ fragments) or by reducing the disulfide bridges.

The antibody, fragment or derivative useful in the present invention, may be prepared by using any of a number of techniques well-known in the art. TAL-H protein, its fragments or other derivatives, whether natural, recombinant or synthetic, may be used as an immunogen to generate antibodies which recognize TAL-H. Such antibodies include but are not limited to polyclonal, monoclonal, chimeric, single chain, Fab fragments, and an Fab expression library (Huse et al., *Science* 246:1275–1281 (1989) (see below).

For producing a mAb, any method which provides for the production of antibody molecules by continuous cell lines in culture may be used. As an immunogen, the fall length TAL-H protein, a peptide thereof, or a fusion protein thereof may be used. These methods include, but are not limited to, the hybridoma technique originally described by Kohler and Milstein (1975, *Nature* 256:495–497), and the human B cell hybridoma technique (Kozbor et al., 1983, *Immunol. Today* 4:72), EBV-hybridoma technique (Cole et al., 1985, *Monoclonal Antibodies and Cancer Therapy*, Alan R. Liss, Inc., pp. 77–96), and trioma techniques. A hybridoma of rodent origin producing the mabs of this invention may be cultivated in vitro or in vivo. For an overview of antibody production methods, see: Hartlow, E. et al., *Antibodies: A Laboratory Manual*, Cold Spring Harbor Laboratory Press, Cold Spring Harbor, N.Y., 1988.

In one embodiment, the antibody of the present invention is a human mAb. Human mAbs may be made by any of a number of techniques known in the art (e.g., Teng et al., 1983, *Proc. Natl. Acad. Sci. U.S.A.* 80:7308–7312; Kozbor et al., supra; Olsson et al., 1982, *Meth. Enzymol.* 92:3–16).

In another embodiment, the antibody is a chimeric antibody, preferably a mouse-human chimeric antibody, wherein the heavy and light chain variable regions are derived from a murine mAb and the constant regions are of human origin. The chimeric antibodies of this invention have both the TAL-H-recognizing specificity of the mouse mAb and the biological properties of human antibodies, which include resistance to clearance in the human and lower immunogenicity for humans, allowing multiple treatments. Methods for producing chimeric antibody molecules are disclosed, for example, in Gorman et al., PCT Publication WO 92/06193; Cabilly et al., U.S. Pat. No. 4,816,567 and EPO Publication EP125023; Taniguchi et al., EPO Publication EP171496; Morrison et al., EPO Publication EP173494; Neuberger et al., PCT Publication WO 86/01533; Kudo et al., EPO Publication EP184187; Robinson et al., PCT Publication WO 87/02671; Boulianne et al., *Nature* 312:643–646 (1984); Morrison, *Science* 229:1202–1207 (1985); Neuberger et al., *Nature* 314:268–270 (1985); Takeda et al., *Nature* 314:452–454 (1985); Oi et al., *BioTechniques* 4:214 (1986); and Liu et al., *Proc. Natl. Acad. Sci. USA* 84:3439–3443 (1987).

For human therapeutic purposes, mAbs or chimeric antibodies can be "humanized" by producing human constant region chimeras, where even parts of the variable regions, in particular the conserved or framework regions of the antigen-binding domain, are of human origin, and only the hypervariable regions are non-human. See for example, Winter, UK Patent Publication GB 2188638A; Harris et al., PCT Publication WO 92/04381; Gorman et al., supra); Riechmann et al., 1988, *Nature* 332:323–327.

In yet another fuirther embodiment, the antibody is a single chain antibody formed by linking the heavy and light chain fragment of the Fv region via an amino acid bridge, resulting in a single chain polypeptide (Bird, 1988, *Science* 242:423–426; Huston et al., 1988, *Proc. Natl. Acad. Sci. USA* 85:5879–5883: and Ward et al., 1989, *Nature* 340:544–546).

Antibody molecules or fragments may be purified by known techniques, e.g., immunoabsorption or immunoaffinity chromatography, for example, using Staphylococcal protein A, or chromatographic methods such as HPLC (high performance liquid chromatography), or a combination thereof, etc. In a preferred method, the anti-TAL-H mAb is purified from culture supernatant or ascites fluid.

Once antibodies of the desired specificity are generated, they may be used to identify and select other antibodies having the same or cross-reactive epitope specificity. For example, a new antibody is tested by measuring its ability to inhibit the binding of an antibody of known specificity to its epitope. Various competitive binding assays known in the art can be used.

The isotype of the antibody can be selected during hybridoma production or by appropriate recombinant methods well-known in the art to achieve a desired effector function mediated by the Fc portion of the immunoglobulin heavy chain. For example, certain isotypes, such as IgG2a, have superior activity in antibody-dependent cellular cytotoxicity. Likewise, certain isotypes, such as IgG2a, are more readily eliminated from the circulation through Fc receptors on cells of the reticuloendothelial system and are therefore more efficient at removing an undesired antigen or target cell from sites of active disease (Rashid et al., supra). Accordingly, depending on the intended use, a particular antibody isotype may be preferable to others, as can be readily ascertained by one of ordinary skill in the art without undue experimentation.

Various chemical or biochemical derivatives of the antibodies or antibody fragments of the present invention can also be produced using known methods. Some of these are described above for chemical modification of the TAL-H peptides. One type of derivative which is diagnostically useful is an immunoconjugate comprising an antibody molecule, or an antigen-binding fragment thereof, to which is conjugated a detectable label such as a radioisotope, a fluorescent dye or another tracer molecule. A therapeutically useful immunoconjugate comprises an antibody molecule, or an antigen-binding fragment thereof, conjugated to a therapeutically useful molecule such as a cytotoxic drug or a toxic protein (see, for review: Dilhman, R. O., *Ann. Int. Med.* 111:592–603 (1989)).

Generation of, and Epitope Recognition by, TAL-H Specific T Cell Lines (TCL) And T-Cell Clones (TCC)

PBL are incubated in complete medium (see Examples) at densities likely to contain a single antigen specific cell. Cells are stimulated for 1 week with the TAL-H protein or peptide antigen at concentrations readily ascertainable by those of skill in the art. Interleukin 2 (IL-2) can be added to promote expansion of antigen-specific cells. On about day 8, and subsequently at about weekly intervals, fresh medium is added with $10^4$ irradiated antigen-presenting cells (APC), 50 U/ml rIL2, and antigen. T cell lines are stimulated repeatedly until their response to TAL-H, MBP, or TT equals or exceeds their response to the polyclonal T cell activator, Con A. Established TCLs are cloned by limiting dilution at 0.5 cell/well in 96-well plates with the use of 5 µg/ml ConA and $10^5$ irradiated autologous peripheral blood mononuclear cells (PBMC) as feeder cells. About 50 U/ml IL-2 is added on day 3 and cells are fed biweekly with antigen and IL-2 containing medium. On day 14, cultures showing positive growth are expanded by restimulation with antigen, IL-2, and autologous feeder cells. T cell clones are retested for antigen-specificity in proliferation assays in the presence of APC (autologous Epstein-Barr virus-transformed B cells or irradiated PBMC). TAL-H-specific T cells preferably maintained by stimulation with 50 U/ml IL-2, 5 $\mu$g/ml full length recombinant TAL-H, and $10^5$ irradiated PBMC.

Epitope specificity of TAL-H-responsive T cell lines is determined using a cpanel of overlapping synthetic peptides as described above. Because pathogenesis of MS is likely to involve several autoantigens and a heterogeneous population of T cells, identification of immunodominant T cell epitopes is important for the development of antigen-analog peptide vaccines for MS. T cell responsiveness is assessed generally as described in the examples for PBL, though lower numbers of cells are used. Thus, about $2\times10^4$ T cells are stimulated with 10 and 100 $\mu$g/ml synthetic TAL-H peptide in the presence of APC for 72 h and $^3$H-TdR incorporation measured. The number of T cell lines responding to each immunodominant epitope should reflect the relative frequency of these clones in the peripheral blood and CSF. Therefore, peptides representing immunodominant epitopes are used to stimulate freshly isolated T cells from peripheral blood and CSF and compared to the proliferative response to full length recombinant TAL-H.

T Cell Receptor (TCR) Repertoire of TAL-H Reactive T Cells

TAL-H at concentrations as low as 1 $\mu$g/ml significantly stimulates the proliferation of PBL of MS patients (see Examples, below). Knowledge of the clonality of the T cell response to TAL-H or one of its immunodominant epitopes is important for designing T cell-directed therapeutic interventions. According to the present invention, the TCR usage is determined by examination of VI and VJ-expressing T cell subsets upon stimulation of T cell proliferation by recombinant TAL-H or its immunodominant peptides in comparison to an unrelated antigen such as tetanus toxoid or MBP, or polyclonal stimulation by an anti-CD3 mAb. The SEB superantigen of *Staphylococcus aureus* (Sigma) is used as a positive control for induction of VJ-specific T cells (Kappler, J. et al., 1989, *Science* 244:811–813).

Before and after stimulation with antigens (or anti-CD3 mAb) for about 72 h, total RNA is be prepared from each T cell culture and analyzed for VI and VJ expression by reverse transcriptase mediated PCR (RT-PCR)(Genevee, C. et al., 1992, *Eur. J. Immunol.* 22:1261–1269). If expanded clones dominate the response to immunodominant peptides in a given patient, most TAL-H-specific clones independently generated from that patient will have identical TCR rearrangements. The characterization of such autoreactive clones will not only help to understand the pathogenesis of MS but will also assist in the design of TCR V gene-specific iimmunotherapy (see, for example, Vandenbark, A. A. et al., 1993, *Inter. Rev. Immunol.* 9:251–276; Bourdette, D. N. et al., 1994, *J. Immunol.* 152:2510–2519; Chou, Y. K. et al., *J. Immunol.* 152:2520–2529).

Diagnostic Immunoassays Using TAL-H Antigens and Antibodies

The antibodies and fragments described herein are useful for diagnostic or research purposes in various immunoassays well-known in the art. The antibodies or antibody fragments of the present invention may be used to quantitatively or qualitatively detect the presence or measure the levels of TAL-H protein present in a sample. They can also be used to reveal the expression of TAL on or in cells or tissue samples obtained from a subject. Thus, the antibodies (or fragments or derivatives thereof) useful in the present invention may be employed histologically, as in immunohistochemical staining, immunofluorescence or immunoelectron microscopy, for in situ detection of the TAL-H molecule. Immunofluorescence techniques employ a fluorescently labeled anti-TAL-H antibody or, preferably, a labeled second antibody (see below) coupled with light microscopic, flow cytometric, or fluorimetric detection.

Antibody production by patient lymphocytes can be assessed in vitro using lymphocyte culture in combination with any of the immunoassay methods described below, wherein the culture supernatant is assayed for antibodies. These methods allow evaluation of intrathecal antibody synthesis by measuring anti-TAL-H antibody secretion by CSF-derived lymphocytes. An important additional method is one which allows enumeration of specific antibody secreting cells, such as the "immunospot" assays. This type of assay has been used to demonstrate that MS have cells secreting antibodies to MBP, proteolipid protein (PLP), myelin associated glycoprotein (MAG), and myelin oligodendrocyte glycoprotein (MOG) at frequencies of 1–2 cells per thousand in CSF (Sun, J. et al., 1991, *Eur. J. Immunol.* 21:1461–1468).

According to the present invention, B cells producing TAL-H antibodies are enumerated in the CSF and peripheral blood using an ELISA spot assay (Sedgwick, J. D. et al., 1983, *J. Immunol. Meth.* 57:301–309), which allows detection and enumeration of individual antibody-secreting cells over a solid phase comprising antigen bound to nitrocellulose which results in the immobilization of secreted antibody within the microenvironment of cell. The subsequent application of an anti-Ig reagent conjugated to horseradish peroxidase, followed by a substrate that yields an insoluble purple product, permits visualization of discrete zones of immobilized antibody as "ELISA spots." Other versions of such immunospot assays have been published (Czerkinsky, C. C. et al., *J. Immunol. Meth.* 65:109–121 (1983); Logtenberg, T. et al., *Immunol. Lett.* 9:343–347 (1985); Walker, A. G. et al., *J Immunol. Meth.* 104:281–283 (1987)). Typically, wells of 96-well microtiter plates and nitrocellulose bottoms (Millipore, Bedford, Mass.) are coated with antigen (e.g., at 1 µg/100 µl phosphate buffered saline (PBS)) overnight at 4° C. After washing the wells six times with 0.1% Tween-20 in PBS (pH 7.4), uncoated sites are blocked with 10% fetal calf serum/0.1% Tween 20 in PBS at room temperature for 1 h. Then $2 \times 10^5$ PBL or $10^3$ to $10^4$ CSF cells are added to each well. After incubation overnight at 37° C. in a humidified 5% $CO_2$ atmosphere, the wells are washed in 0.1% Tween 20/PBS, and incubated with goat anti-human IgG, IgA, or IgM antiserum (Tago, Burlingame, Calif.). Subsequently, wells receive horseradish peroxidase-conjugated streptavidin, and are developed with substrate for peroxidase (1 mg/ml 4-chloro-naphthol and 0.003% $H_2O_2$) Antibody-producing cells are counted under an inverted microscope. The frequency of TAL-H producing B cells is expected to be increased in the CSF. This approach provides a new method having diagnostic and prognostic value for MS.

A preferred method for measuring the reactivity of a known anti-TAL-H antibody with a test antigen in a sample, or a known TAL-H antigen preparation with a test antibody in a sample, is by enzyme immunoassay (EIA) such as an enzyme-linked immunosorbent assay (ELISA) (Voller, A. et al., *J. Clin. Pathol.* 31:507–520 (1978); Butler, J. E., *Meth. Enzymol.* 73:482–523 (1981); Maggio, E. (ed.), *Enzyme Immunoassay*, CRC Press, Boca Raton, Fla., 1980). The enzyme, either conjugated to the antibody or to a binding partner for the antibody, when later exposed to an appropriate substrate, will react with the substrate in such a manner as to produce a chemical moiety which can be detected, for example, by spectrophotometric, fluorimetric or by visual means.

Thus, in a preferred EIA of this invention, solid support is coated with antigen or antibody, as the case may be, and a biological sample containing the analyte (antibody or antigen) is contacted with the coated support. The solid support is washed appropriately to remove unbound antibody or antigen. The amount of bound analyte on the solid support may then be detected by conventional means (labeled binding partner, etc.).

By "solid support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

In the EIA, the TAL-H-specific antibody (or the test antigen) is revealed by binding to an enzyme-linked binding partner (e.g., an anti-Ig antibody). This enzyme, in turn, when later exposed to its substrate, will react with the substrate in such a manner as to produce a chemical moiety which can be detected, for example, by spectrophotometric, fluorimetric or by visual means. Enzymes which can be used for the present assay include, but are not limited to, horseradish peroxidase, alkaline phosphatase, β-galactosidase, glucose-6-phosphate dehydrogenase, malate dehydrogenase, staphylococcal nuclease, Δ-V-steroid isomerase, yeast alcohol dehydrogenase, α-glycerophosphate dehydrogenase, triose phosphate isomerase, asparaginase, glucose oxidase, ribonuclease, urease, catalase, glucoamylase and acetylcholinesterase.

In another embodiment, a radioimmunoassay (RIA) is used (see, for example, Weintraub, B., *Principles of Radioimmunoassays*, Seventh Training Course on Radioligand Assay Techniques, The Endocrine Society, March, 1986, pp. 1–5, 46–49 and 68–78).

It is also possible to label a binding partner such as the second antibody with a radioactive, fluorescent, chemiluminescent or bioluminescent tag. Such a second antibody may be specific for the immunoglobulin type of the anti-TAL-H antibody, for example, goat anti-rabbit IgG (when using a rabbit antibody such as Ab 169 described in the Examples). For detection of human anti-TAL-H in a body fluid or bound to cells or tissues in a patient sample, an appropriately labeled anti-human Ig antibody is used. Several preferred assays are exemplified in the Examples, below.

A variety of immunoassay formats is available, for either EIA or RIA systems. For example, assays may be competitive or non-competitive. Two site or sandwich assays may be used, either "forward", "simultaneous" or "reverse" assays, which are well-known in the art.

Additional types of immunoassays useful for detecting the anti-TAL-H antibodies or TAL-H antigens include precipitin reactions, gel diffusion precipitin reactions, immunodiffuision assays, agglutination assays, complement fixation assays, immunoradiometric assays, protein A immunoassays, and immunoelectrophoresis assays.

Binding of the antibody, or fragment or derivative thereof to a TAL-H epitope for which it is specific may be accomplished and/or detected in vitro or in vivo. In vitro binding, as described above, may be performed using histologic specimens, or fractions or extracts of tissue or fluid. In vivo binding may be achieved by administering the antibody (or fragment or derivative) by any route or means known in the art, including but not limited to intravenous, intraarterial or intrathecal, such that specific binding may be detected.

Imaging techniques are used in vivo, wherein the antibody, derivative or fragment is bound to a detectable label capable of in vivo localization. Many different labels and methods of labeling are known in the art.

The present invention provides method for detecting the presence of anti-TAL-H antibodies in a subject suffering from or suspected of being susceptible to, or developing, a neurodegenerative disease. Diseases for which the immunodiagnostic methods of this invention are particularly useful include, but are not limited to, MS, amyotrophic lateral sclerosis, Guillain-Barre Syndrome, tropic spastic paraparesis (or HTLV-1-associated myelopathy) and AIDS-associated encephalopathy. The diagnostic methods of the present invention are useful for any disease now known to be, or yet to be identified as being, associated with the presence of anti-TAL-H antibodies. The immunodiagnosis is based on detecting specific anti-TAL-H antibodies in a biological sample from a test subject. Biological samples which may be tested according to the present invention include any body fluid, such as peripheral blood, serum, plasma, cerebrospinal fluid, lymph, peritoneal fluid, and the like, or any body tissue or extract thereof. Preferably samples for the diagnostic methods of the present invention include blood and CSF.

The assays described above can be used to monitor the effects of therapy in a patient having an immune-related neurodegenerative disease, preferably an MS patient, or a disease characterized by the presence of anti-TAL-H antibodies. Such disease include, but are not limited to, the retroviral diseases AIDS and HTLV-I-induced acute T cell leukemia (ATL). The Examples below demonstrate the presence of these antibodies in HIV-infected and ATL patients. The therapy being monitored may be immunotherapy or more conventional pharmacotherapy. Such monitoring is performed in accordance with this invention by measuring anti-TAL-H antibodies in a biological fluid of a subject undergoing therapy. Successful therapy will be associated with a loss or progressive decline in levels of the antibody.

Therapeutic Use of Antigens or Antibodies of the Invention

As mentioned above, the compositions of the present invention are also useful in the therapy of MS or other neurodegenerative diseases associated with anti-TAL-H autoimmune reactivity. Such diseases include amyotrophic lateral sclerosis, Guillain-Barre Syndrome, tropic spastic paraparesis (or HTLV-1-associated myelopathy) and AIDS-associated encephalopathy. The therapeutic embodiments of the present invention based on the association between the disease, such as MS, and the presence of anti-TAL-H antibodies and/or TAL-H-specific T cell immunity. Targeted removal or diminution of the concentration of such antibodies or T cells are expected to alleviate symptoms of or progression of the disease, possibly inducing remission.

The TAL-H proteins, peptide or functional derivative preparations are therapeutically useful in part because they may interfere with the binding of T cells via their TCRs to the MHC/antigen complex needed for initiation or propagation of the immune recognition or inflammatory process underlying MS. These compositions also block the inhibitory action of anti-TAL-H antibodies on the enzymatic activity of TAL-H.

The TAL-H protein or peptides according to the present invention are administered to patients having, or known to be susceptible to, an immune-related disease neurodegenerative disease, particularly, MS, in amounts sufficient to protect the patient from the disease by preventing the patient's immune system from activation leading to induction, maintenance or exacerbation of the disease state. The proteins or peptides may be brought in contact with antibodies (in vivo or in vitro) to block the inhibitory action of these antibodies on the enzymatic activity of TAL-H.

The route of administration are preferably intravenous, subcutaneous, intramuscular or intrathecal routes. Alternatively, or contemporaneously, the agents may be given by any or thee following routes: inhalation, intraperitoneal, intranasal, intraarticular, intradermal, transdermal or other known routes.

The therapeutic use of the present invention in the treatment of disease or disorders will be best accomplished by those of skill, employing accepted principles of treatment. Such principles are known in the art, and are set forth, for example, in Braunwald, E. et al., eds., *Harrison's Principles of Internal Medicine*, 11th Ed., McGraw-Hill, New York, N.Y. (1987).

The proteins or peptides of the present invention, or their functional derivatives, are well suited for the preparation of pharmaceutical compositions. The pharmaceutical compositions of the invention may be administered to any animal which may experience the beneficial effects of the compositions of the invention. Foremost among such animals are humans, although the invention is not intended to be so limited.

The pharmaceutical compositions of the present invention may be administered by any means that achieve their intended purpose, for example, by the routes described above. Alternatively, or concurrently, administration may be by the oral route. The peptides and pharmaceutical compositions can be administered parenterally by bolus injection or by gradual perfusion over time.

The dosage administered will be dependent upon the age, sex, health, and weight of the recipient, kind of concurrent treatment, if any, frequency of treatment, and the nature of the effect desired.

The dose ranges for the administration of the compositions of the present invention are those large enough to produce the desired effect, whereby, for example, an immune response to a stimulatory peptide, as measured by T cell proliferation in vitro or a delayed hypersensitivity response in vivo, is substantially prevented or inhibited, and further, where the immune-related disease is significantly treated. The doses should not be so large as to cause adverse side effects, such as unwanted cross reactions, generalized immunosuppression, anaphylactic reactions and the like.

Effective doses of a TAL-H protein or peptide of this invention for use in treating an immune-related disease, particularly MS, are in the range of about 1 ng to 100 mg/kg body weight. A preferred dose range is between about 10 ng and 10 mg/kg. A more preferred dose range is between about 100 ng and 1 mg/kg.

In addition to peptides of the invention which themselves are pharmacologically active, pharmaceutical compositions may contain suitable pharmaceutically acceptable carriers comprising excipients and auxiliaries which facilitate processing of the active compounds into preparations which can be used pharmaceutically.

To enhance delivery or bioactivity, the peptides can be incorporated into liposomes using methods and compounds known in the art.

Preparations which can be administered orally in the form of tablets and capsules, preparations which can be administered rectally, such as suppositories, and preparations in the form of solutions for injection or oral introduction, contain from about 0.001 to about 99 percent, preferably from about 0.01 to about 95 percent of active compound(s), together with the excipient.

Suitable formulations for parenteral administration include aqueous solutions of the peptides in water-soluble form, for example, water-soluble salts. In addition, suspensions of the peptides as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The peptides are formulated using conventional pharmaceutically acceptable parenteral vehicles for administration by injection. These vehicles are nontoxic and therapeutic, and a number of formulations are set forth in *Remington's Pharmaceutical Sciences*, (supra). Nonlimiting examples of excipients are water, saline, Ringer's solution, dextrose solution and Hank's balanced salt solution. Formulations according to the invention may also contain minor amounts of additives such as substances that maintain isotonicity, physiological pH, and stability.

The peptides of the invention are preferably formulated in purified form substantially free of aggregates and other undesired materials, preferably at concentrations of about 1.0 ng/ml to 100 mg/ml.

Animal Model of TAL-H Specific Autoimmunity

For years, experimental allergic encephalomyelitis (EAE) in guinea pig, rat and mouse has been touted as an animal model of MS. A model involving an antigen more relevant to human MS, TAL-H, is within the scope of the present invention. Guinea pig, rat and mouse strains known to have a propensity to develop EAE upon injection with other myelin antigens will be used. Such an animal models are useful for testing the feasibility of specific immune interventions, such as antigen analogs, TCR peptides, antibodies to class II MHC molecules, oral vaccination, or administration of cytokines. The possession of such a model will permit identification of targets for regulating the TAL-H specific autoimmune response with TAL-H-specific peptide vaccines.

Lewis and Buffalo rats (6–8 weeks old), B10.PL, PL/J, SJL/J, and SWR mice (10–15 weeks old), and guinea pigs (8–10 weeks old) are immunized with recombinant TAL-H; animals receive antigen subcutaneously in two sites of the hind flank. Guinea pig MBP is used as a "positive" control. In some instances, mice and rats are injected i.v. with $10^{10}$ killed *Bordetella pertussis* organisms. Animals are observed daily, beginning on day 8 for clinical signs of EAE and are scored using conventional criteria well-known in the art. Histological evaluation is performed using conventional perfusion, fixation and staining methods to observe evidence of perivascular infiltration by mononuclear cells and demyelination. Lymph nodes and spleens of animals are removed after immunization to evaluate TAL-H-specific immune responses of sensitized cells in vitro. Sera are evaluated for the presence of TAL-H antibodies by ELISA and Western blot assays.

Having now generally described the invention, the same will be more readily understood through reference to the following examples which are provided by way of illustration, and are not intended to be limiting of the present invention, unless specified.

EXAMPLE I

Cloning and Expression of the Human Transaldolase Gene: Materials and Methods A. Screening of cDNA and Genomic Libraries A S gt10 cDNA library of HL-60 human myelomonocytic leukemia cells, which were found to express HTLV-I and HRES-1 related transcripts, was screened under low stringency conditions (2×SSC, 55° C.) with pMAI, a long terminal repeat (LTR) and gag region-containing HTLV-I probe. Positive clones were identified by hybridization with a $^{32}$P-labeled pMAI probe. Hybridization was carried out in 6×SSC (1×SSC in 0.15M NaCl plus 0.01 5M sodium citrate), 1× Denhardt's solution (Sambrook, J. et al. (1987) *Molecular Cloning: A Laboratory Manual*. Cold Spring Harbor Laboratory Press, New York), 1 mM $Na_2$-EDTA, and 0.5% SDS. After overnight hybridization, the filters were washed under low stringency conditions in 2×SSC and 0.1% SDS at 55° C. for 2 h. Such screening would identify sequences containing at least 12 identical nucleotides in contiguity, assuming a 50% GC content (Perl et al., 1989, supra; Wahl, G. M. et al., (1979) *Proc. Natl. Acad. Sci. USA*. 76: 3683–3687). A human lymphocyte genomic DNA library was prepared in S DASH phage (Stratagene, La Jolla, Calif.) and screened with 4/2 and 4/1 cDNA clones under high stringency conditions as earlier described (Perl et al., supra).

B. Southern Blot Hybridization

High molecular weight genomic DNA was isolated from peripheral blood lymphocytes, digested to completion with restriction endonucleases (BRL, Gaithersburg, Md.), separated by electrophoresis in 0.7% agarose gels, denatured, and transferred to nylon membranes by Southern blotting as described earlier (Perl et al., supra). The blots were hybridized as indicated above except for the addition of 100 μg/ml boiled salmon sperm DNA. Genomic blots were washed under high stringency conditions (Wahl et al., supra) in 0.1×SSC, 0.1% SDS for 90 min at 65° C.

C. Northern Blot Analysis

Total RNA was extracted by the RNAzol method (Chomzynsky, P. et al., (1987) Anal. Biochem. 162:156–159). Poly(A+) RNA was isolated by binding to poly(U) Sephadex column (GIBCO-BRL), fractionated in 1% glyoxal gels, and transferred to nylon membranes (Sambrook et al., supra). Hybridization and washing were done under high stringency conditions.

D. Hybridization Probes

The HTLV-I specific pMAI probe used in these experiments is a 1.5 kb EcoRI-ClaI fragment which contains the 5' LTR and the entire gag gene of HTLV-I (Seiki et al., supra). As an HRES-1 specific probe, a 5.5 kb HindIII fragment of HRES-1/1 or its HTLV-related 430 bp EcoRI- SmaI subfragment was used (Perl et al., 1989, supra). TAL-H specific cDNA probes include the full length 1332 nucleotide long 4/2-4/1 clone and its 5' 474 bp EcoRI fragment, termed 4/2, and 3' 827 bp EcoRI fragment, termed 4/1. All cDNA clones were propagated in the Bluescript KS+ vector (Stratagene, La Jolla, Calif.). A human J-actin cDNA probe, pFH5 (1.5 kb XhoI fragment) was used as a transcriptional control (Gunning, P. et al., (1983) Mol. Cell. Biol. 3:787–795). All DNA probes were purified from vector in preparative agarose gels and labeled with $^{32}$P-dCTP by random oligomer priming (Feinberg, A. P. et al., (1984) Anal. Biochem. 132:6–13).

E. DNA Sequencing

Double-stranded plasmid DNA was denatured by NaOH and sequenced in both strands by the chain termination method using the Sequenase System (USB). The obtained sequence was analyzed with the University of Wisconsin Genetics Computer Group (UWGCG) software and submitted to GenBank (Accession Number: L19437).

F. Prokaryotic Expression of Recombinant Protein

A 474 bp EcoRI fragment, that is, the 4/2 fragment of the 4/2-4/1 cDNA, which contains an uninterrupted open reading frame, was ligated into the pEV plasmid vector and expressed in E. coli RR1 [pRK248cIts] (Crowl R. et al., (1985) Gene 38:31–38). Construction of the vector is such that an A μg codon is placed before the codon corresponding to the first amino acid of the mature gene product. Bacterial cultures were grown at 30° C. in M9 medium with 0.5% glucose, 10 mM MgSO$_4$, 10 μg/ml thiamine, 20 μg/ml thymine, 10 μg/ml proline, 1 TM CaCl$_2$, 0.5% Casamino acids. Expression of the recombinant protein was induced by growing the bacteria at 42° C. Bacterial lysates were resuspended in 1/10 volume of Laemmli buffer and analyzed by SDS-PAGE (Laemmli, U. K. (1970) Nature 227:680–685). Specifically, cells were lysed in SDS-PAGE sample buffer and the lysates electrophoresed in a 12% SDS-polyacrylamide gel and stained with Coomassie Brilliant Blue.

G. Antibodies

New Zealand white rabbits were immunized on two separate occasions three weeks apart with 500 mg gel-purified 22 kDa recombinant protein encoded by cDNA clone 4/2. Specific reactivity of immune sera 169 and 170 to the 22 kDa protein was evaluated by Western blot analysis using preimmune rabbit sera as negative control.

H. Western Blot Analysis

Protein lysates from cells and tissues were resuspended in Laemmli buffer (Laemmli, supra) at a total protein concentration of 4 mg/ml as determined by the Lowry method (Lowry, O. H. et al., (1951) J. Biol. Chem. 193:265–275) using bovine serum albumin as standard. 40 μg total protein in 10 μl per well was separated by SDS-PAGE and electroblotted to nitrocellulose (Banki, K. et al., (1992) Proc. Natl. Acad. Sci. USA, 89: 1939–1943). Nitrocellulose strips were incubated in 100 mM Tris pH 7.5, 0.9% NaCl, 0.1% Tween 20, and 5% skim milk, with antibodies (at a 1000-fold dilution unless indicated otherwise) for 1 h at room temperature. After washing, the strips were incubated with horseradish peroxidase-conjugated goat anti-rabbit IgG (Boehringer Mannheim, Indianapolis, Ind.). In between the incubations the strips were vigorously washed in 0.1% Tween-20, 100 mM Tris pH 7.5, and 0.9% NaCl. The blots were developed with a substrate comprised of 1 mg/ml 4-chloro-naphthol and 0.003% hydrogen peroxide.

Purification and Testing of Transaldolase Enzyme Activity from Peripheral Blood Lymphocytes Peripheral blood lymphocytes (PBL) were separated on a Ficoll-Hypaque gradient (Boyum, A. (1968) Scand. J. Clin. Lab. Invest. 21(Suppl. 97):77–89). 2–3 g of pelleted cells were resuspended in 3 volumes of ice-cold NaHCO$_3$, sonicated, and centrifuged at 4° C. at 3000×g for 5 min. The supernatant was adjusted to pH 4.8 and fractionated by sequential addition of 25% (fraction 1), 36% (fraction 2), and 51% acetone (fraction 3) at −20° C., as described (Tsolas, O. et al., (1970) Arch. Biochem. Biophys. 136: 287–302). The fractions were pelleted by centrifugation at −10° C. with 5000×g for 10 min and resuspended in a buffer of 40 mM triethanolamine/10 mM EDTA pH 7.6. Transaldolase enzyme activity was tested in the presence of 3.2 mM D-fructose 6-phosphate, 0.2 mM erythrose 4-phosphate, 0.1 mM NADH, 10 μg I-glycerophosphate dehydrogenase/triosephosphate isomerase at a 1:6 ratio at room temperature by continuous absorbance reading at 340 nm for 20 min (Pontremoli, S. et al., (1961) Proc. Natl. Acad. Sci. USA 47: 1942–1955). The assay was conducted in the activity range of 0.001–0.01 U/ml using yeast transaldolase as a positive control. All reagents for the transaldolase assay were from Sigma.

EXAMPLE II

Cloning and Sequencing of cDNA (4/2-4/1) Related to HTLV-I and HRES-1, Encoding the Human Gene for Transaldolase HRES-1 is a single-copy ERS which is transcribed into a 6 kb mRNA (Perl, A. et al. (1989) Nucleic Acids Res. 17: 6841–6854). However, lowering the stringency of hybridization of HRES-1 to human genomic DNA and total cellular RNA, a series of additional highly abundant DNA fragments and transcripts were detected by Southern and Northern blot analysis, respectively. HRES-1 exhibited no significant sequence homology with the previously characterized highly repetitive short and long interspersed elements.

Figure 4:
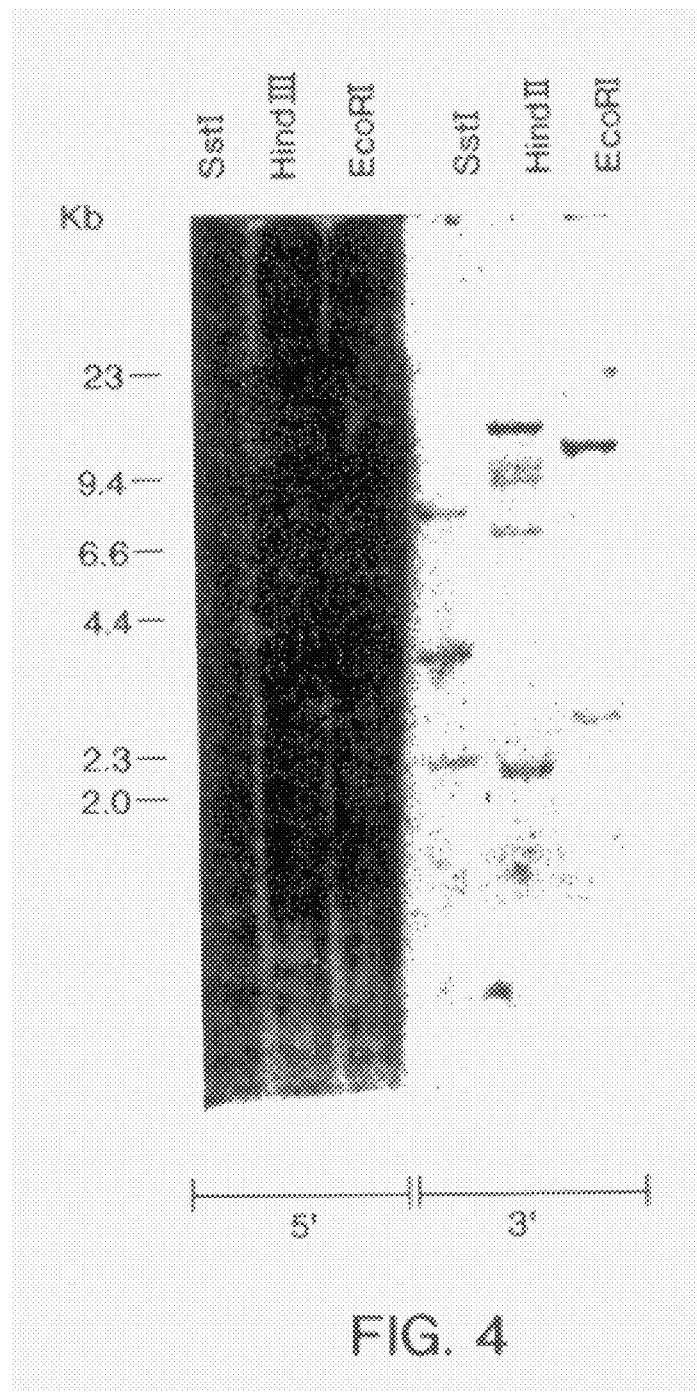
FIG. 4 shows a Southern blot analysis of normal human lymphocyte genomic DNA digested with the restriction enzymes indicated at the top of each lane. The left three lanes indicate hybridization to the 5' 4/2 (474-bp EcoRI) fragment, whereas the right three lanes indicate hybridization to the 3' 4/1 (827-bp EcoRI) fragment of the 4/2-4/1 full-length cDNA.

In order to identify potentially novel transcriptionally active RTEs low stringency screening of a human myelomonocytic cell line (HL-60) cDNA library with HRES-1 (HRES-1/1) and HTLV-I specific probes (pMAI) was undertaken. The level of stringency applied was expected to detect sequences containing at least 12 complementary nucleotides in contiguity, assuming a 50% GC content (Perl et al., 1989, supra; Wahl, G. M. et al., supra). Positive cDNA clones were digested with EcoRI and further examined by Southern blot hybridization. Under the stringency of hybridization applied, all cDNA clones contained an EcoRI insert of identical size (FIG. 1). Intensive cross-hybridization was noted between the uniform cDNA sequences, termed 4/2, and HTLV-I. A relatively lower intensity cross-hybridization between HRES-1 and 4/2 was also detected. The 4/2 cDNA probe annealed to a 1.3 kb mRNA species in polyA+ RNA from normal lymphocytes. Subsequently, a 1.3 kb full-length cDNA was cloned by re-screening the HL-60 cDNA library with the 4/2 probe. The 474 bp HRES-1/HTLV-I-related EcoRI fragment was found to comprise the 5' end of the full-length 1332 bp cDNA clone, designated as 4/2-4/1. The 4/2-4/1 clone was sequenced in both strands by the chain termination method (FIGS. 2A, 2B and 2C.; SEQ ID NO:1). DNA sequence homologies with HRES-1 and HTLV-I are confined to GC-rich sections within the repetitive region (FIG. 3) explaining the cross-hybridizations between these sequences. Separate high stringency Southern blot hybridizations of the 5' 4/2 (474 bp EcoRI fragment) and 3' 4/1 (827 bp EcoRI fragment) regions of the full length 4/2-4/1 cDNA to human genomic DNA demonstrated that the 5' region is highly repetitive while the 3' region is represented in a single copy per haploid genome (FIG. 4).

The 4/2-4/1 cDNA clone contains an open reading frame capable of encoding a 337 amino acid long protein (FIG. 5) (Human: SEQ ID NO:2; Yeast: SEQ ID NO:7). Computer search of GenBank, NBRF, and EMBL revealed that the 4/2-4/1 cDNA is different from any known human or viral nucleotide or amino acid sequence. However, a 52% DNA sequence similarity was noted between clone 4/2-4/1 and the yeast transaldolase gene (Schaaf, I. et al., (1990) *Eur. J. Biochem.* 188:597–603). The translated amino acid sequence of cDNA 4/2-4/1 showed a 58% overall sequence similarity with the transaldolase protein (FIG. 5).

Thus, the human transaldolase cDNA clone 4/2-4/1 is 1332 nucleotides in length which correlates well with detection of a 1.3 kb mRNA in polyA(+) RNA from a variety of cell lines and tissues. Downstream of the open reading frame, the cDNA contains a typical polyadenylation site, AATAAA (Proudfoot, N. J. et al., (1976) *Nature* 263:211–214). The 1011 bp open reading frame in the human cDNA encodes a protein of 337 amino acids with a predicted molecular mass of 37.6 kD. This is similar to the 37 kDa size of the yeast TAL gene comprised of 335 amino acids. The overall homology of translated amino acid sequences of the human (TAL-H) and yeast transaldolase proteins (TAL-Y) is 58%. However, there are blocks of 11–15 amino acids in which the identity is 100%. Presumably, these regions are important for the structure and/or function of the enzyme. Homology between TAL-H and TAL-Y was further substantiated by reactivity of antibodies to the human recombinant protein with yeast transaldolase (see below). Comparative amino acid sequence analysis also indicated that the calmodulin dependent protein kinase and five of the seven protein kinase C phosphorylation sites are missing in the yeast enzyme. This structural differences suggest that function of the two enzymes may be differentially regulated. Western blot analysis of protein lysates from Chinese hamster ovary cells and murine lymphocytes also demonstrated a 38 kDa protein indistinguishable from human TAL-H. This phylogenetic conservation from yeast to man suggests that TAL-H plays an essential function in cell biology.

EXAMPLE III

Figure 6:
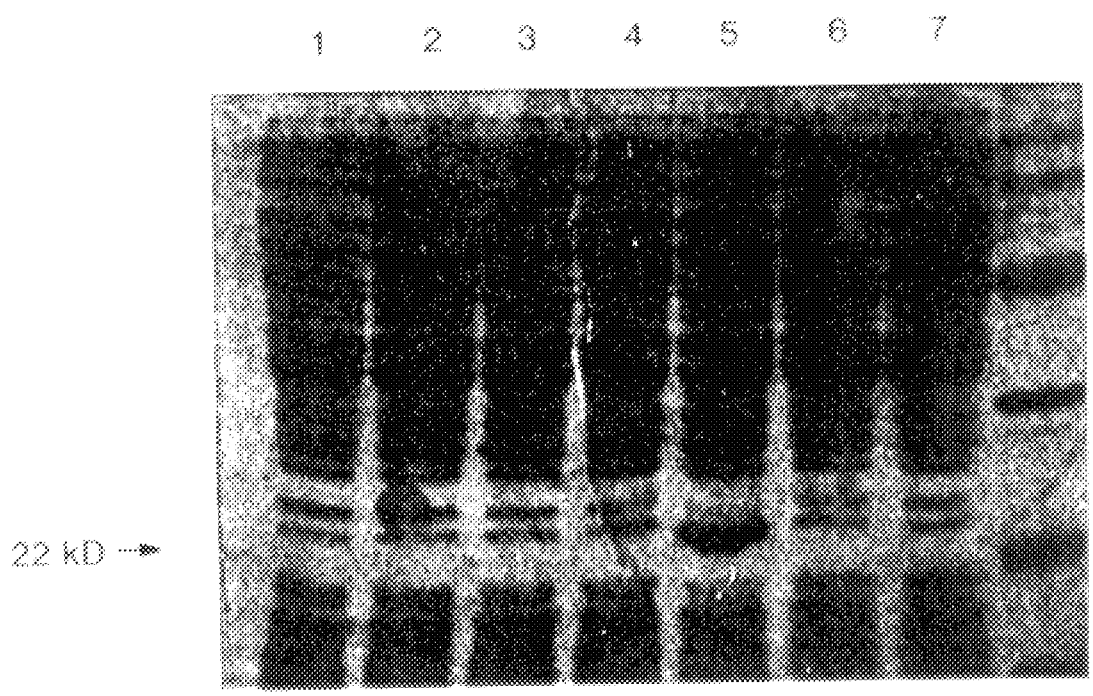
FIG. 6 is a SDS-PAGE gel pattern showing expression of a 22-kDa protein from the 5' 4/2 (474-bp EcoRI) fragment of the 4/2-4/1 cDNA cloned into the vector pEV-vrf2. Vectors pEV-vrf1, pEV-vrf2, and pEV-vrf3 allow expression of three alternative reading frames. pRR248cIts bacteria were transformed with plasmids. Production of a 22-kDa recombinant protein encoded by the human 4/2 cDNA insert was induced by growing the cells at 42° C. for 2 h (lane 5). Negative lanes are: lane 1, pEV-vrf1 with no insert grown at 42° C.; lane 2, pEV-vrf3 with 4/2 cDNA grown at 30° C.; lane 3, pEV-vrf3 with 4/2 cDNA grown at 42° C.; lane 4, pEV-vrf2 with 4/2 cDNA grown at 30° C. (the uninduced control for lane 5), lane 6, pEV-vrf1 with 4/2 cDNA grown at 30° C.; line 7, pEV-vrf1 with 4/2 cDNA grown at 42° C.
Figure 7A:
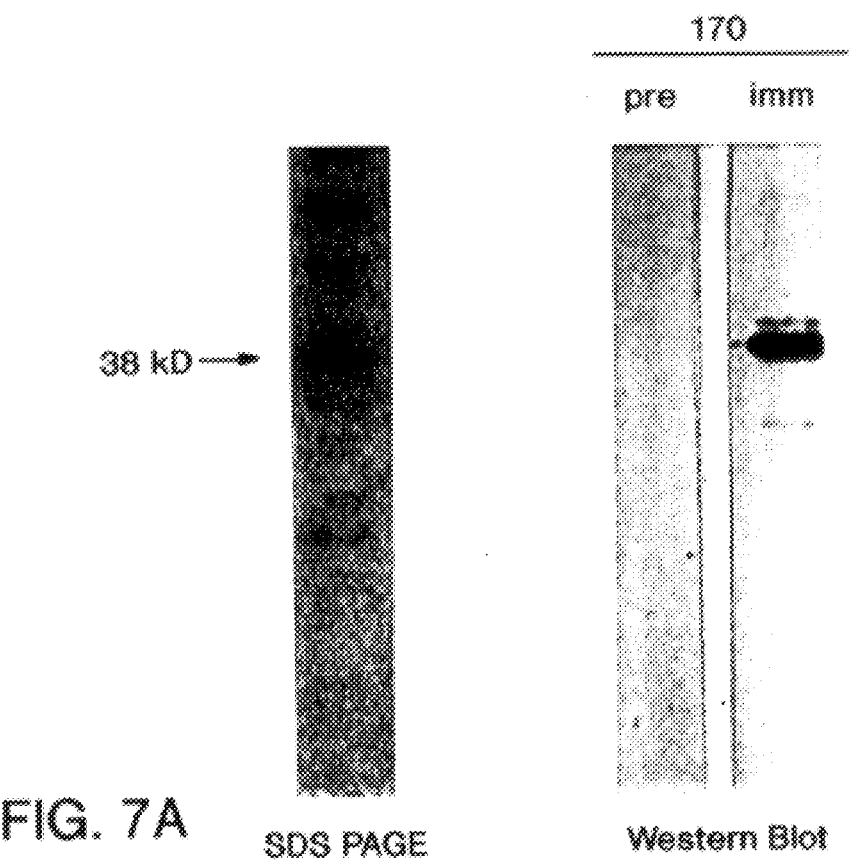
FIGS. 7A and 7B show specific immunoreactivity of Ab 170 with the 38 kDa yeast transaldolase.
Figure 7B:
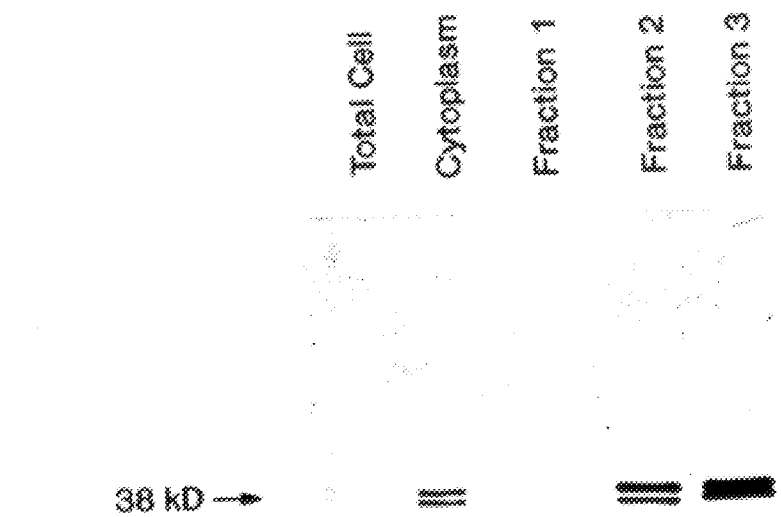

Prokaryotic Expression of 4/2-4/1 cDNA and Immunological Characterization of the Recombinant Protein A. Prokaryotic Expression In order to further characterize the 4/2-4/1 cDNA clone, the 474 bp EcoRI fragment of the cDNA which contains a 157 amino acid long 5' section of the open reading frame, was ligated into the pEV prokaryotic expression vector (Crowl et al., supra) and expressed in *E. coli*. Bacterial cell lysates were analyzed by SDS-PAGE (FIG. 6). The 4/2 cDNA-encoded 22 kDa recombinant protein was gel-purified and used to generate antisera in two rabbits. Antisera from both rabbits, Abs 169 and 170, are specific for the 22 kDa recombinant protein. A native human protein in various cell lines and tissues was identified by Abs 169 and 170 as a 38 kDa doublet (FIGS. 7A and 7B). This correlates strongly with the calculated molecular weight, 37,629.93 daltons, of the 337 amino acid long protein encoded by 4/2-4/1.

B. Antibodies Specific for a 38 kDa Human Protein, are Immunoreactive with Yeast Transaldolase To evaluate whether cDNA 4/2-4/1 corresponds to the human transaldolase gene, reactivity of Abs 169 and 170 with purified yeast transaldolase was evaluated. As shown in FIGS. 7A and 7B, Ab 170 showed specific inunumoreactivity to the 38 kDa transaldolase protein from yeast. Ab 170 did not react with contaminating proteins, and the preimmune rabbit serum displayed no binding to any protein in the yeast transaldolase extract.

C. Co-purification of Transaldolase Activity and Immunoreactivity to Ab 170

Transaldolase was purified from human peripheral blood lymphocytes by sequential precipitation with acetone (Tsolas et al., supra). Enzyme activity was measured by the transfer of the dihydroxyacetone three-carbon unit from the donor D-fructose-6-phosphate, to the acceptor D-erythrose-4-phosphate (Pontremoli et al., supra). A sixteen-fold enhancement of transaldolase specific activity in Fraction 3 correlated with enrichment of the 38 kDa protein species as detected by Ab 170 (FIGS. 7A and 7B).

EXAMPLE IV

Exon-Intron Organization and Mapping of a Retrotransposable Element, TARE 6, in the TAL-H Genomic Locus A human lymphocyte genomic DNA library was screened with 4/2-specific and 4/1-specific probes. While TARE-containing genomic clones were identified by presence of 4/2 but not 4/1 specific DNA and variable flanking sequences, TAL-H genomic clones were selected based on the presence of adjacent 4/2- and 4/1-specific fragments. Exon-intron boundaries of the TAL-H gene locus were determined by sequence analysis of overlapping S DASH clones.

Figure 8:
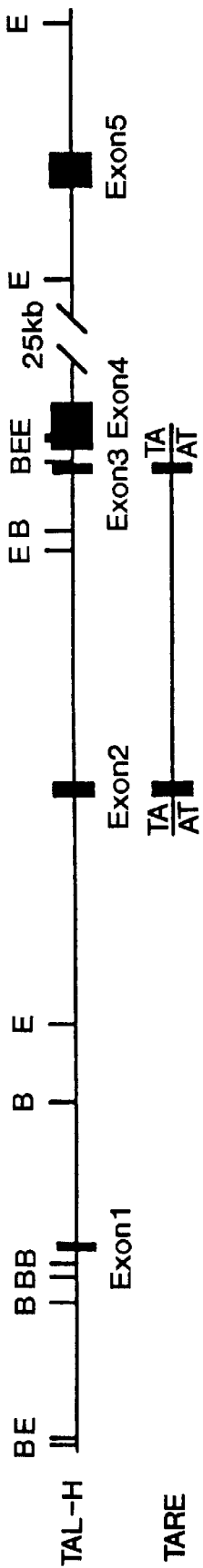
FIG. 8 presents a mapping of a retrotransposable element (TARE) in the human transaldolase (TAL-H) genomic locus. Shaded areas correspond to exons. E, EcoRI; B, BamHI restriction site. TA direct repeats are indicated at both ends of TARE.

Comparative analysis of genomic and cDNA sequences revealed that unlike the intronless TAL-Y locus the TAL-H gene locus contains five exons which span a chromosomal region of approximately 50 kb (FIG. 8). The 4/2 fragment contains four of the TAL-H exons. Exon boundaries within the cDNA are indicated in FIGS. 2A, 2B and 2C., while location of each exon within the TAL-H locus is shown in FIG. 8. While the transaldolase gene locus appears to be a single copy element per haploid genome, TARE flanked by exons 2 and 3 of TAL-H was found to be highly repetitive.

Based on comparative Southern blot analyses and the frequency of TAL-H exons 2 and exon 3 positive clones in two different genomic libraries, the copy number of the TAL-associated repetitive element (TARE) was estimated to be between 1,000 to 10,000 per haploid genome. Direct repeats flanking exons 2 and 3 in the TAL-H locus suggest that these two exons may have uniquely developed by insertion of TARE.

Seven different TARE-harboring genomic loci were cloned and sequenced. All TARE isolates contained segments corresponding to exons 2 and 3 TAL-H at their opposite ends in an orientation matching with the TAL-H locus. Shared segments between TARE and TAL-H showed a sequence identity of >96%. The TARE element in the TAL-H and other loci was flanked by TA direct repeats.

Figure 9:
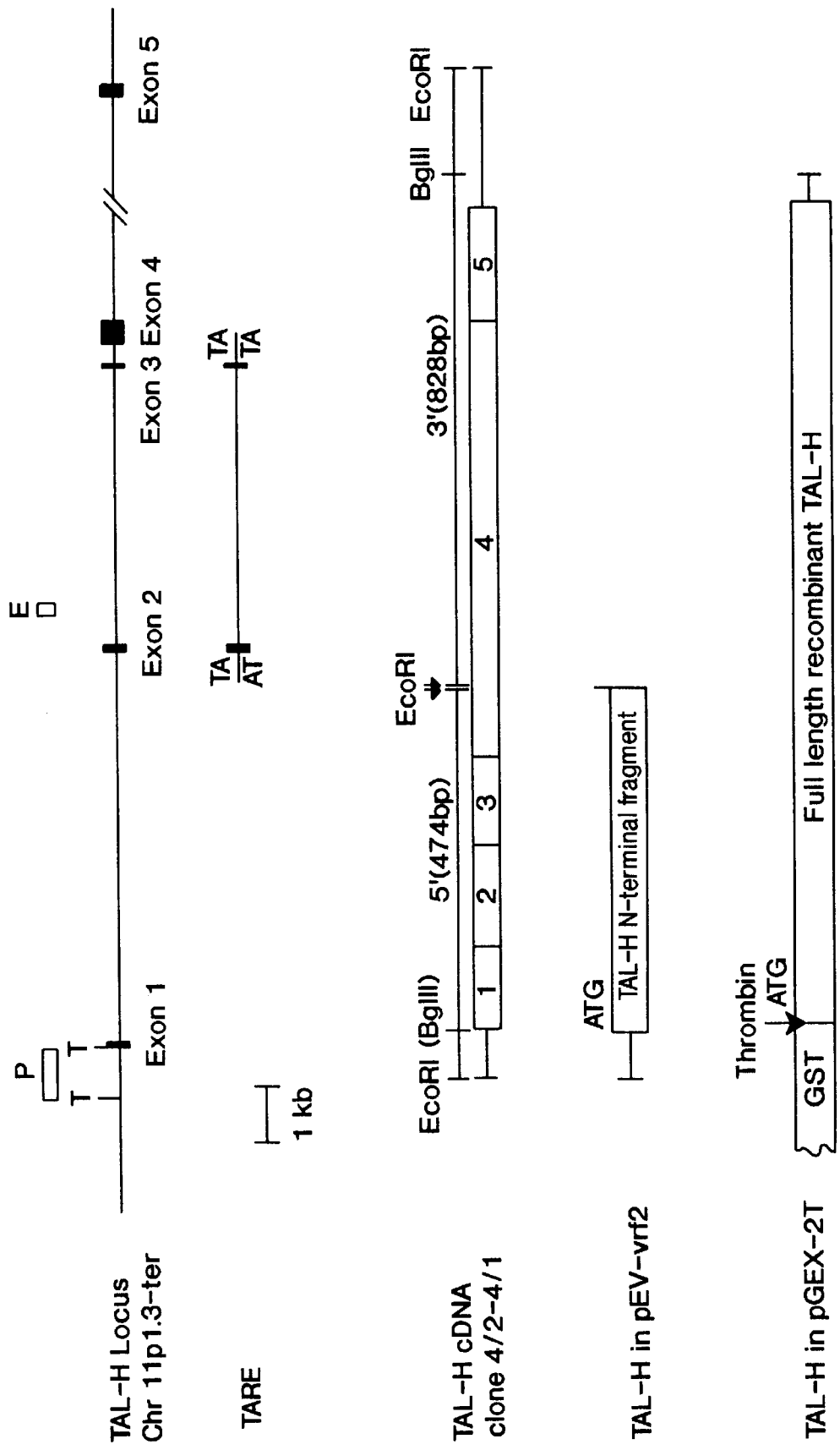
FIG. 9, Panel A shows the exon-intron organization and mapping of a retrotransposable element (TARE, also termed TARE 6)) in the human transaldolase (TAL-H) locus on human chromosome 11. Shaded areas correspond to exons. TA direct repeats are indicated at both ends of TARE. Open bars indicate a 5' promoter element (P) within an 855 bp TaqI (T) fragment. The sequence of this promoter (SEQ ID NO:23) is shown in FIG. 18. Also shown is the site of an enhancer (E), TARE 6 having the sequence SEQ ID NO:24 (shown in FIG. 19).

Based on deletion mapping and in vitro transfection of promoter/chloramphenicol acetyltransferase (CAT) reporter gene/enhancer constructs, two distinct regulatory elements, a promoter in a 5' flanking (855 bp TaqI fragment and a 53 base pair enhancer sequence 802 nucleotidase 3' from exons 2 in the TARE region of the TAL-H locus have been identified. These regions are shown schematically in Panel A of FIG. 9. The nucleotide sequence (SEQ ID NO:23) of the promoter is shown in FIG. 18. The TARE 6 nucleotide sequence (SEQ ID NO:24) is shown in FIG. 19. TARE 6 has internal promoter with two Alu elements and two complete exons from TAL. The transcription of TARE 6 is in direction opposite to transcription of the TAL-H coding sequence.

Studies were performed testing the activity of the promoter and TARE 6 in regulating transcription. Two cell lines, Jurkat (ATCC# CRL8163 human T cell leukemia line) and HOG (human oligodendroglioma; Post, G. R. et al., *GLIA* 5:122–130 (1992) were transfected with reporter gene constructs containing one or both sequences. For the promoter, the TaqI sites at both ends of the fragment were used for insertion into pBLCAT3 (Luckow, B. et al., *Nucl. Acids Res.* 15:5490 (1987) and pCAT-Enhancer (from Promega) vectors. CAT activity was assayed (Banki, K. et al., *AIDS Res. Human Retrovir.* 10:303–308 (1994)). The TAL-H promoter functioned alone as an efficient promoter for CAT expression compared to the promoterless construct. Transfection efficiency was based on co-transfection with the RSVJgal vector. Constructs containing both the promoter and TARE 6 in the order 5'-promoter-CAT-TARE 6-3' yielded higher expression than did the promoter alone in HOG and Jurkat cells. Insulin enhanced activity of constructs containing one or both elements.

TARE may belong to the group of class I RTE comprising the copia and Ty elements and intracisternal A-type particles (Fanning, T. G. et al., (1987) *Biochim. Biophys. Acta* 910:203–212). Presence of TARE in the coding sequence of the human transaldolase gene exemplifies that RTEs may be a major force in shaping of the eukaryotic genome.

EXAMPLE V

Expression and Autoantigenicity of Transaldolase in Multiple Sclerosis Materials and Methods A. Prokaryotic Expression of Recombinant Protein A 157 amino acid long N-terminal segment of TAL-H was expressed in the pEV vector system as described above in Example I (see also, Banki, *J. Biol. Chem.*, 1984, supra).

Figure 10A:
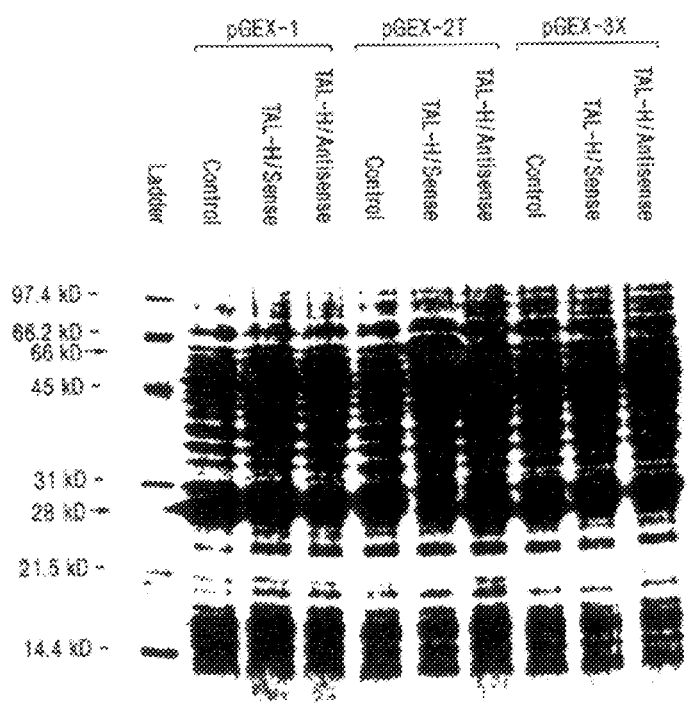
FIG. 10A and FIG. 10B are gel patterns showing expression and purification of full-length TAL-H protein. A 1033 nucleotide long BglII fragment of TAL-H cDNA clone 4/2-4/1, between nucleotide positions 57 and 1090, respectively, was cloned into the BamHI site of pGEX-1, pGEX-2T, and pGEX-3X vectors. JM101 bacteria were transformed with the plasmids, grown to an $OD_{600}$ of 0.6 and then stimulated for 2 h with 1 mM IP $\mu$g. Cells were lysed in SDS-PAGE sample buffer. Lysates of bacteria transformed with TAL-H expression vectors were prepared after induction, electrophoresed in a 12% SDS-polyacrylamide gel and stained with Coomassie Brilliant Blue.
Figure 10B:
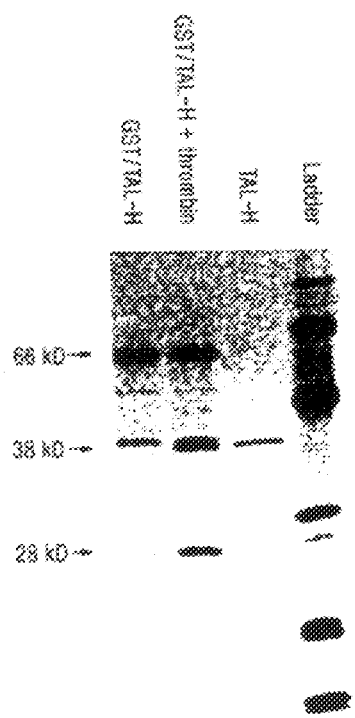

The full-length TAL-H protein was expressed as a fusion protein with glutathione S-transferase (GST) encoded by pGEX-2T plasmid vector (Smith, D. B. et al., 1988, *Gene* 67:31). A BglII site was generated by polymerase chain reaction-mediated mutagenesis immediately 5' of the first methionine codon of TAL-H cDNA. Thus, a 1033 nucleotide long BglII fragment of cDNA clone 4/2-4/1, between nucleotide positions 57 and 1090, respectively, was cloned into the BamHI site of pGEX-1, pGEX-2T and pGEX-3X vectors, immediately downstream of the thrombin cleavage site. JM101 bacteria were transformed with the plasmids, grown to and $OD_{600}$ of 0.6 and then stimulated for 2 h with 1 mM IP μg. Cells were lysed in SDS-PAGE sample buffer. Lysates were electrophoresed in a 12% SDS-polyacrylamnide gel and stained with Coomassie Brilliant Blue. The results are shown in FIG. 10A and FIG. 10B. FIG. 10A shows expression of a 66 kDa fusion protein containing the 38 kDa TAL-H protein fused to the 28 kDa GST protein in the pGEX-2T/TAL-H/Sense construct. FIG. 10B shows SDS-PAGE analysis of products during successive steps of purification. The 66 kDa fusion protein was affinity-purified from the total bacterial lysate through binding to glutathione-coated agarose beads (lane GST/TAL-H). The fusion protein was cleaved with thrombin to separate TAL-H from GST. Lane "GST/TAL-H + thrombin" shows result of proteolytic cleavage. TAL-H protein was separated from the agarose bead-bound GST by centrifugation (lane TAL-H). (Cleavage from GST was accomplished by 1 NIH unit of thrombin (Sigma, St. Louis, Mo.) in 1 ml of PBS containing 600 μg fusion protein. The purified full length recombinant TAL-H was found to be highly functional in the transaldolase enzyme assay, having a specific activities of >10 U and >60 U per mg protein. This assay is described in Example I and in Banki et al., J. Biol. Chem., 1994, supra and in Pontremoli, S. et al., (1961) *Proc. Natl. Acad. Sci. USA* 47: 1942–1955. As references, purified yeast transaldolase (TAL-Y) has an enzyme activity of 10–30 U/mg protein, while normal human lymphocytes contain a transaldolase activity of 0.015 U/mg protein. By contrast, transaldolase activity in human oligodendroglioma cell lines M03.13 (from Dr. Neil Cashman, Montreal Neurological Institute) and HOG (from Dr. Glyn Dawson, University of Chicago) showed >0.2 U/mg protein, indicating that expression of TAL-H may be increased at early stages of oligodendrocyte differentiation.

B. Sequence Analysis

Amino acid sequence homologies were analyzed as described above using the University of Wisconsin Genetics Computer Group (GCG) Software (Devereux et al., supra). The nucleotide sequence of the human transaldolase (TAL-H) gene was submitted to the GenBank™/EMBL Data Bank and received accession number L19437.

C. Reactivities of Anti-TAL-H Antibodies

1. Retroviral Proteins

Reactivity of TAL-H-specific antibody 169 with HIV proteins was investigated by Western blot analysis of protein lysates of HIV-1-infected PBL. Viral reagents were obtained from the NIH AIDS Research and Reference Program. Infectious stock of the strain HIV-1$_{IIIB}$ was harvested from 24 h supernatants of freshly infected H9 cells (ATCC CRL-8543) and infectious titer was determined by an in situ infectivity (MAGI) assay Nagy, K. et al., 1994, *J. Virol.* 68:757). Supernatants with titers of $2.1 \times 10^5$ infectious units (IU)/ml were filtered through 0.45 μm filter and aliquots were stored at −70° C. Normal human PBL purified on Ficoll-Hypaque gradient were prestimulated with 1% phytohemagglutinin (PHA, Wellcome, HA15) and 30 U/ml human recombinant interleukin-2 in RPMI-1640 medium containing 20% fetal calf serum, 100 U/ml penicillin, 100 μg/ml streptomycin, and 2 mM L-glutamine. After three days, PBL were incubated for 4 hr with HIV-1 in the presence of 10 μg/ml Polybrene (Sigma). Infections were standardized by incubating PBL with cell-free virus supernatants containing 100 ng of p24 core protein per $5 \times 10^6$ cells as measured by an ELISA following the manufacturer's recommendations (NEK-060, DuPont, Boston, Mass.). After virus infection, cells were washed in PBS and resuspended in 10 ml of fresh RPMI-1640 medium containing 20% fetal calf serum, 20 U/ml IL-2, 100 U/ml penicillin, 100 µg/ml streptomycin, and 2 mM L-glutamine. Uninfected control PBL were cultured under identical conditions. After infection, the cells were cultured for 8 days and lysed in SDS-PAGE sample buffer at a density of $2 \times 10^7$ cells/ml. Cell lysates were boiled for 5 min and stored at $-20°$ C. until use.

Recombinant HIV-1 gag proteins were obtained through the NIH AIDS Research and Reference Program. HIV-1 SF2 p25/245 gag contained the gag 24 protein (Steimer, K. S. et al., 1986, *Virology* 150:283). HIV-1/IIIB Gag4 contained the p17 C-terminus, beginning at amino acid position 146, all of p24, and the p15 N-terminus (Repligen, Cambridge, Mass.). As positive control sera, HIV-1IIIB p17-specific and p24 specific polyclonal sheep antibodies (Karacostas, V. et al., 1989, *Proc. Natl. Acad. Sci. USA* 86:8964), monoclonal antibodies to p24 and gp41 (Gorny, M. K. et al., 1989, *Proc. Natl. Acad. Sci. USA* 86:1624), and gp120 (Matsushita, S. et al., 1988, *J. Virol.* 62:2107), and a HIV-1 gagp17-reactive human reference serum F06 from the Centers for Disease Control (Atlanta, Ga.) were utilized. Gel-purified recombinant HTLV-I gag p24 was kindly provided by Dr. Chung-ho Hung (Cambridge Biotech, Worcester, Mass.).

2. Western blot analysis 500 ng of recombinant TAL-H protein in 10 µl per well was separated by SDS-PAGE and electroblotted to nitrocellulose (Towbin, H. H. et al., 1979, *Proc. Natl. Acad. Sci. USA* 76:4350). Nitrocellulose strips were incubated in 100 mM Tris pH 7.5, 0.9% NaCl, 0.1% Tween 20, and 5% skim milk, with antibodies (at a 1000-fold dilution unless indicated otherwise) for 1 h at room temperature. For detection of rabbit antibodies, after washing, the strips were incubated with horseradish peroxidase-conjugated goat anti-rabbit IgG (Boehringer Mannheim, Indianapolis, Ind.). For detection of human antibodies, after washing, the strips were incubated with biotinylated goat anti-human serum and, subsequently with horseradish peroxidase-conjugated avidin (Jackson Laboratories, West Grove, Pa.). Between incubations, the strips were vigorously washed in 0.1% Tween-20, 100 mM Tris pH 7.5, and 0.9% NaCl. The blots were developed with a substrate comprised of 1 mg/ml 4-chloronaphthol and 0.003% hydrogen peroxide.

3. Immunohistochemistry

Formalin fixed (10% formaldehyde in PBS) and paraffin-embedded sections of human postmortem brain tissue from subjects without neurological disorders was stained with control preimmune rabbit serum, anti-TAL-H immune rabbit serum 169, rabbit antibodies to anti-glial fibrillary acidic protein (GFAP)(DAKO, Denmark) or anti-galactocerebroside monoclonal antibody (Boehringer Mannheim) at dilutions of 1:5,000. Slides were developed using biotinylated goat anti-rabbit IgG or goat anti-mouse IgG, alkaline phosphatase-conjugated streptavidin, and substrate (all from DAKO).

4. Primary Brain Cell Culture and Immunofluorescence

Primary brain cell cultures were prepared from cerebral hemispheres of 2-day old B10.A mice, as earlier described (Massa, P. T. et al., 1993, *GLIA* 8:201). After 7 days in culture, cells were fixed with 1% paraformaldehyde in 50 mM Tris/150 mM NaCl and permeabilized with 0.25% Triton X-100 in 0.5M Tris, pH 7.4, and stained with Ab 169 or myelin basic protein (MBP)-specific rabbit antiserum (DAKO). Staining was performed using horseradish peroxidase-conjugated swine anti-rabbit antibody and 4-chloronaphthol substrate as described for Western blots. Cell type-specific expression of TAL and MBP was investigated by two-color irmunofluorescence. TAL was detected by Ab 169 and rhodamine-conjugated anti-rabbit goat antibody while MBP was visualized using an MBP-specific rat monoclonal antibody (IgG1, Serotec, U. K.) and FITC-conjugated goat anti-rat antibody. Preimmune rabbit serum (from the animal which produced Ab 169) served as a negative control in combination with rhodamine-conjugated goat anti-rabbit secondary antibody. Also used as a negative control was a rat monoclonal antibody to human interferon-J (IgG1, Serotec) in combination with an FITC-conjugated goat anti-rat secondary antibody controls.

D. Stimulation of Peripheral Blood Lymphocytes

Peripheral blood mononuclear cells were isolated from heparinized venous blood on Ficoll-Hypaque gradient and resuspended in RPMI-1640 medium, supplemented with 10% fetal calf serum, 2 mM L-glutamine, 100 IU/ml penicillin, and 100 µg/ml gentamicin. $10^5$ cells were incubated in each well of a microtiter plate using (six replicates per group). Recombinant TAL-H (fall length, 38 kDa) was added at an optimal concentration of 1 µg/ml. Negative controls (medium alone) and positive controls (10 µg/ml concanavalin A) were included in each experiment. Experiments shown in Table III also included cells incubated in the presence of 30 µg/ml human myelin basic protein (MBP) (18.5 kDa) or 10 µg/ml tetanus toxoid (TT). The plates were incubated at 37° C. in a humidified 5% $CO_2$ atmosphere for 72 h. The cultures were pulsed with 0.4 µCi $^3$H-TdR 8 h before termination. Cells were harvested and $^3$H-TdR incorporation was measured as described earlier (Perl, A. et al., 1984, *Cell. Immunol.* 84:185). The results in Table II were expressed in cpm as mean±standard error (se) of six replicate cultures and as stimulation indices (S.I.) which is the fraction of stimulated divided by control cpm. Table III shows S.I. values only. Statistical analysis was performed using Student's t-test.

EXAMPLE VI

Expression of TAL-H Protein in Oligodendrocytes

Expression of transaldolase is regulated in a developmental and tissue-specific manner (Novello, F et al., 1968, *Biochem. J.* 107:775; Heinrich, P. C. et al., 1976, *Cancer Res.* 36:3189). This enzyme is pivotal in the pentose phosphate pathway (PPP) (FIG. 17), which pathway shows maximal activity in the developing nervous system at a period of active growth and myelination (Baquer, N. Z. et al., 1975, In: *NORMAL AND PATHOLOGICAL DEVELOPMENT OF ENERGY METABOLISM*. F. A. Hommes et al., eds, Academic Press, London, pp109–132).

As described above, the present inventor has cloned human transaldolase cDNA, produced recombinant TAL-H protein, and generated specific antibodies to the TAL-H protein. These achievements now made possible the identification of transaldolase-producing cells using Abs 169 and 170 which are highly specific for the 38 kDa TAL-H protein.

Inmmunohistochemical analysis of postmortem sections revealed that expression of TAL-H is specific for oligodendrocytes in the human brain. Localization of TAL-H to oligodendroglia was confirmed by parallel staining for galactocerebroside (concordant staining pattern with TAL-H; not shown) and glial fibrillary acidic protein (astrocyte-specific discordant staining pattern relative to TAL-H).

Transaldolase is detectable in other mammalian species, including the mouse, by using the human TAL-H probes. Therefore, oligodendrocyte-specific expression was further investigated in murine brain cell cultures (Massa, P. T. et al., 1993, GLIA 8:201). Concordant expression of TAL-H and myelin basic protein (MBP) in the oligodendroglia was demonstrated by simultaneous staining with TAL-H-specific rabbit Ab 169 and a MBP-specific rat monoclonal antibody using two-color immunofluorescence. As negative control, cultures were simultaneously stained with 169 preimmune rabbit serum and a rat monoclonal antibody to human interferon-J. Anti-TAL-H and anti-MBP antibodies showed an identical staining pattern of oligodendrocytes and of their processes, indicating that myelin sheaths may also contain the TAL-H protein. No TAL-H expression was detected in neurons and astrocytes.

EXAMPLE VII

Detection of TAL-H-specific Antibodies in Patients with Multiple Sclerosis

Figure 11A:
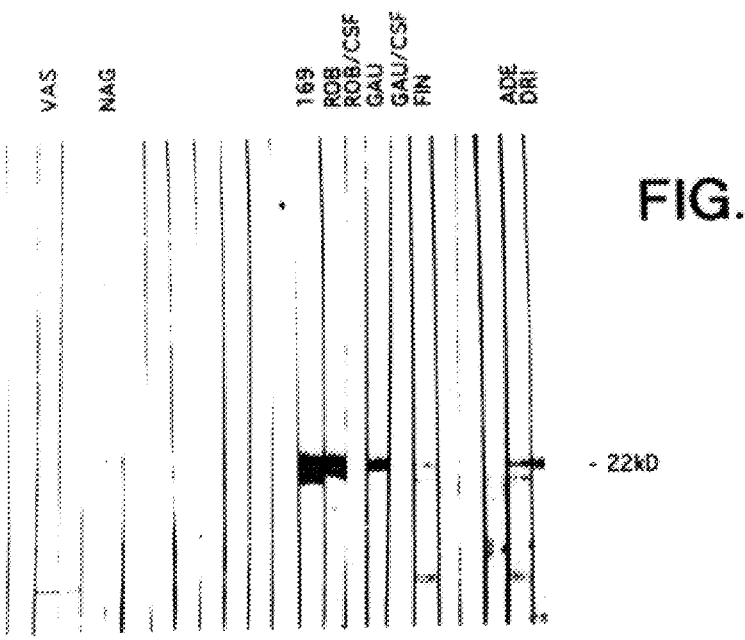
FIGS. 11A, 11B and 11C shows a Western blot analysis of immunoreactivity of MS patient sera with recombinant TAL-H protein. TAL-H-reactive sera are indicated by patients' initials. 1, 2, 3, and C are normal human sera. 169 refers to a TAL-H-specific rabbit antibody. Unmarked lanes indicate TAL-H-negative sera of MS patients. Cerebrospinal fluid (CSF) samples, indicated by the "/CSF" extension, and sera were tested in parallel from patients MS-C, MS-M, MS-R, ROB, and GAU, respectively.
Figure 11B:
Figure 11C:
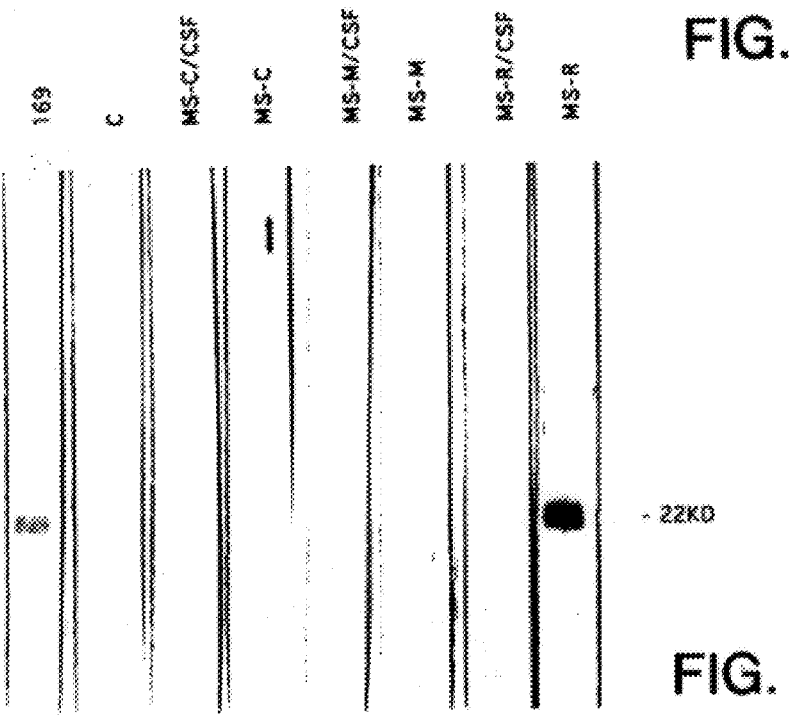

Since oligodendrocytes are selectively destroyed in patients with MS, the possibility that TAL-H is involved as an autoantigen in this process, was investigated. Sera from 171 patients with immunological disorders and sera of 101 control blood donors was studied by Western blot analysis. Seropositivity was based on immunoreactivity to a 22 kDa recombinant TAL-H protein (500 ng of gel-purified TAL-H protein per lane) at serum dilutions of 1:100 or higher. Presence of TAL-H autoantibodies was highly specific for MS. Sera of 25/87 patients with MS and of 1/32 patients with essential cryoglobulinemia (ECG) reacted with recombinant TAL-H protein (FIG. 11A, 11B and 11C). TAL-H specific antibodies were not detected in other autoimmune patients including 19 with Sjogren's syndrome (SJS) and 25 with systemic lupus erythematosus (SLE) and in 101 control blood donors (including 77 healthy subjects and 24 patients with other neurological diseases).

Thus, detection of TAL-H autoantibodies in patients with MS is a highly significant finding, as compared to control subjects and patients with other autoimmune diseases ($p<0.001$, using Chi-square test). No correlation was found between TAL-H seropositivity and immunoglobulin concentrations in the sera of seven patients with MS and four control donors.

Most patients with MS have a disease course characterized by relapses and remissions, termed relapsing/remitting (R/R) MS. A minority of patients have a primarily chronic progressive disease (CP). Many of the R/R patients will, nevertheless, eventually enter a phase of secondary progressive evolution of symptoms. As shown in Table II, presence of TAL-H antibodies was independent of the duration or clinical phase of the disease.

It was observed that 13/17 cerebrospinal fluid (CSF) samples from TAL-H seropositive MS patients contained antibody to TAL-H. 2/3 additional CSF samples from MS patients with no available serum specimen also contained TAL-H antibodies. Thus, antibodies to TAL-H were noted in a total of 15/20 CSF samples from patients with MS. By contrast, TAL-H antibodies were absent in nine CSF samples from patients with other neurological diseases. Representative analysis of serum and CSF samples is shown in FIG. 11A, 11B and 11C. While the amount of TAL-H antibodies was 5–10-fold lower in the CSF than serum of corresponding patients, the concentration of TAL-H antibodies (based on the total immunoglobulin content) was enhanced 50–100 fold in the CSF.

Figure 12:
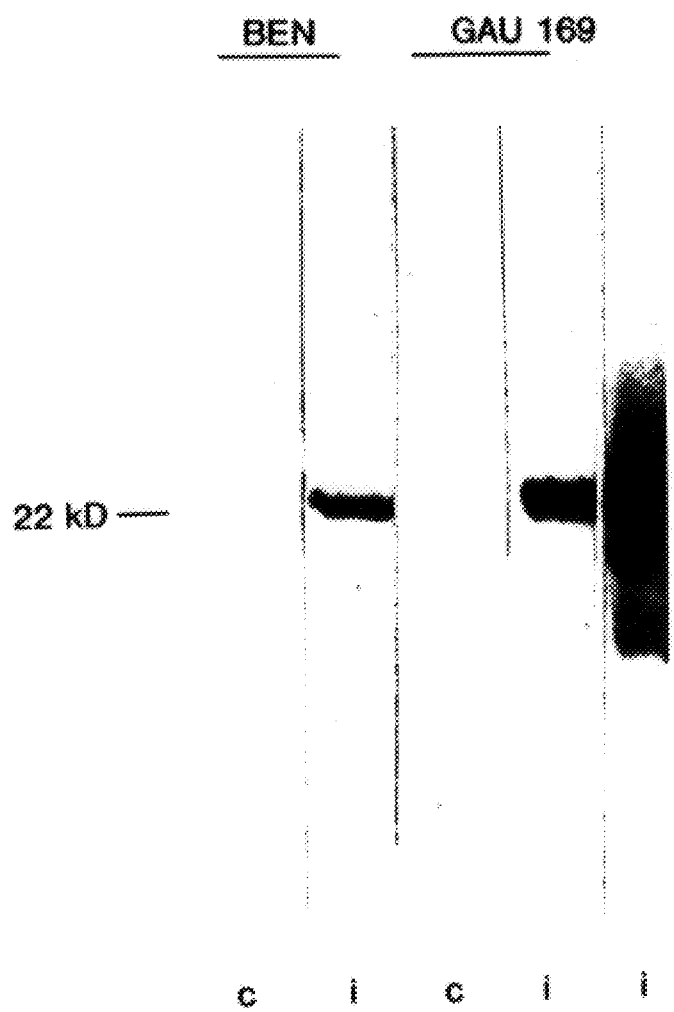
FIG. 12 shows the TAL-H specificity of human autoantibodies from patients BEN (essential cryoglobulinemia) and GAU (multiple sclerosis). Sera BEN and GAU strongly react with induced bacterial lysates containing TAL-H ("i") but do not react with control bacterial lysates ("c").

Recombinant TAL-H protein used in these studies was gel-purified by electroelution in two cycles to exclude possible contamination with bacterial proteins. Abs 169 and 170 showed no reactivity with proteins of bacterial lysates. This indicated that the gel-purified recombinant TAL-H protein, used for immunization of rabbits and testing of seroreactivity of the patients, was essentially free of bacterial proteins. Along the same line, TAL-H positive human sera demonstrated high affinity and specificity to the recombinant protein and showed no reactivity to bacterial proteins (FIG. 12). TAL-H specificity of MS sera was further confirmed by their reactivity with a 38 kDa functional TAL-H protein derived from a GST fusion protein which had been purified as described above. The results indicate that TAL-H is an MS-specific autoantigen and that TAL-H autoantibodies appear to be an important diagnostic and pathogenetic factor in MS.

TABLE II

Disease Status of MS Patients with TAL-H Autoantibodies

| Patient | Age/Sex | Time[1] | Diagnosis |
| --- | --- | --- | --- |
| VAS | 26/F | 4 y | R/R |
| NAG | 23/M | 12 m | R/R |
| ROB | 32/M | 1 m | A |
| GAU | 36/F | 15 m | R/R |
| FIN | 42/F | 10 y | CP |
| ADE | 23/F | 2 m | A |
| DRI | 35/M | 6 m | A |
| MOO | 45/M | 12 y | R/R |
| LEI | 57/F | 23 y | CP |
| BUR | 39/F | 11 y | R/R |
| LEA | 46/M | 11 y | S |
| JOS | 47/F | 8 y | CP |
| PAS | 41/F | 6 y | R/R |
| ASH | 55/F | 6 y | CP |
| COL | 45/F | 1 y | R/R |
| MCG | 36/F | 10 y | R/R |
| MCC | 31/F | 8 m | R/R |
| DIO | 22/M | 3 y | CP |
| GIU | 53/F | 2 y | R/R |
| TUN | N/A | 10 y | CP |
| THO | 33/F | 2 y | R/R |
| SHO | 81/F | 54 y | S |
| GRO | 82/F | 25 y | S |
| MS-H | 38/F | 8 y | CP |
| MS-C | 66/M | 10 y | CP |
| MS-R | 38/F | 5 y | R/R |
| MS-M | N.A. | N.A. | CP |
| JAB | 40/F | 8 y | R/R |
| LAK | 37/F | 3 y | R/R |
| KUB | 48/F | 20 y | CP |

[1]Time from diagnosis: y = year, m = month
Sex: M = male; F = female
Diagnosis: R/R = relapsing/remitting; CP = chronic progressive; A = acute; S = stable.

More recent evidence indicates the presence of anti-TAL-H antibodies in some patients with Guillain-Barre syndrome and with amyotrophic lateral sclerosis.

While myelin and oligodendrocytes do not show significant levels of MHC class II or class I antigen expression or surface expression of MBP (Sobel, R. A. et al., 1988, J. Neuropath. Exp. Neurol. 47:19; Lee, S. C. et al., 1989, J. Neuroimmunol. 25:261), they are sensitive to a direct attack by activated CD4+ T cells (Ruijs, T. C. G. et al., 1993, J. Neuroimmunol. 42:105). A breakdown of the blood brain barrier may provide a route of entry for oligodendrocyte-specific antibodies. Likewise, antibodies to TAL-H may mediate demyelination by attracting microglia and macrophage through their Fc receptors and, thus, triggering phagocytosis and antibody-dependent cell-mediated cytotoxicity (Jankovic, B. D. et al., 1965, Nature 207:428).

To reiterate, antibodies to TAL-H were detected in a patients with MS but were not found in (a) healthy controls, (b) patients with other neurological diseases (with the possible exception of amyotrophic lateral sclerosis and Guillain-Barre syndrome), and (c) patients with systemic autoimmune diseases such as SLE and Sjogren's syndrome. This indicates that the autoinmmune process targeting TAL-H is particularly specific for MS. Concentration of TAL-H antibodies were higher (per total immunoglobulin concentration) in the CSF than in sera. An increase in the amount of immunoglobulins in the CSF has been one of the earliest and most consistently reproduced findings which raised the possibility of an immune-mediated pathogenesis of MS and is routinely used as a diagnostic criterion (Kabat, E. A. et al., 1950, *Am. J. Med. Sci.* 219:55). Thus, intrathecal synthesis of TAL-H autoantibodies may be connected to oligodendroglial expression of the protein and an eventual destruction of oligodendrocytes in MS. In contrast to the discovery of high-affinity TAL-H autoantibodies in MS, antibodies to purified human MBP were not detected by Western blot analysis in this study. This is in accordance with observations by others and suggests that MBP-directed immunity is primarily T cell-mediated (Martin et al., supra; Vandenbark, A. A. et al., 1993, *Inter. Rev. Immunol.* 9:251).

EXAMPLE VIII

Stimulation of Peripheral Blood Lymphocyte Proliferation by TAL-H

In addition to showing increased amounts of total immunoglobulin in the CSF and demyelinating lesions, MS patients have an accumulation of activated T cells surrounding early MS lesions. It is generally accepted that autoreactive T cells in MS patients recognize components of the myelin sheaths. In order to investigate whether TAL-H may be a target of autoreactive T cells, its effect on proliferation of PBL was evaluated. Highly purified recombinant TAL-H antigen was used in these studies to ensure that the responses detected were not directed to any other myelin protein. Addition of 1 μg/ml TAL-H significantly increased proliferation of lymphocytes from eleven MS patients (p<0.001, Table III). The stimulation index varied between 1.4- to 10.3-fold among the patients. Thought lymphocytes were incubated in the presence of 10% autologous serum, heat-inactivation of the autologous serum or use of 10% fetal calf serum had no significant effect on the proliferative responses to TAL-H. Microscopic observation of stimulated cells indicated that the effect of TAL-H was confined to a subset of lymphocytes showing intense blastogenesis and aggregation. By contrast, normal lymphocytes were not stimulated to aggregate or proliferate by TAL-H. A further control experiment using GST (5 μg/ml), the fusion partner of TAL-H prior to proteolysis and purification, showed no evidence of any stimulatory effects on lymphocytes from MS patients.

TABLE III

T Cell Proliferative Responses to Recombinant TAL-H by PBL of MS Patients and Controls

| Patient | Age/Sex | Time | Diagnosis | TAL-H/Ab | Proliferative Response of PBL | | |
|---|---|---|---|---|---|---|---|
| | | | | | Control | TAL-H | S.I. |
| JAB | 40/F | 8 y | R/R | + | 73 ± 10 | 180 ± 15 | 2.5 |
| LAK | 37/F | 3 y | R/R | + | 66 ± 13 | 207 ± 34 | 3.1 |
| KUB | 48/F | 20 y | CP | + | 48 ± 3 | 138 ± 28 | 2.9 |
| PCA | 41/F | 16 y | CP | − | 53 ± 6 | 374 ± 28 | 7.1 |
| TEV | 39/F | 11 y | R/R | − | 49 ± 6 | 504 ± 47 | 10.3 |
| AAB | 31/M | 5 y | R/R | − | 57 ± 7 | 178 ± 15 | 3.1 |
| JWA | 44/M | 12 y | R/R | − | 75 ± 16 | 244 ± 45 | 3.3 |
| ANB | 57/F | 26 y | CP | − | 80 ± 10 | 110 ± 13 | 1.4 |
| GIB | 49/M | 19 y | CP | − | 72 ± 7 | 337 ± 121 | 4.7 |
| CPI | 28/F | 3 y | R/R | − | 77 ± 7 | 209 ± 23 | 2.7 |
| JRO | 59/F | 23 y | CP | − | 43 ± 6 | 195 ± 31 | 4.5 |
| Mean ± s.e.m. | | | | | | | 4.15 ± 0.8* |
| CONTROLS | | | | | | | |
| PRO | 27/F | | | − | 174 ± 37 | 177 ± 37 | 1.0 |
| GIT | 26/M | | | − | 89 ± 21 | 209 ± 64 | 2.3 |
| HAB | 64/F | | | − | 79 ± 5 | 79 ± 7 | 1.0 |
| PEG | 44/F | | | − | 76 ± 24 | 55 ± 21 | 0.7 |
| EST | 26/F | | | − | 42 ± 20 | 60 ± 15 | 1.4 |
| Mean ± s.e.m. | | | | | | | 1.3 ± 0.3 |

Cell proliferation was measured in the presence of 10% autologous serum without (control) or with 1 μg/ml recombinant TAL-H protein (TAL-H). Data are expressed as mean cpm ± s.e.m. or as Stimulation Index (S.I.) of six parallel cultures; *, significant stimulation: p < 0.001. Keys: Time, time after diagnosis; M, male; F, female, y, year; R/R, relapsing/remitting, CP, chronic progressive; A, acute; S, stable Moreover, as low as 1 μg/ml recombinant TAL-H was found to be a significantly more potent stimulator of lymphocyte proliferation than was 30 μg/ml MBP, a well-known myelin antigen, or 10 μg/ml tetanus toxoid (TT), an irrelevant foreign antigen (Table IV). No aggregate formation was noted in the presence of MBP or TT. These results suggest that TAL-H may be a dominant target of myelin-reactive T cells in patients with MS.

The present findings substantiate the existence of cell-mediated immunoreactivity to TAL-H in patients with MS. Levels of proliferative responses to TAL-H were higher than those in response to other myelin antigens (Kerlero de Rosbo, N. et al., 1993, *J. Clin. Invest.* 92:2602). The results clearly indicate that TAL-H may be a prominent target of both cell- and antibody-mediated autoimmunity in patients with MS.

TABLE IV

Proliferative Responses to Recombinant TAL-H, Human Purified Myelin Basic Protein (MBP) and Tetanus Toxoid (TT) by PBL from MS Patients and Controls

| Patient | MBP 30 µg/ml | TAL-H 1 µg/ml | TT 10 µg/ml |
|---|---|---|---|
| ROB | 0.83 | 4.5 | 0.58 |
| BAK | 2.25 | 3.95 | 0.79 |
| ALV | 1.53 | 4.61 | 0.96 |
| EVA | 3.01 | 6.47 | 3.81 |
| BEC | 0.89 | 1.81 | 0.80 |
| Mean ± s.e.m. | 1.7 ± 0.42 | 4.3* ± 0.72 | 1.4 ± 0.61 |
| Controls (n = 4) | | | |
| Mean ± s.e.m. | 1.1 ± 0.22 | 1.6 ± 0.42 | .3 ± 0.43 |

Results are expressed as Stimulation Indices comparing cpm of stimulated cultures to that of control cultures using six parallel wells for each assay. *, significant increase of stimulation as compared to MBP or TT: p < 0.01. The control cpm in this study was in the range of 200–500 cpm for backgrounds and controls and 1000–4000 cpm for TAL-H stimulated MS patient cells.

EXAMPLE IX

Amino Acid Homologies and Immunological Cross-Reactivity between TAL-H and Retroviral Core Proteins Molecular mimicry has been suggested to play a key role in breaking the tolerance towards self proteins and induction of autoinimune disease (Martin, R. et al., 1992, supra; Kaufinan, D. L., et al., 1993, Trends Pharm. Sci. 14:107). Antibodies cross-reactive with a number of viral proteins have been described in patients with MS. In the amino acid sequence of TAL-H, two clusters that showed significant homology to core proteins of human retroviruses were identified (FIG. 13). An N-terminal 50 amino acid segment of TAL-H contains a region of limited homology to the human immunodeficiency virus type 1 (HIV-1) gag p17 protein (Ratner, L. et al., 1987, AIDS Res. Hum. Retrovirus. 3:57). FIGS. 14A and 14B shows additional amino acid sequence homologies between TAL-H and gag/core proteins of HTLV-I, HIV-1, kunjin flavivirus (FLAV), dengue virus (DENGUE), hog cholera virus (HOCV), and poliovirus core protein P2B.

Possibility of cross-reactive antigenic epitopes between TAL-H and HIV-1 gagp17 was raised by immunoreactivity of Ab 169 with gag p17 and gag precursors p57 and p47 in protein lysates of HIV-1-infected PBL (FIG. 15A). HIV-1-encoded proteins in the lysate of infected PBL were identified with a panel of HIV-1 gag p17, gag p24, env gp41 and gp120-specific antibodies. Presence of cross-reactive epitopes in TAL-H and HIV-1 gag p17 was flirther substantiated by binding of HIV-1-gag p17-reactive human antibody F06 (FIG. 15B) and gag p17-specific sheep antibodies to recombinant TAL-H (FIG. 15C). Potential significance of four consecutive amino acid residues, Ala-Asp-Thr-Gly (AD µg), shared between TAL-H and HIV-1 gag p17 (FIG. 13) was demonstrated by utilization of Gag4, a recombinant protein containing the p17 C-terminus, all of p24, and the p15 N-terminus while lacking the first 145 amino acids including the AD µg residues at positions 120–123. As shown in Figure, panel C, the polyclonal HIV-1 gag p17-specific sheep antibody showed immunoreactivity with both TAL-H and Gag4 but failed to react with gag p24. Alternatively, the anti-HIV gagp24 antibody displayed specific reactivity to the Gag4 construct and gagp24 but failed to react with TAL-H. Ab 169 recognizing the full-length gag p17 protein failed to react with the truncated polypeptide in the Gag4 construct. These results indicate that the cross-reactive epitope with TAL-H is contained within the N-terminal segment of HIV-1 gagp17. The four consecutive amino acids, AD µg, present in both TAL-H and the N-terminal segment of HIV-1 gag p17 are likely to represent the core of cross-reactive epitopes.

Figure 16A:
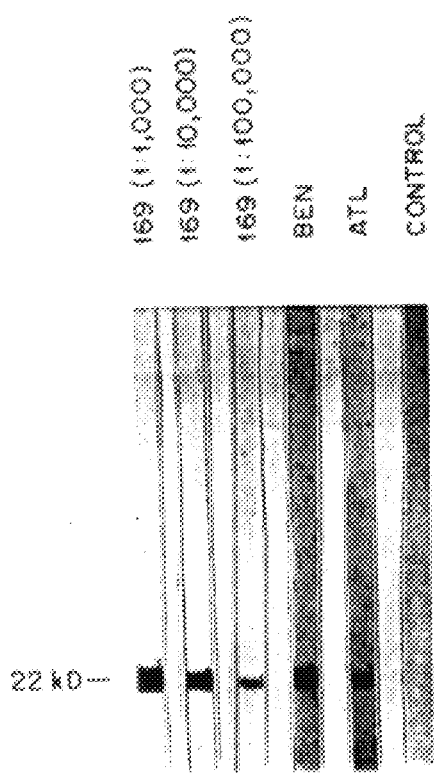
FIGS. 16A and 16B shows detection of cross-reactive antigenic epitopes between recombinant TAL-H and recombinant HTLV-I gag p24 proteins by Western blot analysis. The 22 kDa recombinant TAL-H protein, comprising the N-terminal 140 amino acids, was purified by electroelution from preparative sodium dodecyl sulfate polyacrylamide gel electrophoresis in two cycles. Recombinant proteins were separated by SDS-PAGE and transferred to nitrocellulose membrane, and incubated with antibodies as earlier described. Immunoreactivities of TAL-H Ab169 and sera from patient BEN (essential cryoglobulinemia), and a prototype HTLV-I-infected patient (ATL) with recombinant TAL-H and HTLV-I gag p24 are shown in FIGS. 16A and 16B, respectively. Control serum is from a normal blood donor. Sera were added to Western blot strips at a dilution of 1/100 unless indicated otherwise.
Figure 16B:
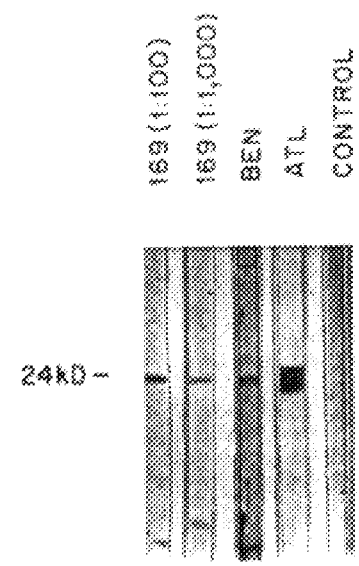

In order to determine the significance of amino acid sequence homologies between TAL-H and HTLV-I proteins, reactivity of HTLV-I antibodies to recombinant TAL-H was evaluated. HTLV-I specific antibodies including rabbit antisera raised against HTLV-I virion lysate and human sera from five HTLV-I infected adult T-cell leukemia (ATL) patients reacted with recombinant TAL-H protein (representative Western blots are shown in FIG. 16A). Conversely, TAL-H antibody 169 cross-reacted with a recombinant HTLV-I gag p24 protein at a 1:1000 dilution (FIG. 16B). These data indicated the presence of cross-reactive antigenic epitopes in TAL-H and HTLV-I gag p24. Three sets of three consecutive amino acids, Gln-Leu-Lys, containing two polar and highly charged amino acids (Gln and Lys), present in both the TARE-encoded segment of TAL-H (residues 17–19) and HTLV-I gag (residues 45–47) (Seiki, M. et al. (1983) Proc. Natl. Acad. Sci. USA 80: 3618–3622), Leu-Ala-Ala (residues 50–52 in TAL-H and residues 248–250 in HTLV-I gag), as well as Lys-Leu-Leu (residues 257–259 in TAL-H and 312–314 in HTLV-I gag) are likely to be the core of cross-reactive epitopes. Sera of five of the TAL-H seropositive MS patients (ADE, BUR, JOS, ROB, and VAS) and of the ECG patient (BEN) also reacted with recombinant HTLV-I gag p24 (data for BEN are shown in FIGS. 16A and 16B). Thus, autoantigenicity of TAL-H could explain the presence of HTLV-I gag-reactive autoantibodies in a subset of patients with MS (Banki, K. et al., (1992) Proc. Natl. Acad. Sci. USA, 89: 1939–1943; Koprowski, H. et al., 1985, Nature 318:154; Ohta, M. et al., 1986, J. Immunol. 137:3440; Ranki, A. et al., 1988, N. Engl. J. Med. 318:448) and, alternatively, molecular mimicry between HTLV-I and other retroviral core proteins may trigger autoimmunity toward TAL-H.

There are a number of possible mechanism for generation of TAL-H specific autoantibodies. First, molecular mimicry, that is, infection by an exogenous agent, such as a retrovirus with cross-reactive epitopes, may trigger TAL-H antibodies. The present inventor and others have not found conclusive evidence for the involvement of exogenous retroviruses in human autoimmunity (Banki et al., 1992, supra). Nevertheless, it is possible that a retrovirus responsible for provoking autoimmunity has been cleared from the CNS, so the absence of viral particles or DNA is not conclusive (French-Constant, C., 1994, Lancet 343:271). Viral core proteins are a usual target of the immune response during viral infections. Because of its oligodendrocyte-specific expression and presence of cross-reactive autoantigenic epitopes in its N-terminal retrotransposon-encoded region, TAL-H may be a key target of autoimmunity triggered by infection with HTLV-I and other retroviruses.

Since sera of all HTLV-I-infected individuals tested showed cross-reactivity with TAL-H, the involvement of this virus in another demyelinating disease of the CNS, HTLV-I associated myelopathy or tropical spastic paraparesis (TSP), is also suggested (Gessain, A. et al., 1985, Lancet ii:407; Jacobson, S. et al., 1988, Nature 331:540).

Presence of cross-reactive epitopes between HIV-1 gag p17 and TAL-H may be related to neurological manifestations of AIDS (Price, R. W. et al., 1988, Science 239:586). Thus, infections by retroviruses carrying a TAL-H related core protein may potentially trigger an autoimmune attack against oligodendrocytes. Although TAL-H is located primarily in the cytosol, antigenic peptides of cytosolic proteins can be processed and associated intracellularly with MHC molecules and exported to the cell surface (Germain, R. N., 1986, *Nature* 322:687; Nuchtem, J. G. et al., 1989, *Nature* 339:223). Thus, TAL-H epitopes presented on the cell surface would become targets of immune responses originally directed to a cross-reactive viral core protein. The consequent destruction of target cells, such as oligodendrocytes, would release more TAL-H from the cytoplasm which, in turn, would further stimulate lymphocytes already primed by the viral antigen, thus perpetuating the immune response long after the elimination of the viral infection. Since expression of TAL-H appears to be confined to the oligodendroglia in the brain, the resultant autoimmune process would lead to a selective destruction of oligodendrocytes.

Autologous proteins may also trigger an immune response upon presentation in large quantities, usually accompanying extensive tissue destruction (Griffiths, M. M. et al., 1981, *Arth. Rheum.* 24:781; Reuter, R. et al., 1986, *Proc. Natl. Acad. Sci. USA* 83:8689). While TAL-H constitutes 1–3% of the total protein content of oligodendrocytes, MBP makes up as much as 30% of the CNS myelin (Lees, M. B. et al., 1984, In: MYELIN, P. Morrell, ed, Plenum New York, pp197–224). Thus, generation of antibodies secondary to tissue injury would be expected to result in antibodies to the highly charged MBP protein as to TAL-H. However, antibodies to MBP are absent in patients with MS.

EXAMPLE X

Overexpression of TAL in Eukaryotic Cells

The TAL-H gene was transfected into, and overexpressed in eukaryotic cells according to the following procedures. The starting plasmid was the pMexRHneo eukaryotic expression plasmid (Ohtani, K. et al., *Nucl. Acid Res.* 17:1589–1604 (1989)) containing an expressible form of the HTLV-I tax gene. The tax gene was excised with HpaI. The vector was blunt ended. The TAL-H construct used to replace tax was a full length 1011 bp cDNA (including a polyadenylation site) made as a HindIII-SacII fragment from a shuttle vector. The TAL-H construct was blunt ended and ligated into the vector, yielding a vector designated pTAL-neo. Expression of the TAL-H gene was under the control of an inducible metallothionein promoter which is induced with CdCl.

pTALneo was transfected by incorporation (see Banki et al., *AIDS Res. Human Retrovir.* 10:303–308 (1994)) into Jurkat cells (ATCC#CRL8163; a human T cell leukemia line). Neomycin-resistant transfectants were selected by conventional methods using G418 for two weeks. Transfected cells were tested for the expression of TAL-H by Western blot using Ab 169, described above. Cells were induced by 4 days of incubation with 5 TM CdCl. Several lines were found to overexpress TAL-H by at least 2–3 fold over background as determined by band density upon Western analysis.

Thus, TAL-H can be successfully transfected into and expressed in a human cell line. This opens the way to use of gene therapy approaches for treating diseases associated with transaldolase deficiency. Such a deficiency may be present in people having known sensitivities to oxidizing agents, similar to the glucose-6-phosphate dehydrogenase deficiency associated with such sensitivity. Interestingly, this enzyme is the rate limiting step of the oxidative phase of the PPP, whereas TAL is the rate-limiting step of the non-oxidative phase (see FIG. 17).

EXAMPLE XI

Central Nervous System Lymphocytes Infiltration in Rats Immunized with TAL-H Lewis rats (five 8 week old females were injected subcutaneously in two sites with 200 μg TAL-H in complete Freund's adjuvant (CFA). Two weeks later the immunization was repeated using incomplete Freud's adjuvant (ICFA). Five negative control animals were injected only CFA and ICFA at the same times. Three weeks after the second immunization, animals were sacrificed by cervical dislocation and histologically evaluated.

Animals were perfused with 2% paraformaldehyde and 1% glutaraldehyde in PBS prior to removal of spinal columns. Brain and spinal cords were dissected from the surrounding tissue and were formalin-fixed and embedded in paraffin. Paraffin sections (10 μm) were stained with Periodic acid Schiff-Hematoxylin and were analyzed for evidence of perivascular infiltration by mononuclear cells.

All the TAL-H immunized rats examined showed perivascular infiltration in the brain. Kidneys and livers showed no similar signs of infiltration. All the TAL-H immunized rats had high titer antibodies to TAL-H as tested by Western blots. None of the control animals showed any perivascular infiltration or anti-TAL-H antibodies.

Brains and spinal cords will be stained with Luxol fast blue for evidence of demyelination. Lymphocytes from such immunized animals will be tested for T cell reactivity to TAL-H by proliferation assays.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated DNA molecule encoding (i) a human tansaldolase protein molecule SEQ ID NO:2, (ii) a peptide fragment thereof or (iii) a functional derivative thereof, or an allelic variant of said transaldolase-encoding DNA molecule, which peptide fragment or functional derivative comprises one or more T cell epitopes or one or more B cell/antibody epitopes,
    with the proviso that said DNA molecule is not:

(a) an oligonucleotide of 18 nucleotides encoding Thr-Leu-Leu-Phe-Ser-Phe; Tyr-Asn-Tyr-Tyr-Lys-Lys; or Ala-Asn-Thr-Asp-Lys-Lys;

(b) an oligonucleotide of 21 nucleotides encoding Asp-Arg-Ile-Leu-Ile-Lys-Leu; Thr-Thr-Val-Val-Ala-Asp-Thr; or Ala-Cys-Ala-Glu-Ala-Gly-Val;

(c) an oligonucleotide of 24 nucleotides encoding Gln-Ala-Val-Ala-Cys-Ala-Glu-Ala; or Val-Val-Ala-Asp-Thr-Gly-Asp-Phe;

(d) an oligonucleotide of 27 nucleotides encoding Thr-Thr-Val-Val-Ala-Asp-Thr-Gly-Asp; Thr-Leu-Leu- Phe-Ser-Phe-Ala-Gln-Ala; or Ser-Thr-Glu-Val-Asp-Ala-Arg-Leu-Ser;

(e) an oligonucleotide of 33 nucleotides encoding Tyr-Lys-Thr-Ile-Val-Met-Gly-Ala-Ser-Phe-Arg; or Thr-Thr-Asn-Pro-Ser-Leu-Ile-Leu-Ala-Ala-Ala;

(f) an oligonucleotide of 36 nucleotides encoding Pro-Gln-Asp-Ala-Thr-Thr-Asn-Pro-Ser-Leu-Ile-Leu; or Leu-Ile-Ser-Pro-Phe-Val-Gly-Arg-Ile-Leu-Asp-Trp;

(g) an oligonucleotide of 42 nucleotides encoding Val-Thr-Leu-Ile-Ser-Pro-Phe-Val-Gly-Arg-Ile-Leu-Asp-Trp; or Gly-Arg-Val-Ser-Thr-Glu-Val-Asp-Ala-Arg-Leu-Ser-Phe-Asp; or (h) an oligonucleotide of 45 nucleotides encoding Pro-Gly-Arg-Val-Ser-Thr-Glu-Val-Asp-Ala-Arg-Leu-Ser-Phe-Asp;

and which DNA molecule is substantially free of other human DNA molecules with which it is natively associated.

2. A DNA molecule according to claim 1 which is a cDNA sequence.

3. A DNA molecule according to claim 1 having the nucleotide sequence SEQ ID NO:1.

4. A recombinant DNA molecule according to claim 1 encoding a peptide having the amino acid sequence:

(a) residues 1–139 of SEQ ID NO:2, or (b) residues 150–337 of SEQ ID NO:2.

5. A recombinant DNA molecule according to claim 1 encoding a peptide selected from the group consisting of SEQ ID NO:16, SEQ ID NO:17, SEQ ID NO:18, SEQ ID NO:19, SEQ ID NO:20, SEQ ID NO:21 and SEQ ID NO:22.

6. A recombinant DNA molecule according to claim 1 encoding a peptide or functional derivative which peptide or derivative comprises:

(a) one or more T helper cell epitopes each having at least about 8 amino acids (b) one or more cytotoxic T cell epitopes each having between about 8 and 12 amino acids or (c) one or more B cell or antibody epitopes having at least about 6 amino acids.

7. A recombinant DNA molecule according to claim 1 encoding a peptide or functional derivative which peptide or derivative has one or more of the following activities:

(a) inhibits a proliferative response of transaldolase-reactive T lymphocytes, (b) inhibits cytotoxicity of transaldolase-reactive cytotoxic T lymphocytes; or (c) inhibits the binding of a transaldolase-specific antibody to transaldolase.

8. A DNA molecule according to claim 1 which is an expression vehicle.

9. The DNA molecule of claim 8, wherein said expression vehicle is a plasmid.

10. A prokaryotic host transformed with the DNA molecule of claim 9.

11. A eukaryotic host transfected with a DNA molecule according to claim 8.

12. A DNA molecule which is a promoter or enhancer sequence for the DNA molecule of claim 1, and is selected from the group consisting of SEQ ID NO:23 and SEQ ID NO:24.

13. A process for preparing a human transaldolase protein peptide or a functional derivative thereof, said process comprising:

(a) culturing the host of claim 10 which expresses said protein, peptide or functional derivative under culturing conditions;

(b) expressing said protein, peptide or functional derivative; and (c) recovering said protein, peptide or functional derivative from said culture.

14. A process for preparing a human transaldolase protein, peptide or a functional derivative thereof, said process comprising:

(a) culturing the host of claim 11 which expresses said protein, peptide or functional derivative under culturing conditions;

(b) expressing said protein, peptide or functional derivative; and (c) recovering said protein, peptide or functional derivative from said culture.

* * * * *